United States Patent
Gorgoulis et al.

(10) Patent No.: US 11,034,839 B2
(45) Date of Patent: Jun. 15, 2021

(54) COMPOUNDS, LINKED WITH HAPTENS, FOR THE DETECTION OF SENESCENT CELLS

(71) Applicant: THE UNIVERSITY OF MANCHESTER, Greater Manchester (GB)

(72) Inventors: Vassilis Gorgoulis, Athens (GR); Paul Townsend, Manchester (GB); Panayiotis Marakos, Athens (GR); Nikolaos Lougiakis, Athens (GR); Nicole Pouli, Athens (GR); Nikolaos Kastrinakis, Athens (GR)

(73) Assignee: THE UNIVERSITY OF MANCHESTER, Greater Manchester (GB)

( * ) Notice: Subject to any disclaimer, the term of this patent is extended or adjusted under 35 U.S.C. 154(b) by 187 days.

(21) Appl. No.: 16/312,942

(22) PCT Filed: Jun. 28, 2017

(86) PCT No.: PCT/GB2017/051888
§ 371 (c)(1),
(2) Date: Dec. 21, 2018

(87) PCT Pub. No.: WO2018/002613
PCT Pub. Date: Jan. 4, 2018

(65) Prior Publication Data
US 2019/0225812 A1 Jul. 25, 2019

(30) Foreign Application Priority Data
Jun. 28, 2016 (GB) .................... 1611206

(51) Int. Cl.
*C09B 31/053* (2006.01)
*C07D 495/04* (2006.01)
*G01N 1/30* (2006.01)

(52) U.S. Cl.
CPC .......... *C09B 31/053* (2013.01); *C07D 495/04* (2013.01); *G01N 1/30* (2013.01); *G01N 2001/302* (2013.01)

(58) Field of Classification Search
CPC .. C09B 31/053; G01N 1/30; G01N 2001/302; C07D 495/04
See application file for complete search history.

(56) References Cited

U.S. PATENT DOCUMENTS

| | | | |
|---|---|---|---|
| 2015/0065620 A1 | 3/2015 | Banning et al. | |
| 2015/0065697 A1 | 3/2015 | Banning et al. | |
| 2019/0315966 A1* | 10/2019 | Gorgoulis | C07D 239/70 |

FOREIGN PATENT DOCUMENTS

| | | |
|---|---|---|
| EP | 0 460 504 B1 | 4/1994 |
| EP | 1 462 485 A1 | 9/2004 |
| WO | 2014/111112 A1 | 7/2014 |
| WO | 2016/096085 A1 | 6/2016 |

OTHER PUBLICATIONS

U.S. Appl. No. 16/313,617, filed Dec. 27, 2018, Compounds for the Detection of Senescent Cells.

(Continued)

*Primary Examiner* — Shafiqul Haq
(74) *Attorney, Agent, or Firm* — Seed IP Law Group LLP

(57) ABSTRACT

The present disclosure relates to compounds of the formula (1) that function as senescent cell detectors: wherein the SBB analogues refer to de novo synthesized derivatives with structural similarity to the Sudan Black B dye, L is an appropriate chemical bond and hapten is biotin, or digoxigenin, or 2,4-dinitrophenol, or fluorescein, but more prefer- (Continued)

ably biotin. The present invention also relates to processes for the preparation of these compounds, to their use in the detection of senescent cells, to methods of detecting senescence in cells and to kits comprising said compounds.

(1)

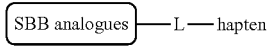

14 Claims, 16 Drawing Sheets

(56) References Cited

OTHER PUBLICATIONS

Georgakopoulou et al., "Specific lipofuscin staining as a novel biomarker to detect replicative and stress-induced senescence. A method applicable in cryo-preserved and archival tissues," *Aging* 5(1):37-50, 2013.
Great Britain Search Report, dated Mar. 29, 2017, for Great Britain Application No. 1611206.2, 3 pages.
Great Britain Search Report, dated Mar. 29, 2017, for Great Britain Application No. 1611208.8, 4 pages.
O'Brien et al., "N,N'-Disubstituted Naphthyl(Azo)-2,3-Dihydroperimidine Blue Dyes Exhibiting High Solubility in Ferroelectric Liquid Crystal Hosts," *Mol. Cryst. Liq. Cryst.*, 220:167-175, 1992.

\* cited by examiner

LG56

LG52

LG39 a.

b.

COMPOUNDS, LINKED WITH HAPTENS, FOR THE DETECTION OF SENESCENT CELLS

FIELD OF THE INVENTION

The present disclosure relates to novel chemical compounds that function as senescent cell detectors. The present invention also relates to processes for the preparation of these compounds, to their use in methods for the detection of senescent cells, and to kits comprising these compounds.

BACKGROUND

Senescence is a "cellular state" that reflects a stress condition encountered by a cell rather than a cell becoming "aged". It is characterized by non-reversible arrest of the cell cycle [Gorgoulis & Halazonetis, Curr Opin Cell Biol 2010] and modified cellular function. One of its forms can be induced in response to telomere attrition of chromosomal ends, after an extended number of cell divisions. This form of senescence is known as "replicative senescence". Cells can also enter another form of senescence, independently of telomere length, termed "premature senescence" in response to stressful pathophysiological stimuli [Dimri et al, Proc Natl Acad Sci USA 1995] such as, oncogenic stimuli, increased levels of free radicals (for example reactive oxygen species—ROS) and cell-cell fusion.

Senescence is currently believed to contribute to the processes of development, ageing, cancer (acting both as a tumor barrier and a promoter), degenerative diseases and tissue restoration, as well as to all the potentially chronic inflammatory imbalances, which underpin normal and pathophysiological ageing, and disease [Gorgoulis & Halazonetis, Curr Opin Cell Biol 2010; Chen Q M, Ann N Y Acad Sci 2000; Rodier & Campisi, J Cell Biol 2011; Bartkova J et al, Nature 2006; Halazonetis et al, Science 2008; Liontos et al, Cancer Res 2007; Liontos et al, Am J Pathol 2009]. Ever since cellular senescence was identified as a tumor suppressor mechanism [Bartkova J et al, Nature 2006; Halazonetis et al, Science 2008; Liontos et al, Cancer Res 2007; Liontos et al, Am J Pathol 2009; Shay & Roninson, Oncogene 2004], and as a marker of ageing, a quest for reliable and convenient senescence biomarkers has been conducted [Collado & Serrano, Nat Rev Cancer 2006]. The reason is that accurate recognition of senescent cells is essential for the thorough study of the role of cellular senescence in the development and progression of tissue homeostasis and neoplasms [de Jesus & Blasco, Circ Res 2012]. Furthermore, senescence is induced by a significant number of widely-used age-enhancing therapies, but the precise significance of senescence to the outcome of currently used treatments, such as degenerative disease therapy, is unclear because of the lack of an easy-in-use biomarker that can be adapted to the requirements of clinico-pathological studies [Dimri et al, Proc Natl Acad Sci USA 1995; Collado & Serrano, Nat Rev Cancer 2006]. Notably, such studies are vastly based on the exploitation of archival histologic samples stored.

The current, most popular biomarker for detecting cellular senescence is senescence-associated β-galactosidase activity (SA-β-gal), for which a biochemical assay is employed that identifies increased activity of lysosomal β-D-galactosidase in senescent cells in conditions of suboptimal pH (pH: 6.0) [Dimri et al, Proc Natl Acad Sci USA 1995; Collado & Serrano, Nat Rev Cancer 2006; U.S. Pat. No. 5,491,069]. SA-0 gal is applicable for in vitro and in vivo studies, however, its major limitation is the requirement of fresh/frozen biological material. This technique should be conducted under strictly monitored conditions, always in comparison with a negative control, while the overall stress in cellular systems should be avoided (i.e. serum starvation, confluent cultures which may lead to false-positive results, etc.) [Severino et al, Exp Cell Res 2000]. In addition, SA-β-gal does not indicate exclusively senescent cells and is often used in combination with other supplementary techniques [Collado & Serrano, Nat Rev Cancer 2006]. Moreover, tissue samples should be directly frozen in liquid nitrogen and processed as soon as possible to retain enzymatic activity [Rodier & Campisi, J Cell Biol 2011; Debacq-Chainiaux et al, Nat Protoc 2009]. Hence, as SA-β-gal is not applicable to archival material and its use is rather laborious, many researchers have attempted to establish more convenient senescence biomarkers [Collado & Serrano, Nat Rev Cancer 2006; Binet et al, Cancer Res 2009].

A novel method that bypasses these restrictive disadvantages has been recently developed [Georgakopoulou et al, Aging (Albany N.Y.) 2013].

Specifically, we demonstrated the specific use of lipofuscin staining with Sudan Black B (SBB) as a reliable alternative to SA-β-gal biomarker with the advantage of applicability to archival tissue [Georgakopoulou et al, Aging (Albany N.Y.) 2013]. Lipofuscin (also termed as a "wear and tear" substance, "age-pigment" and "age fluorophore") is a by-product of "aged" cells [Jung et al, Methods Mol Biol 2010; Jung et al, Ann N Y Acad Sci 2007]. Lipofuscin is considered a "hallmark of ageing" because its concentration increases with age and is inversely correlated with expected lifespan, especially in post-mitotic and stable cells [Brunk & Terman, Free Radic Biol Med 2002]. Due to its association with aging, it was hypothesized that detection of lipofuscin could be used as an alternative method for identifying senescent cells. Lipofuscin accumulates in the cytosolic compartment of non-dividing cells and mainly in the lysosomes due to its non-soluble and non-degradable nature [Jung et al, Methods Mol Biol 2010; Jung et al, Ann N Y Acad Sci 2007; Hohn et al, Free Radic Biol Med 2010]. It consists of oxidized and cross-linked proteins, lipids and metals (copper and iron) [Jung et al, Ann N Y Acad Sci 2007; Hohn et al, Free Radic Biol Med 2010]. It may be detected with fluorescence microscopy due to its natural autofluorescence [Dowson & Harris, J Microsc 1981] as well as by the use of histochemical techniques [Jung & Grune, Methods in Molecular Biology 2010; Charles C, Theory and Practice of Histological Techniques 2002]. The SBB technique is a well-known histochemical stain that has been used for many years for the identification of lipofuscin [Glees & Hasan, Norm Pathol Anat (Stuttg) 1976; Robles, Mech Ageing Dev 1978]. In addition, only the SBB stain has the unique property of "masking" the autofluorescence of lipofuscin, so that the latter feature can be used as a control of the method accuracy [Georgakopoulou et al, Aging (Albany N.Y.) 2013]. We have demonstrated that SBB stain can be used as a senescence biomarker [Georgakopoulou et al, Aging (Albany N.Y.) 2013]. To achieve that, we applied SBB in mammalian tissues and cellular systems of both replicative and premature senescence in comparison with SA-β-gal in order to test the ability to detect senescent cells and we showed that results of both techniques matched. Most importantly, the SBB could identify senescent cells in paraffin-embedded tissues [Georgakopoulou et al, Aging (Albany N.Y.) 2013]. This property opens a wide horizon of potential applications in various fields of basic and clinical research, including diagnostics, as it allows the exploitation of archiva aterial or the purposes of cellular senescence studies.

The SBB stain is a lipophilic molecule that shows high affinity for the lipid compartment of lipofuscin. The dye is diluted in ethanol but is transferred to lipofuscin, when immobilized tissues/cells are immersed in SBB/ethanol solutions, due to its high lipophilicity (more soluble to lipidic parts of lipofuscin than to ethanol) [Georgakopoulou et al, Aging (Albany N.Y.) 2013]. The positive lipofuscin stain reveals blue to black intracellular granules in cellular systems and frozen tissues [Georgakopoulou et al, Aging (Albany N.Y.) 2013], and brown to black granules in paraffin embedded tissues [Georgakopoulou et al, Aging (Albany N.Y.) 2013]. Results from our group have extensively shown that the SBB-specific lipofuscin stain is highly selective for the detection of senescent cells and this may be due to the fact that lipofuscin presence is causally related to the phenomenon of cellular senescence [Georgakopoulou et al, Aging (Albany N.Y.) 2013]. The above technique shows excellent results, it is easily applicable and it has been evaluated in various cellular systems and frozen tissues [Georgakopoulou et al, Aging (Albany N.Y.) 2013]. However, when it comes to histological samples embedded in paraffin, the identification of SBB-positive granules requires a very high magnification, such as 630×, calling for a highly skilled and experienced researcher to perform the evaluation [Georgakopoulou et al, Aging (Albany N.Y.) 2013]. The inevitable presence of smaller granules in paraffin-embedded tissue could be possibly attributed to partial lipid striping of the lipofuscin molecule during the preparation of samples (deparaffinisation). In addition, the necessity to have saturated ethanol-SBB solutions to achieve optimal performance for this staining process imposes practical difficulties during its application.

What is needed are new chemical compounds that possess the same ability of SBB to react specifically with lipofuscin and as such reveal the presence of senescent cells as single ones or in mixed cell populations. These compounds should ideally have a high solubility in ethanol, be linked with haptens, preferably biotin, and permit visualization of senescent cells by applying conventional streptavidin-HRP/DAB complex staining procedures, or other signal generating systems, that specifically use the hapten moiety to amplify the detection signal (FIG. 1).

SUMMARY

The present invention relates to the design and de novo synthesis from simple molecules of novel chemical compounds, which are the reaction products of de novo synthesized Sudan Black B analogues (SSB analogues) with haptens, coupled with appropriate chemical bonds as defined herein.

The SSB analogues linked with hapten, preferably biotin, allow for visualization of senescent cells in a simple accurate, straightforward and readily applicable manner through employing conventional streptavidin-HRP/DAB complex based staining methodologies and overcome the application limitations of SBB staining of senescent cells. The novel chemical compounds have the ability to react with lipofuscin, in an analogous manner to the histochemical dye SBB but with improved performance. In addition, these compounds show high solubility in ethanol.

The novel chemical compounds are used for the detection of senescent cells in biological samples wherein the biological samples can be in either fresh or preserved state.

Thus, in one aspect, there is provided a compound, or a salt or solvate thereof, as defined herein.

In a second aspect there is provided a process for preparation of the compounds as defined herein.

In another aspect, there is provided the use of a compound, or a salt or solvate thereof, as defined herein, for the detection of senescent cells.

In another aspect, there is provided the use of a compound, or a salt or solvate thereof, as defined herein, for the detection of single senescent cells or senescent cells in mixed cell populations.

In another aspect, there is provided the use of a compound, or a salt or solvate thereof, as defined herein, for the detection of senescent cells.

In another aspect, there is provided a method of detecting senescence by contacting a compound, or a salt or solvate thereof, as defined herein, with a sample of single or mixed cells, in the presence of lipofuscin.

In a further aspect, there is provided a kit as defined herein.

Features, including optional, suitable, and preferred features in relation to one aspect of the invention may also be features, including optional, suitable and preferred features in relation to any other aspects of the invention.

DETAILED DESCRIPTION

Definitions

Unless otherwise stated, the following terms used in the specification and claims have the following meanings set out below.

In this specification the term "alkyl" includes both straight and branched chain alkyl groups. References to individual alkyl groups such as "propyl" are specific for the straight chain version only and references to individual branched chain alkyl groups such as "isopropyl" are specific for the branched chain version only. For example, "(1-6C)alkyl" includes (1-4C)alkyl, (1-3C)alkyl, propyl, isopropyl and t butyl. A similar convention applies to other radicals, for example "phenyl(1-6C)alkyl" includes phenyl(1-4C)alkyl, benzyl, 1 phenylethyl and 2 phenylethyl.

The term "(m-nC)" or "(C) group" used alone or as a prefix, refers to any group having m to n carbon atoms.

The term "aryl" means a cyclic or polycyclic aromatic ring having from 5 to 12 carbon atoms. The term aryl includes both monovalent species and divalent species. Examples of aryl groups include, but are not limited to, phenyl, biphenyl, naphthyl and the like. In particular embodiment, an aryl is phenyl.

The term "aryl(1-10C)alkyl" means an aryl group covalently attached to a (1-10C)alkylene group, both of which are defined herein. Examples of aryl-(1-10C)alkyl groups include benzyl, phenylethyl, and the like.

The term "optionally substituted" refers to either groups, structures, or molecules that are substituted and those that are not substituted. The term "wherein a group is optionally substituted" suitably means that (any) one of the hydrogen radicals of the group is substituted by any suitable functional group. For example, the term "optionally substituted" may refer to the optional substitution by one or more of the following groups from halo, trifluoromethyl, trifluoromethoxy, amino, cyano, hydroxy, carboxy, carbamoyl, sulphamoyl, aryl, heteroaryl, (1-6C)alkyl, (3-8C)cycloalkyl or (1-6C)alkoxy.

Compounds of the Invention

Figure 1:
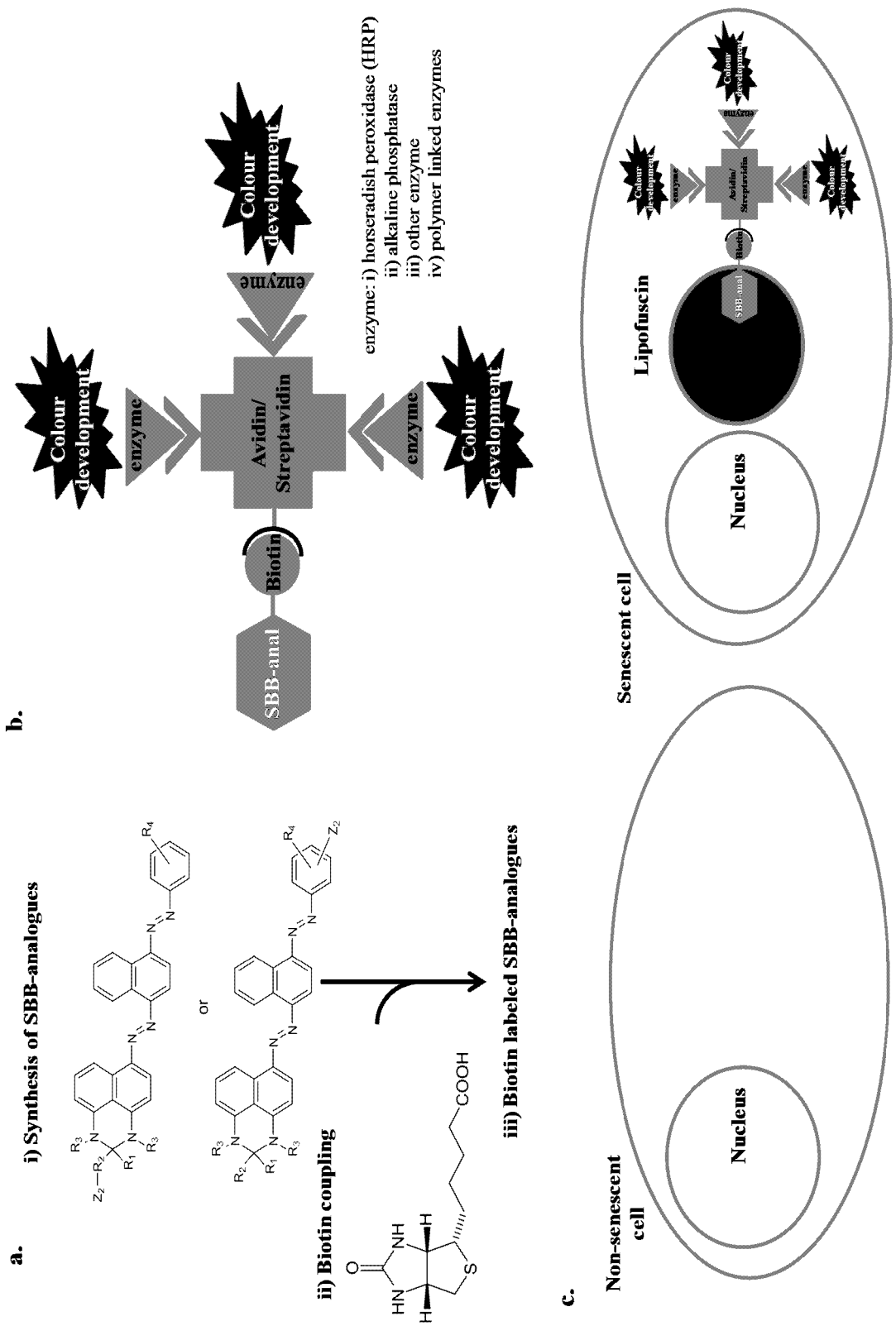
FIG. 1. The SBB stain sensitivity and overall assay readout will be improved by de novo synthesizing new Sudan Black B (SBB) analogues linked with a hapten (in the illustrated case biotin) (a) and then binding of these molecules to enzyme-streptavidin or other complexes (b) suitable for color/signal development in order to detect and visualize senescent cells (c).

We propose the design and de novo synthesis—i.e. the generation from the beginning, using simple molecules—of chemical compounds that can react specifically with lipofuscin, in a similar fashion to SBB, within senescent cells only, and their chemical coupling to a hapten molecule, such as biotin (FIG. 1a). The presence of the hapten will allow detection and visualization through employing immunohistochemical like staining procedures (FIG. 1b, 1c). The stain will then reveal an intense intracellular signal, usually in the form of color or fluorescence emission or other (FIG. 1b, 1c), in lipofuscin-positive cells, making them easily identifiable to the expert and non-expert researcher and clinician. Visualization will be feasible through optical microscopy alone or coupled with available image acquisition equipment.

The SBB compound ($C_{29}H_{24}N_6$) shows high stability due to its extended aromatic system and, hence, its targeted chemical modification requires the de novo synthesis, starting from simple molecules, for the preparation of the new desired compounds. The newly synthesized derivatives possess an appropriate substituent, such as a hydroxyl group or a carboxyl group or an amino group, primary or secondary, which can serve as a site for coupling to a hapten molecule, via an appropriate chemical bond, such as ester bond or amide bond or ether bond. The haptens that are suitable for coupling to the new derivatives are biotin, digoxigenin, 2,4-dinitrophenol, or fluorescein, but more preferably biotin. More specifically, the valeric acid side chain of biotin can be used as the reactive center that allows its coupling to the newly synthesized derivatives so that the urea moiety of the vitamin and the thioether remain unmodified for binding to streptavidin [Diamandis Christopoulos, Clin Chem 1991; Bolzati C et al, Nucl Med Biol 2006]. This coupling would require the existence of a suitable functional group in the molecule of the new compounds, such as the hydroxyl group for the preparation of esters or the amino group for the preparation of amides, but more preferably the hydroxyl group. The presence of an ester group does not perturb the lipophilic character of the resulting molecules thus favoring their affinity for lipofuscin.

Thus, the new compounds are of general formula (1)

SBB analogues — L — hapten   (1)

wherein,
SBB analogues refer to the general structure (2) or (3)

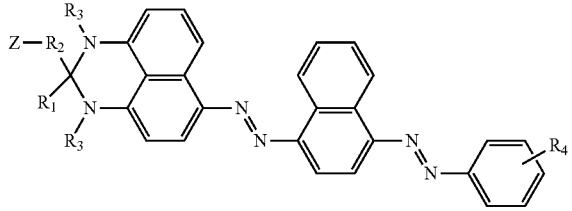

(2)

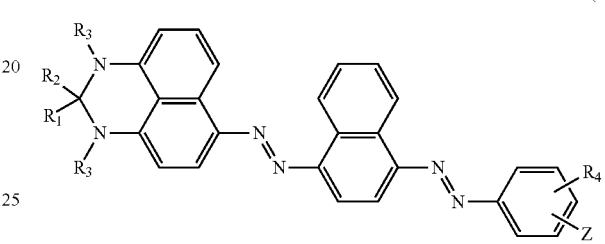

(3)

where
$R_1$ and $R_2$ are each independently selected from:
  i) hydrogen, provided that at least one of $R_1$, $R_2$ is other than hydrogen;
  ii) an optionally substituted (1-10C)alkyl group;
  iii) an optionally substituted aryl group;
  iv) an optionally substituted (1-10C)alkyl-aryl group;
  v) an optionally substituted a 1-(1-10C)alkyl group; or
  vi) $R_1$ and $R_2$ are linked so as to form part of a spiranic cycloalkane group, selected from cyclopentyl, cyclohexyl, cycloheptyl, cyclooctyl, cyclononyl or adamantanyl;
$R_3$ is hydrogen or (1-10C)alkyl group;
$R_4$ is hydrogen, or one or more of the following substituents:
  i) a halogen selected from F, Cl, Br and I;
  ii) $NO_2$;
  iii) $CF_3$;
  iv) $SCH_3$;
  v) an optionally substituted (1-5C)alkyl group;
  vi) a (1-10C)alkoxy group which optionally comprises one or more heteroatoms;
Z is either $Z_1$ or Ar—$Z_1$, and $Z_1$ is selected from —O—, —NH—, —O(CH$_2$)$_n$CH$_2$O—, —(CH$_2$)$_q$O— or —COO—, wherein n is an integer selected from 1 to 9, wherein q is an integer selected from 1 to 4, and wherein Ar is an aryl group optionally substituted with one or more of the following substituents halogen, (1-6C)alkyl, (1-6C)alkenyl or (1-5C)alkoxy;
L is a bond or linker group that links Z to hapten; preferably L is an ester bond or an amide bond or an ether bond; more preferably L is an ester bond;
hapten is biotin, or digoxigenin, or 2,4-dinitrophenol, or fluorescein, but more preferably biotin (4).

(4)

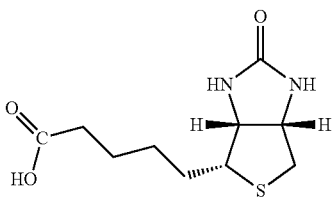

Particular compounds of the present invention include, for example, compounds of the general formula 1 defined above, or salts and/or solvates thereof, wherein, unless otherwise stated, each of $R_1$, $R_2$, $R_3$, $R_4$, L, Z, hapten and any associated substituent groups has any of the meanings defined hereinbefore or in any of paragraphs (1) to (27) hereinafter:

(1) $R_1$ and $R_2$ are each independently selected from:
  i) hydrogen, provided that at least one of $R_1$, $R_2$ is other than hydrogen;
  ii) an optionally substituted (1-8C)alkyl group;
  iii) an optionally substituted aryl group;
  iv) an optionally substituted (1-8C)alkyl-aryl group;
  v) an optionally substituted aryl-(1-8C)alkyl group; or
  vi) $R_1$ and $R_2$ are linked so as to form part of a spiranic cycloalkane group, selected from cyclopentyl, cyclohexyl, cycloheptyl, cyclooctyl, cyclononyl or adamantanyl;

(2) $R_1$ and $R_2$ are each independently selected from
  i) hydrogen, provided that at least one of $R_1$, $R_2$ is other than hydrogen;
  ii) an optionally substituted (1-8C)alkyl group;
  iii) an optionally substituted aryl group;
  iv) an optionally substituted (1-8C)alkyl-aryl group; or
  v) an optionally substituted aryl-(1-8C)alkyl group;

(3) $R_1$ and $R_2$ are each independently selected from:
  i) hydrogen, provided that at least one of $R_1$, $R_2$ is other than hydrogen;
  ii) an optionally substituted (1-4C)alkyl group;
  iii) an optionally substituted aryl group;
  iv) an optionally substituted (1-4C)alkyl-aryl group; or
  v) an optionally substituted aryl-(1-4C)alkyl group;

(4) $R_1$ and $R_2$ are each independently selected from:
  i) hydrogen, provided that at least one of $R_1$, $R_2$ is other than hydrogen;
  ii) a (1-4C)alkyl group;
  iii) an aryl group;
  iv) a (1-4C)alkyl-aryl group; or
  v) an aryl-(1-4C)alkyl group;

(5) $R_1$ and $R_2$ are each independently selected from
  i) hydrogen, provided that at least one of $R_1$, $R_2$ is other than hydrogen;
  ii) an optionally substituted (1-4C)alkyl group; or
  iii) an optionally substituted aryl group;

(6) $R_1$ and $R_2$ are each independently selected from
  i) hydrogen, provided that at least one of $R_1$, $R_2$ is other than hydrogen;
  ii) a (1-4C)alkyl group (e.g. methyl); or
  iii) a phenyl group;

(7) $R_3$ is hydrogen or (1-8C)alkyl group;
(8) $R_3$ is hydrogen or (1-4C)alkyl group (e.g. methyl);
(9) $R_3$ is hydrogen;
(10) $R_4$ is hydrogen, or one or more of the following substituents:
  i) a halogen selected from F, Cl, Br and I;
  ii) $NO_2$;
  iii) $CF_3$;
  iv) $SCH_3$;
  v) a (1-5C)alkyl group; or
  vi) a (1-10C)alkoxy group;

(11) $R_4$ is hydrogen, or one or more of the following substituents:
  i) a halogen selected from F, Cl, Br and I, preferably F or Cl;
  ii) $NO_2$;
  iii) $CF_3$;
  v) a (1-5C)alkyl group (e.g. methyl); or
  v) a (1-5C)alkoxy group (e.g. methoxy);

(12) $R_4$ is hydrogen;
(13) Z is either $Z_1$ or Ar—$Z_1$, and $Z_1$ is selected from —O—, —NH—, —O(CH$_2$)$_n$CH$_2$O—, —(CH$_2$)$_q$O— or —COO—, wherein n is an integer selected from 1 to 4, wherein q is an integer selected from 1 to 4, and wherein Ar is an aryl group optionally substituted with one or more of the following substituents halogen, (1-4C)alkyl, (1-4C)alkenyl or (1-4C)alkoxy;

(14) Z is either $Z_1$ or Ar—$Z_1$, and $Z_1$ is selected from —O—, —NH—, —O(CH$_2$)$_n$CH$_2$O— or —(CH$_2$)$_q$O—, wherein n is an integer selected from 1 to 4, wherein q is an integer selected from 1 to 4, and wherein Ar is an aryl group optionally substituted with one or more of the following substituents halogen, (1-4C)alkyl, (1-4C)alkenyl or (1-4C)alkoxy;

(15) Z is either $Z_1$ or Ar—$Z_1$, and $Z_1$ is selected from —O—, —NH—, —O(CH$_2$)$_n$CH$_2$O— or —(CH$_2$)$_q$O—, wherein n is an integer selected from 1 to 4, wherein q is an integer selected from 1 to 4, and wherein Ar is an aryl group;

(16) Z is either $Z_1$ or Ar—$Z_1$, and $Z_1$ is selected from —O— or —NH—, wherein Ar is an aryl group optionally substituted with one or more of the following substituents halogen, (1-4C)alkyl, (1-4C)alkenyl or (1-4C)alkoxy;

(17) Z is either $Z_1$ or Ar—$Z_1$, and $Z_1$ is selected from —O— or —NH—, wherein Ar is an aryl group;

(18) Z is either $Z_1$ or Ar—$Z_1$, and $Z_1$ is selected from —O— or —NH—, wherein Ar is a phenyl group;

(19) Z is either $Z_1$ or Ar—$Z_1$, and $Z_1$ is —O— and Ar is a phenyl group;

(20) L is an ester bond, an amide bond or an ether bond;
(21) L is an ester bond;
(22) hapten is biotin, digoxigenin or 2,4-dinitrophenol;
(23) hapten is biotin, 2,4-dinitrophenol or fluorescein;
(24) hapten is biotin, 2,4-dinitrophenol or fluorescein;
(25) hapten is biotin, digoxigenin or fluorescein;
(26) hapten is biotin or fluorescein;
(27) hapten is biotin.

Suitably, $R_1$ and $R_2$ are as defined in any one of paragraphs (1) to (6) above. Most suitably, $R_1$ and $R_2$ are as defined in paragraph (6) above.

Suitably, $R_3$ is as defined in any one of paragraphs (7) to (9) above.

Suitably, $R_4$ is as defined in any one of paragraphs (10) to (12) above.

Suitably, Z is as defined in any one of paragraphs (13) to (19) above. Most suitably, Z is as defined in paragraph (19) above.

L is as defined in any one of paragraphs (20) to (21) above.

Suitably, hapten is as defined in any one of paragraphs (22) to (27) above. Most suitably, hapten is as defined in paragraph (27) above.

In an embodiment, the SBB analogue is of general structure (2).

In another embodiment, the SBB analogue is of general structure (3).

Particular Embodiments

In a particular group of compounds of general formula (1), $R_3$ is hydrogen, i.e. the compounds have the structural formula 2b or 3b (sub-definitions of general formula 1) shown below:

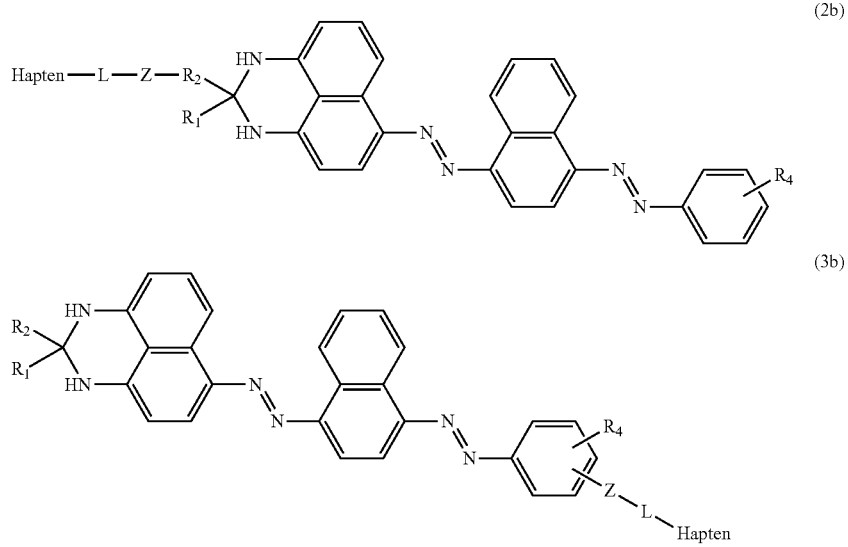

(2b)

(3b)

wherein, $R_1$, $R_2$, $R_4$, Z, L and hapten are as defined hereinabove.

In an embodiment of the compounds of Formula 2b and 3b:
$R_1$ and $R_2$ are as defined in any one of paragraphs (1) to (6) above;
$R_4$ is as defined in any one of paragraphs (10) to (12) above;
Z is as defined in any one of paragraphs (13) to (19) above;
L is as defined in any one of paragraphs (20) to (21) above; and
hapten is as defined in any one of paragraphs (22) to (27) above.

In another embodiment of the compounds of Formula 2b and 3b:
$R_1$ and $R_2$ are as defined in paragraph (6) above;
$R_4$ is as defined in paragraph (12) above;
Z is as defined in paragraph (19) above;
L is as defined in paragraph (21) above; and
hapten is as defined in paragraph (27) above.

In a particular group of compounds of Formula (1), $R_3$ and $R_4$ are hydrogen and $R_1$ is hydrogen or (1-4C)alkyl, i.e. the compounds have the structural formula 2c or 3c (sub-definitions of general formula 1) shown below:

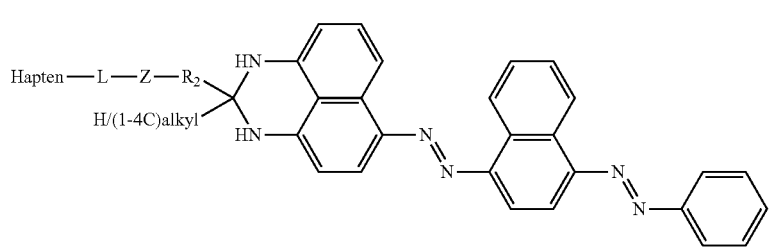

(2c)

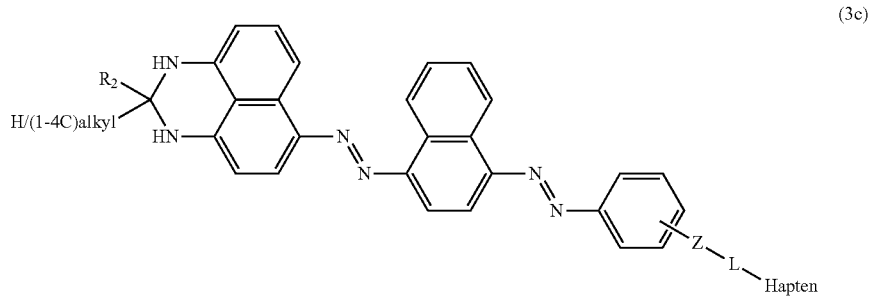

(3c)

wherein, $R_2$, Z, L and hapten are as defined hereinabove.

In an embodiment of the compounds of Formula 2c and 3c:
R$_2$ is as defined in any one of paragraphs (1) to (6) above;
Z is as defined in any one of paragraphs (13) to (19) above;
L is as defined in any one of paragraphs (20) to (21) above; and
hapten is as defined in any one of paragraphs (22) to (27) above.

In another embodiment of the compounds of Formula 2c and 3c:
R$_2$ is as defined in paragraph (6) above;
Z is as defined in paragraph (19) above;
L is as defined in paragraph (21) above; and
hapten is as defined in paragraph (27) above.

Compounds of General Structure (5)

In one embodiment, the appropriate substituent, preferably a hydroxyl group, has been introduced to the 2,3-dihydro-1H-perimidine ring of the SBB compound, leading to compounds of the general structure (5) (a sub-definition of general formula 1).

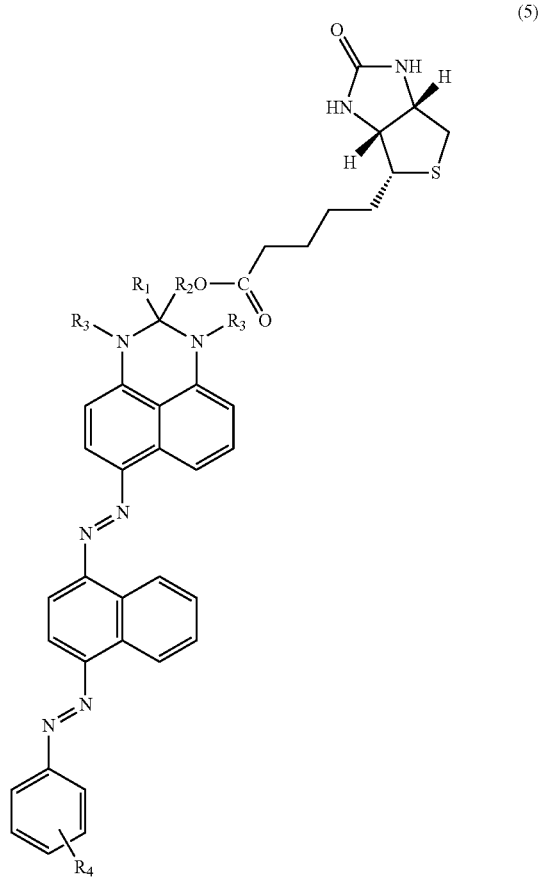

(5)

wherein,
R$_1$ is a (1-10C)alkyl group;
R$_2$ is a (1-8C)alkyl group, an optionally substituted aryl group or an optionally substituted (1-5C)alkyl-aryl group;
R$_3$ is hydrogen or (1-10C)alkyl group;
R$_4$ is hydrogen, or one or more of the following substituents:
 i) halogen selected from F, Cl, Br and I,
 ii) NO$_2$,
 iii) CF$_3$,
 iv) SCH$_3$,
 v) an optionally substituted (5C)alkyl group; or
 vi) a (1-10C)alkoxy group which optionally comprises one or more heteroatoms.

In an embodiment of the compounds of the general structure (5):
R$_1$ is a (1-4C)alkyl group;
R$_2$ is a (1-8C)alkyl group or an optionally substituted aryl group;
R$_3$ is hydrogen or (1-4C)alkyl group; and
R$_4$ is hydrogen, or one or more of the following substituents:
 i) a halogen selected from F or Cl;
 ii) NO$_2$;
 iii) CF$_3$;
 iv) a (1-5C)alkyl group (e.g. methyl); or
 v) a (1-5C)alkoxy group (e.g. methoxy).

In another embodiment of the compounds of the general structure (5):
R$_1$ is a (1-4C)alkyl group (e.g. methyl);
R$_2$ is a (1-4C)alkyl group (e.g. methyl) or an aryl group (e.g. phenyl); and
R$_3$ and R$_4$ are hydrogen.

Compounds of General Structure (6)

In another embodiment the appropriate substituent, preferably a hydroxyl group or the O(CH$_2$)$_n$CH$_2$OH group where n is 1 up to 9, has been introduced to an aryl group present at position 2 of the 2,3-dihydro-1H-perimidine group of the SBB compound, leading to compounds of the general structure (6) (a sub-definition of general formula 1).

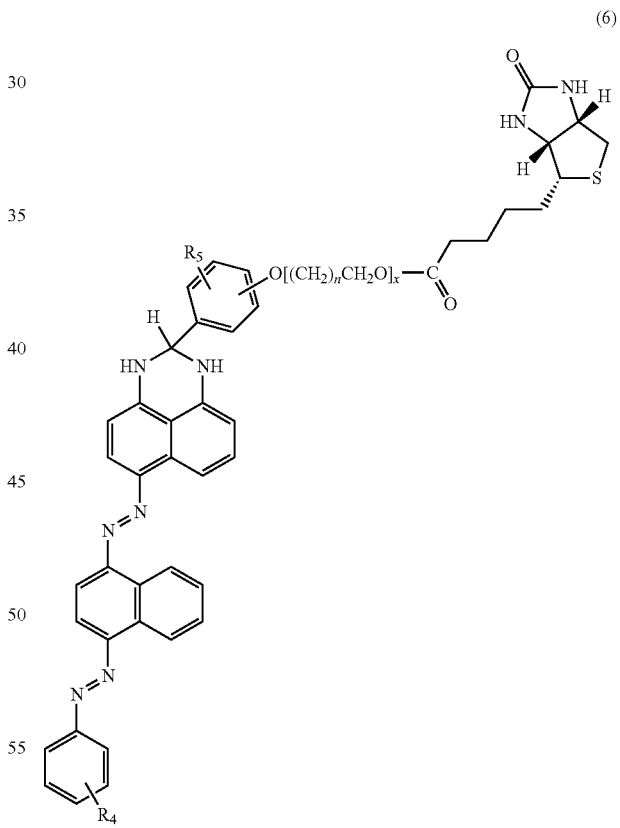

(6)

wherein
x is an integer selected from 0 or 1;
n is an integer selected from 1 to 9;
R$_4$ is hydrogen, or one or more of the following substituents:
 i) halogen selected from F, Cl, Br and I,
 ii) NO$_2$,
 iii) CF$_3$, iv) SCH$_3$,
v) an optionally substituted (1-5C)alkyl group; or
vi) a (1-10C)alkoxy group which optionally comprises one or more heteroatoms;

R$_5$ is hydrogen, or one or more of the following substituents:
i) halogen selected from F, Cl, Br and I;
ii) (1-6C)alkyl group or (1-6C)alkenyl group; or
iii) (1-5C)alkoxy group.

In an embodiment of the compounds of the general structure (6):
x is an integer selected from 0 or 1;
n is an integer selected from 1 to 4;
R$_4$ is hydrogen, or one or more of the following substituents:
i) a halogen selected from F or Cl;
ii) NO$_2$;
iii) CF$_3$;
iv) a (1-5C)alkyl group (e.g. methyl); or
v) a (1-5C)alkoxy group (e.g. methoxy);

R$_5$ is hydrogen, or one or more of the following substituents:
i) halogen selected from F, Cl, Br and 1;
ii) (1-6C)alkyl group; or
iii) (1-5C)alkoxy group.

In another embodiment of the compounds of the general structure (6):
x is an integer selected from 0 or 1;
n is an integer selected from to 4;
R$_4$ and R$_5$ are hydrogen.

Compounds of General Structure (7)

In yet another embodiment the appropriate substituent, preferably a hydroxyl group or the O(CH$_2$)$_n$CH$_2$OH group where n is 1 up to 9, has been introduced to the position 4 of the end terminal aniline unit of SBB compound, leading to compounds of the general structure (7) (a sub-definition of general formula 1).

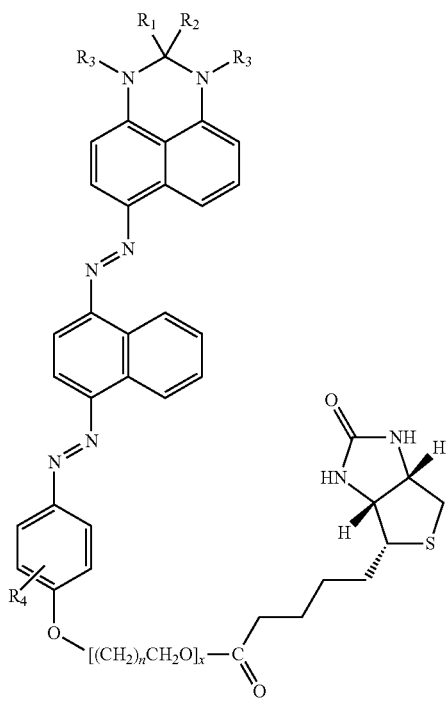

(7)

wherein
x is an integer selected from 0 or 1;
n is an integer selected from 1 to 9;
R$_1$ and R$_2$ are each independently selected from
i) hydrogen, provided that at least one of R$_1$, R$_2$ is other than hydrogen;
ii) an optionally substituted (1-10C)alkyl group;
iii) an optionally substituted aryl group;
iv) part of a spiranic cycloalkane group, selected from cyclopentyl, cyclohexyl, cycloheptyl, cyclooctyl, cyclononyl or adamantanyl;
v) an optionally substituted (OC)alkyl-aryl group; or
vi) an optionally substituted aryl-(1-10C)alkyl group;

R$_3$ is hydrogen or a (1-10C)alkyl group;

R$_4$ is hydrogen, or one or more of the following substituents:
i) halogen selected from F, Cl, Br and I,
ii) NO$_2$,
iii) CF$_3$,
iv) SCH$_3$,
v) an optionally substituted (1-5C)alkyl group; or
vi) a (1-10C)alkoxy group which optionally comprises one or more heteroatoms.

In an embodiment of the compounds of the general structure (7):
x is an integer selected from 0 or 1;
n is an integer selected from to 4;
R$_1$ and R$_2$ are each independently selected from
i) hydrogen, provided that at least one of R$_1$, R$_2$ is other than hydrogen;
ii) a (1-4C)alkyl group;
iii) an aryl group;
iv) a (1-4C)alkyl-aryl group; or
v) an aryl-(1-4C)alkyl group;

R$_3$ is hydrogen or a (1-4C)alkyl group; and

R$_4$ is hydrogen, or one or more of the following substituents:
i) a halogen selected from F or Cl;
ii) NO$_2$;
iii) CF$_3$;
iv) a (1-5C)alkyl group (e.g. methyl); or
v) a (1-5C)alkoxy group (e.g. methoxy).

In another embodiment of the compounds of the general structure (7):
x is an integer selected from 0 or 1;
n is an integer selected from 1 to 4;
R$_1$ and R$_2$ are independently selected from hydrogen or a (1-4C)alkyl group (e.g. methyl); and
R$_3$ and R$_4$ are hydrogen.

Compounds of General Structure (8)

In yet another embodiment the appropriate substituent, preferably a hydroxyl group or the O(CH$_2$)$_n$CH$_2$OH group where n is 1 up to 9, has been introduced to the position 3 of the end terminal aniline unit of SBB compound, leading to compounds of the general structure (8) (a sub-definition of general formula 1).

(8)

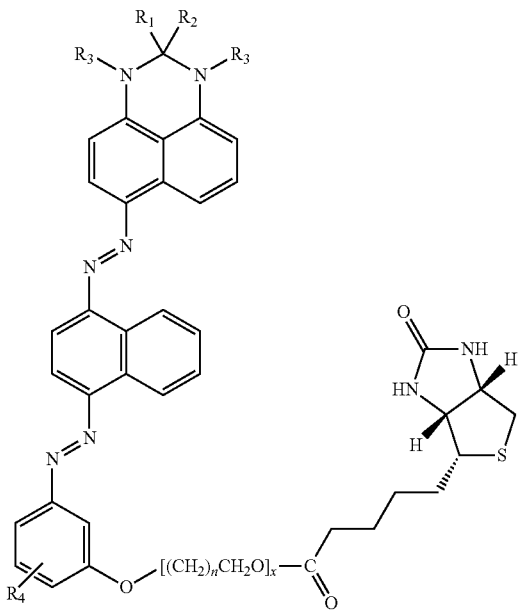

wherein,
x is an integer selected from 0 or 1;
n is an integer selected from 1 to 9;
$R_1$ and $R_2$ are each independently selected from:
  i) hydrogen, provided that at least one of $R_1$, $R_2$ is other than hydrogen;
  ii) an optionally substituted (1-10C)alkyl group;
  iii) an optionally substituted aryl group;
  iv) part of a spiranic cycloalkane group, selected from cyclopentyl, cyclohexyl, cycloheptyl, cyclooctyl, cyclononyl or adamantanyl;
  v) an optionally substituted (1-10C)alkyl-aryl group; or
  vi) an optionally substituted aryl-(1-10C)alkyl group;
$R_3$ is hydrogen or a (1-10C)alkyl group;
$R_4$ is hydrogen, or one or more of the following substituents:
  i) halogen selected from F, Cl, Br and I,
  ii) $NO_2$,
  iii) $CF_3$,
  iv) $SCH_3$,
  v) an optionally substituted (1-5C)alkyl group; or
  vi) a (1-10C)alkoxy group which optionally comprises one or more heteroatoms.

In an embodiment of the compounds of the general structure (8):
x is an integer selected from 0 or 1;
n is an integer selected from to 4;
$R_1$ and $R_2$ are each independently selected from:
  i) hydrogen, provided that at least one of $R_1$, $R_2$ is other than hydrogen;
  ii) a (1-4C)alkyl group;
  iii) an aryl group;
  iv) a (1-4C)alkyl-aryl group; or
  v) an aryl-(1-4C)alkyl group;
$R_3$ is hydrogen or a (1-4C)alkyl group;
$R_4$ is hydrogen, or one or more of the following substituents:
  i) a halogen selected from F or Cl;
  ii) $NO_2$;
  iii) $CF_3$;
  iv) a (1-5C)alkyl group (e.g. methyl); or
  v) a (1-5C)alkoxy group (e.g. methoxy).

In another embodiment of the compounds of the general structure (8):
x is an integer selected from 0 or 1;
n is an integer selected from 1 to 4;
$R_1$ and $R_2$ are independently selected from hydrogen or a (1-4C)alkyl group (e.g. methyl); and
$R_3$ and $R_4$ are hydrogen.

Compounds of General Structure (9)

In yet another embodiment the appropriate substituent, preferably the $(CH_2)_qOH$ group where q is 1 up to 4, has been introduced to the position 4 of the end terminal aniline unit of SBB compound, so that an interposition of an alkyl bridge consisting of methylene units between the aniline group of SBB and the ester moiety is present, leading to compounds of the general structure (9) (a sub-definition of general formula 1).

(9)

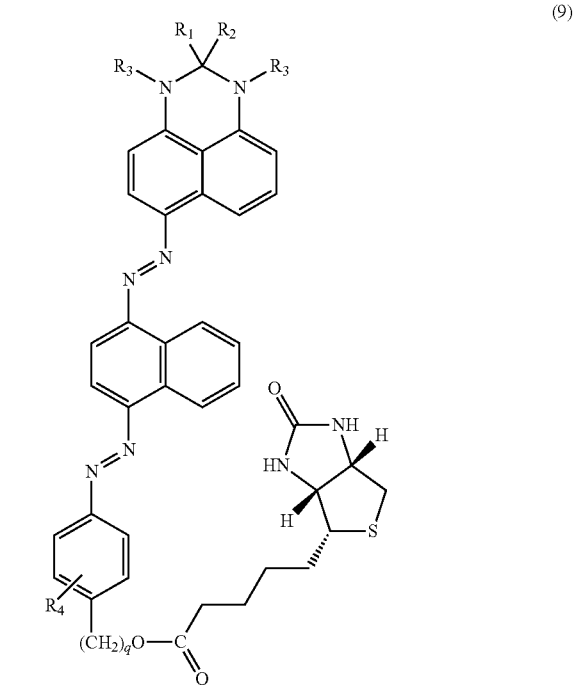

wherein,
q is an integer selected from 1 to 4;
$R_1$ and $R_2$ are each independently selected from:
  i) hydrogen, provided that at least one of $R_1$, $R_2$ is other than hydrogen;
  ii) an optionally substituted (1-10C)alkyl group;
  iii) an optionally substituted aryl group;
  iv) part of a spiranic cycloalkane group, selected from cyclopentyl, cyclohexyl, cycloheptyl, cyclooctyl, cyclononyl or adamantanyl;
  v) an optionally substituted (1-10C)alkyl-aryl group; or
  vi) an optionally substituted aryl-(1-10C)alkyl group;
$R_3$ is hydrogen or a (1-10C)alkyl group;
$R_4$ is hydrogen, or one or more of the following substituents:
  i) halogen selected from F, Cl, Br and I;
  ii) $NO_2$,
  iii) $CF_3$,
  iv) $SCH_3$, v) an optionally substituted (1-5C)alkyl group; or vi) a (1-10C)alkoxy group which optionally comprises one or more heteroatoms.

In an embodiment of the compounds of the general structure (9):

q is an integer selected from 1 to 4;

$R_1$ and $R_2$ are each independently selected from:
i) hydrogen, provided that at least one of $R_1$, $R_2$ is other than hydrogen;
ii) a (1-4C)alkyl group;
iii) an aryl group;
iv) a (1-4C)alkyl-aryl group; or
v) an aryl-(1-4C)alkyl group;

$R_3$ is hydrogen or a (1-4C)alkyl group;

$R_4$ is hydrogen, or one or more of the following substituents:
i) a halogen selected from F or Cl;
ii) $NO_2$;
iii) $CF_3$;
iv) a (1-5C)alkyl group (e.g. methyl); or
v) a (1-5C)alkoxy group (e.g. methoxy).

In an embodiment of the compounds of the general structure (9):

q is an integer selected from 1 to 4;

$R_1$ and $R_2$ are independently selected from hydrogen or a (1-4C)alkyl group (e.g. methyl); and $R_3$ and $R_4$ are hydrogen.

Compounds of General Structure (10)

In yet another embodiment the appropriate substituent, preferably the $(CH_2)_qOH$ group where q is 1 up to 4, has been introduced to the position 3 of the end terminal aniline unit of SBB compound, so that an interposition of an alkyl bridge consisting of methylene units between the aniline group of SBB and the ester moiety is present, leading to compounds of the general structure (10) (a sub-definition of general formula 1).

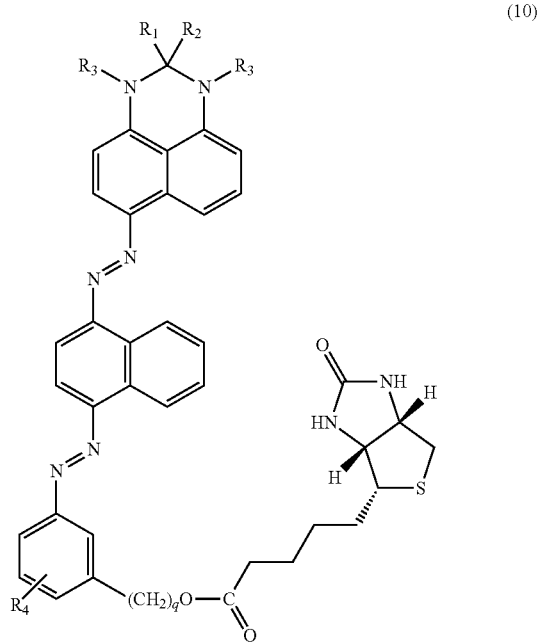

(10)

wherein, q is an integer selected from to 4;

$R_1$ and $R_2$ are each independently selected from:
i) hydrogen, provided that at least one of $R_1$, $R_2$ is other than hydrogen;
ii) an optionally substituted (1-10C)alkyl group;
iii) an optionally substituted aryl group;
iv) part of a spiranic cycloalkane group, selected from cyclopentyl, cyclohexyl, cycloheptyl, cyclooctyl, cyclononyl or adamantanyl;
v) an optionally substituted (1-10C)alkyl-aryl group; or
vi) an optionally substituted aryl-(1-10C)alkyl group;

$R_3$ is hydrogen or a (1-10C)alkyl group;

$R_4$ is hydrogen, or one or more of the following substituents:
i) halogen selected from F, Cl, Br and I,
ii) $NO_2$,
iii) $CF_3$,
iv) $SCH_3$,
v) an optionally substituted (1-5C)alkyl group; or
vi) a (1-10C)alkoxy group which optionally comprises one or more heteroatoms.

In an embodiment of the compounds of the general structure (10):

q is an integer selected from 1 to 4;

$R_1$ and $R_2$ are each independently selected from
i) hydrogen, provided that at least one of $R_1$, $R_2$ is other than hydrogen;
ii) a (1-4C)alkyl group;
iii) an aryl group;
iv) a (1-4C)alkyl-aryl group; or
v) an aryl-(1-4C)alkyl group;

$R_3$ is hydrogen or a (1-4C)alkyl group;

$R_4$ is hydrogen, or one or more of the following substituents:
i) a halogen selected from F or Cl;
ii) $NO_2$;
iii) $CF_3$;
iv) a (1-5C)alkyl group (e.g. methyl); or
v) a (1-5C)alkoxy group (e.g. methoxy).

In an embodiment of the compounds of the general structure (10):

q is an integer selected from 1 to 4;

$R_1$ and $R_2$ are independently selected from hydrogen or a (1-4C)alkyl group (e.g. methyl); and $R_3$ and $R_4$ are hydrogen.

Particular compounds of general formula (1) include any of the compounds exemplified in the present application, or a salt or solvate thereof, and, in particular, any of the following:

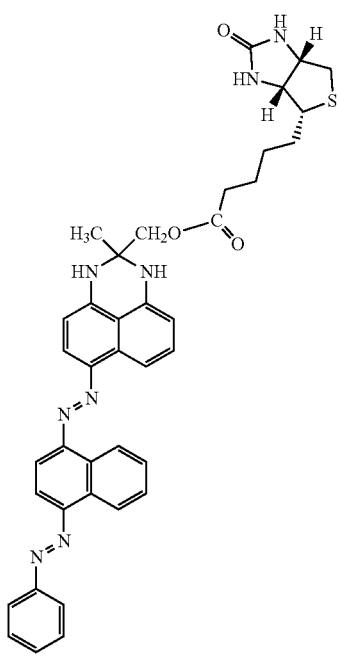
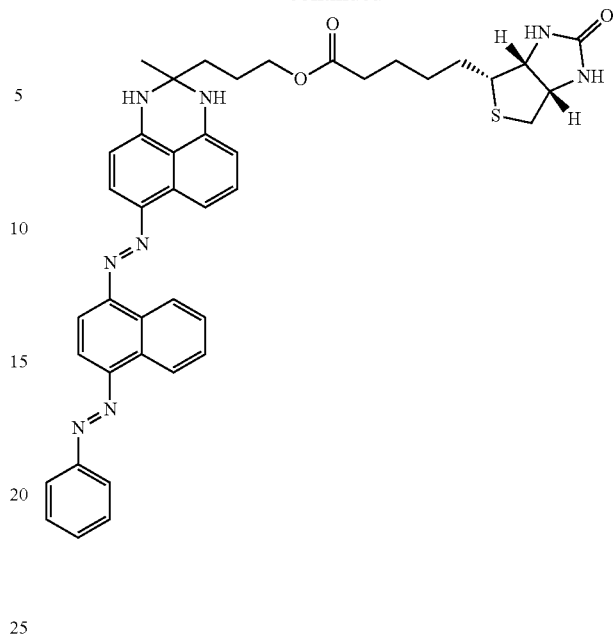
-continued
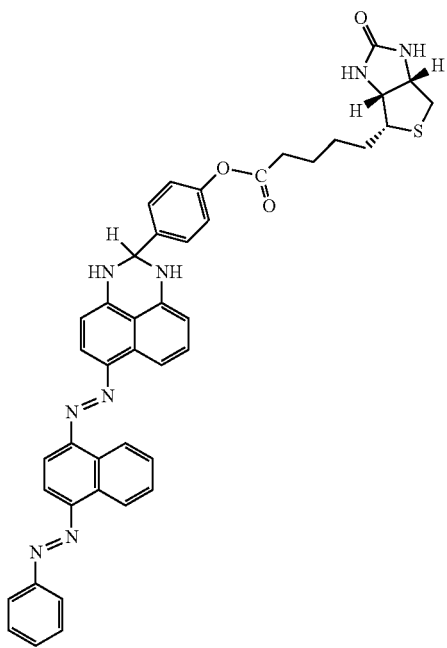
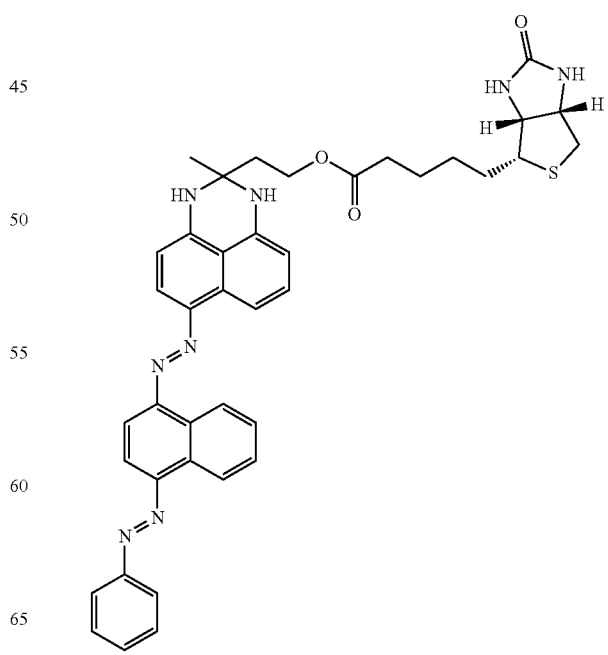

-continued

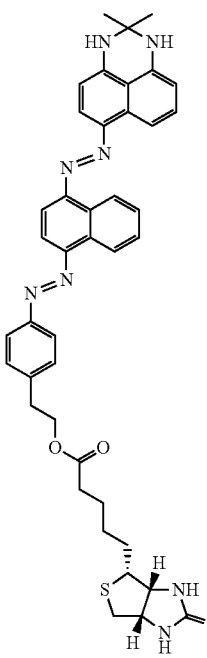

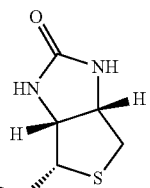

Further compounds of general formula (1) include any of the compounds exemplified in the present application, or a salt or solvate thereof, and, in particular, any of the following:

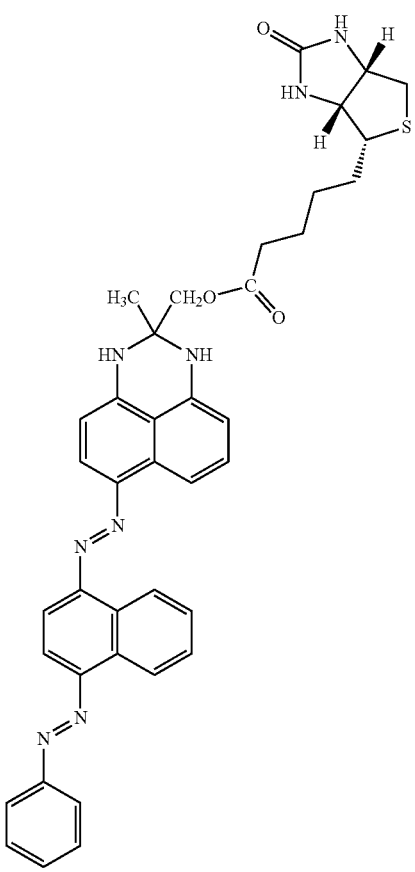

-continued

The various functional groups and substituents making up the compounds of general formula 1 (or compounds of sub-formulae (5) to (10)) are typically chosen such that the molecular weight of the compound of general formula 1 does not exceed 1250. More usually, the molecular weight of the compound will be less than 1100, for example less than 1000, or less than 900, or less than 800.

A suitable salt of a compound of general formula I (or compounds of sub-formulae (5) to (10)) is, for example, an acid-addition salt of a compound of the invention which is sufficiently basic, for example, an acid-addition salt with, for example, an inorganic or organic acid, for example hydrochloric, hydrobromic, sulfuric, phosphoric, trifluoroacetic, formic, citric methane sulfonate or maleic acid. In addition, a suitable pharmaceutically acceptable salt of a cytochrome be inhibitor of the invention which is sufficiently acidic is an alkali metal salt, for example a sodium or potassium salt, an alkaline earth metal salt, for example a calcium or magnesium salt, an ammonium salt or a salt with an organic base which affords a pharmaceutically acceptable cation, for example a salt with methylamine, dimethylamine, trimethylamine, piperidine, morpholine or tris-(2-hydroxyethyl) amine.

Compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn-Ingold-Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The compounds of general formula 1 (or compounds of sub-formulae (5) to (10)) of this invention may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see discussion in Chapter 4 of "Advanced Organic Chemistry", 4th edition J. March, John Wiley and Sons, New York, 2001), for example by synthesis from optically active starting materials or by resolution of a racemic form. Some of the compounds of the invention may have geometric isomeric centres (E- and Z-isomers). It is to be understood that the present invention encompasses all optical, diastereoisomers and geometric isomers and mixtures thereof that possess β-lactamase inhibitory activity.

The present invention also encompasses compounds of general formula 1 (or compounds of sub-formulae (5) to (10)) which comprise one or more isotopic substitutions. For example, H may be in any isotopic form, including $^1$H, $^2$H(D), and $^3$H (T); C may be in any isotopic form, including $^{12}$C, $^{13}$C, and $^{14}$C; and O may be in any isotopic form, including $^6$O and $^{18}$O; and the like.

It is also to be understood that certain compounds of general formula 1 (or compounds of sub-formulae (5) to (10)) may exist in solvated as well as unsolvated forms such as, for example, hydrated forms. It is to be understood that the invention encompasses all such solvated forms that possess β-lactamase inhibitory activity.

Compounds of general formula 1 (or compounds of sub-formulae (5) to (10)) may also exist in a number of different tautomeric forms and references to compounds of general formula 1 (or compounds of sub-formulae (5) to (10)) include all such forms. For the avoidance of doubt, where a compound can exist in one of several tautomeric forms, and only one is specifically described or shown, all others are nevertheless embraced the structural formula of general formula 1 (or compounds of sub-formulae (5) to (10)). Examples of tautomeric forms include keto-, enol-, and enolate-forms, as in, for example, the following tautomeric pairs: keto/enol (illustrated below), imine/enamine, amide/imino alcohol, amidine/amidine, nitroso/oxime, thioketone/enethiol, and nitro/aci-nitro.

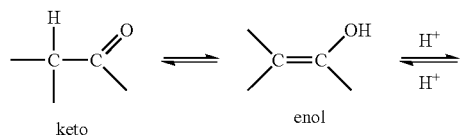

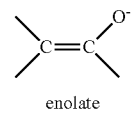

enolate

Compounds of general formula 1 (or compounds of sub-formulae (5) to (10)) containing an amine function may also form N-oxides. A reference herein to a compounds of general formula 1 (or compounds of sub-formulae (5) to (10)) that contains an amine function also includes the N-oxide. Where a compounds of general formula 1 (or compounds of sub-formulae (5) to (10)) contains several amine functions, one or more than one nitrogen atom may be oxidised to form an N-oxide. Particular examples of N-oxides are the N-oxides of a tertiary amine or a nitrogen atom of a nitrogen-containing heterocycle. N-Oxides can be formed by treatment of the corresponding amine with an oxidizing agent such as hydrogen peroxide or a per-acid (e.g. a peroxycarboxylic acid), see for example *Advanced Organic Chemistry*, by Jerry March, 4$^{th}$ Edition, Wiley Interscience. More particularly, N-oxides can be made by the procedure of L. W. Deady (Syn. Comm. 1977, 7, 509-514) in which the amine compound is reacted with m-chloroperoxybenzoic acid (mCPBA), for example, in an inert solvent such as dichloromethane.

Synthesis

The compounds of the present invention can be prepared by any suitable technique known in the art. Particular processes for the preparation of these compounds are described further in the accompanying examples.

In the description of the synthetic methods described herein and in any referenced synthetic methods that are used to prepare the starting materials, it is to be understood that all proposed reaction conditions, including choice of solvent, reaction atmosphere, reaction temperature, duration of the experiment and workup procedures, can be selected by a person skilled in the art.

It is understood by one skilled in the art of organic synthesis that the functionality present on various portions of the molecule must be compatible with the reagents and reaction conditions utilised.

It will be appreciated that during the synthesis of the compounds of the invention in the processes defined herein, or during the synthesis of certain starting materials, it may be desirable to protect certain substituent groups to prevent their undesired reaction. The skilled chemist will appreciate when such protection is required, and how such protecting groups may be put in place, and later removed.

For examples of protecting groups see one of the many general texts on the subject, for example, 'Protective Groups in Organic Synthesis' by Theodora Green (publisher: John Wiley & Sons). Protecting groups may be removed by any convenient method described in the literature or known to the skilled chemist as appropriate for the removal of the protecting group in question, such methods being chosen so as to effect removal of the protecting group with the minimum disturbance of groups elsewhere in the molecule.

Thus, if reactants include, for example, groups such as amino, carboxy or hydroxy it may be desirable to protect the group in some of the reactions mentioned herein.

By way of example, a suitable protecting group for an amino or alkylamino group is, for example, an acyl group, for example an alkanoyl group such as acetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed by, for example, hydrolysis with a suitable base such as an alkali metal hydroxide, for example lithium or sodium hydroxide. Alternatively an acyl group such as a tert-butoxycarbonyl group may be removed, for example, by treatment with a suitable acid as hydrochloric, sulfuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium, sodium hydroxide or ammonia. Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, for example an organic acid such as trifluoroacetic acid, or for example a benzyl group which may be removed, for example, by hydrogenation over a catalyst such as palladium-on-carbon.

Resins may also be used as a protecting group.

The methodology employed to synthesise a compound of general formula (1) will vary depending on the nature of $R_1$, $R_2$, $R_3$, $R_4$, L, Z, hapten and any substituent groups associated therewith. Suitable processes for their preparation are described further in the accompanying Examples.

In certain embodiments, the compounds of the present invention (i.e. the compounds of general formula (1)) are prepared by one of the two different synthetic approaches that follow. In the first approach a reaction of an SBB analogue compound of the general structure (2A) or (3A) shown below:

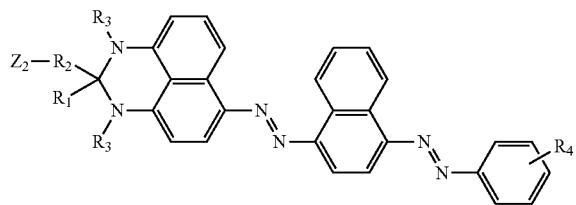

(2A)

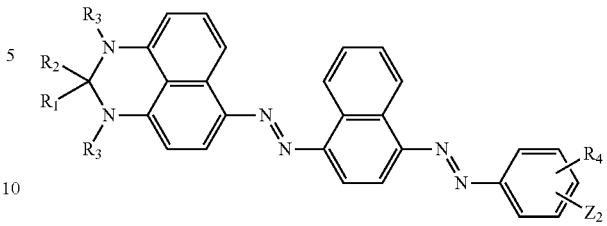

(3A)

wherein:
$R_1$ and $R_2$ are each independently selected from:
i) hydrogen; with the proviso that $R_2$ is not hydrogen in general structure (2A) above and only one of $R_1$ and $R_2$ can be hydrogen in general structure (3A) above.
ii) an optionally substituted (1-10C)alkyl group;
iii) an optionally substituted aryl group;
iv) an optionally substituted (1-10C)alkyl-aryl group;
v) an optionally substituted aryl-(1-10C)alkyl group; or
vi) $R_1$ and $R_2$ are linked so as to form part of a spiranic cycloalkane group, selected from cyclopentyl, cyclohexyl, cycloheptyl, cyclooctyl, cyclononyl or adamantanyl;

$R_3$ is hydrogen or (1-10C)alkyl group;
$R_4$ is hydrogen, or one or more of the following substituents:
i) a halogen selected from F, Cl, Br and I;
ii) $NO_2$;
iii) $CF_3$;
iv) $SCH_3$;
v) an optionally substituted (1-5C)alkyl group;
vi) a (1-10C)alkoxy group which optionally comprises one or more heteroatoms;

$Z_2$ is selected from —OH, —$NH_2$, —O$(CH_2)_n CH_2 OH$, —$(CH_2)_q OH$ or —COOH, wherein n is an integer selected from 1 to 9, and wherein q is an integer selected from 1 to 4;

with a hapten selected from biotin, digoxigenin, 2,4-dinitrophenol, or fluorescein, is performed, resulting into the chemical compounds of the general formula (1).

This reaction is optionally carried out in the presence of a catalyst and/or a coupling agent. Suitably, the reaction is carried out in the presence of both a catalyst and a coupling agent.

Suitably, the coupling agent is a peptide or ester coupling agent. More suitably, the coupling agent is a carbodimide based coupling reagent. Yet more suitably, the coupling reagent is selected from N,N'-dicyclohexylcarbodiimide (DCC), N,N'-diisopropylcarbodiimide (DIC), 1-ethyl-3-(3-dimethylaminopropyl)carbodiimide (EDCI), N-cyclohexyl-N'-isopropylcarbodiimide (CIC) or N,N'-dicyclopentylcarbodiimide (CPC). Even more suitably, the coupling reagent is selected from N,N'-dicyclohexylcarbodiimide (DCC), N,N'-diisopropylcarbodiimide (DIC) or 1-ethyl-3-(3-dimethylaminopropyl)carbodiimide (EDCI). Most suitably, the coupling reagent is N,N'-dicyclohexylcarbodiimide (DCC).

It will be understood that the catalysts is an agent which may be used together with the coupling reagent defined hereinabove, to further enhance reactivity between the compounds of Formula 2A or 3A and the hapten (more specifically the carboxy functionality of the hapten). Suitably, the catalyst is selected from hydroxybenzotriazole (HOBt), N-hydroxy 2-phenyl benzimidazole (HOBI), 1-hydroxy-7-azabenzotriazole (HOAt), N-hydroxysuccinimide (NHS), N-hydroxysulfosuccinimide (Sulfo-NHS), 4-dimethylaminopyridine (DMAP) or ethyl cyano(hydroxyimino)acetate (Oxyma Pure®), More suitably, the catalyst is selected from hydroxybenzotriazole (HOBt), N-hydroxy 2-phenyl benzimidazole (HOBI), N-hydroxysuccinimide (NHS) or 4-dimethylaminopyridine (DMAP). Most suitably, the catalyst is 4-dimethylaminopyridine (DMAP).

In the second approach, a reaction of a compound of formula A, shown below:

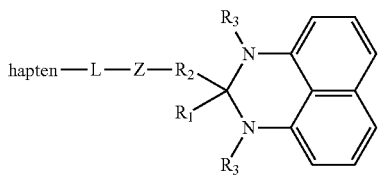
(A)

wherein:
  hapten is selected from biotin, digoxigenin, 2,4-dinitrophenol, or fluorescein;
  L is an ester bond or an amide bond or an ether bond; more preferably L is an ester bond;
  $R_1$ and $R_2$ are each independently selected from:
    i) hydrogen; with the proviso that $R_2$ is not hydrogen.
    ii) an optionally substituted (1-10C)alkyl group;
    iii) an optionally substituted aryl group;
    iv) an optionally substituted (1-10C)alkyl-aryl group;
    v) an optionally substituted aryl-(1-10C)alkyl group; or
    vi) $R_1$ and $R_2$ are linked so as to form part of a spiranic cycloalkane group, selected from cyclopentyl, cyclohexyl, cycloheptyl, cyclooctyl, cyclononyl or adamantanyl;
  $R_3$ is hydrogen or (1-10C)alkyl group;
with a compound of formula X, shown below:

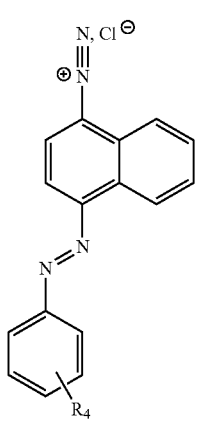
(X)

wherein $R_4$ is hydrogen, or one or more of the following substituents:
  i) a halogen selected from F, Cl, Br and I;
  ii) $NO_2$;
  iii) $CF_3$;
  iv) $SCH_3$;
  v) an optionally substituted (1-5C)alkyl group;
  vi) a (1-10C)alkoxy group which optionally comprises one or more heteroatoms;
is performed, resulting into the synthesis of the compounds of the general structure (1).

More specifically, concerning the synthesis of the compounds of the general structures (5) to (10), these can be prepared according to the synthetic methodology shown in Schemes 3.1 up to 3.10.

Thus, for the synthesis of compounds that belong to the general formula (5), the two different synthetic procedures described above can be followed. In the first method, 8-amino-1-naphthylamine can be used as starting material and upon reaction with the substituted hydroxy ketones will be converted to modified 2,2-substituted-2,3-dihydro-1H-perimidines (Scheme 3.1) [Zhang & Zhang, Synth Comm 2007; Farrand L D et al Merck Patent GMBH WO 2014/111112 A1]. The bis alkyl substituted perimidines at nitrogens 1 and 3 can be prepared upon treatment with the corresponding alkyl bromide under basic conditions. These compounds can be used as substrates for the electrophilic addition of suitably substituted diazotized amino-derivatives resulting from the coupling of diazotized substituted aniline with 1-naphthylamine. The electrophilic aromatic substitution affords two regio-isomers (6- or 4-substituted derivatives) that are first separated and then the desired 6-substituted isomer is inserted into the esterification reaction with biotin [da Costa et al, ACS Med Chem Lett 2012; Abell, et al. Patent WO 2013/040647 A1]. The esterification reaction can be effected through an appropriate esterification method, for example with the use of dicyclohexylcarbodiimide (DCC) and 4-dimethylaminopyridine (DMAP), or through the acyl chloride or acyl bromide of biotin which can be prepared after reacting biotin with a chlorinating or brominating agent, for example thionyl chloride or thionyl bromide respectively, or by reaction of biotin and the hydroxy-SBB derivatives with the use of a catalyst, for example an acid, in a suitable solvent for example toluene. In the second method, the bis alkyl substituted perimidines can be first esterified with biotin, and then the resulting esters will be used as substrates for the azo coupling reaction with the substituted phenylazonaphthylamines (Scheme 3.2).

Scheme 3.1 Synthesis of compounds of the general formula (5).

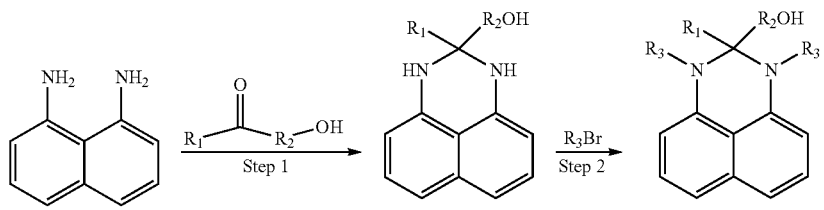

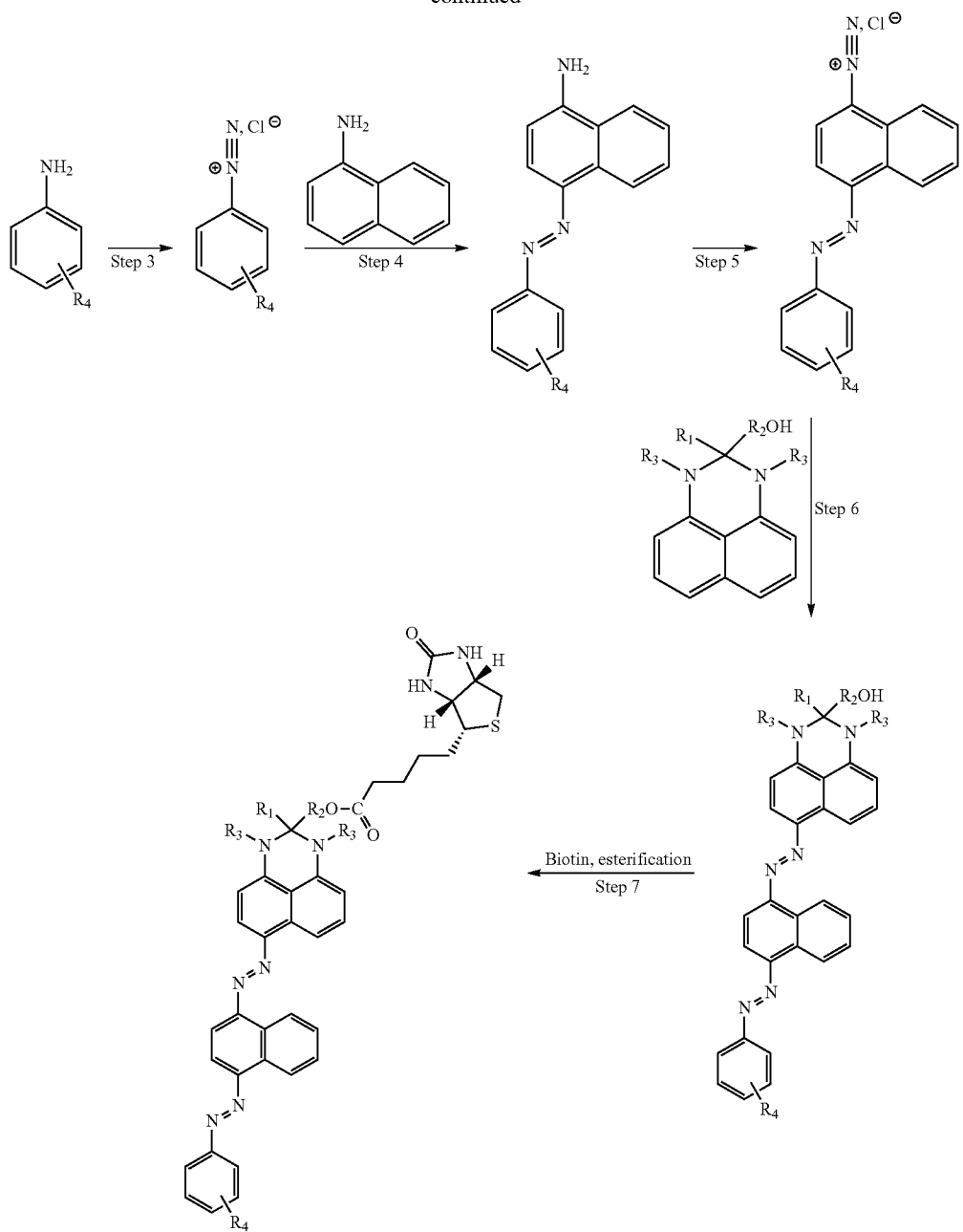
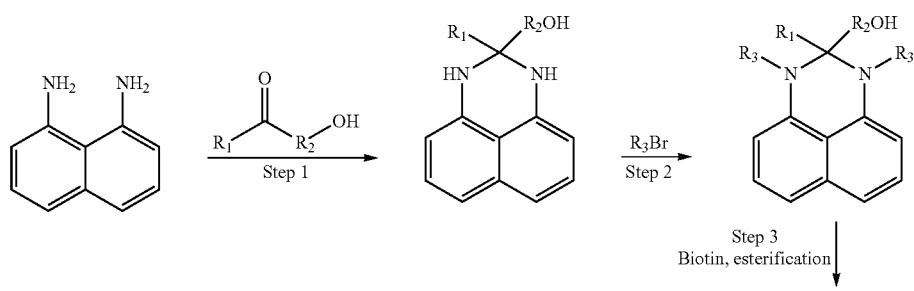
Scheme 3.2 Alternative synthetic procedure for the synthesis of compounds of the general formula (5). The esterification with biotin takes place at an earlier stage and the azo-coupling reaction with phenyldiazonaphthylamine is the final step.

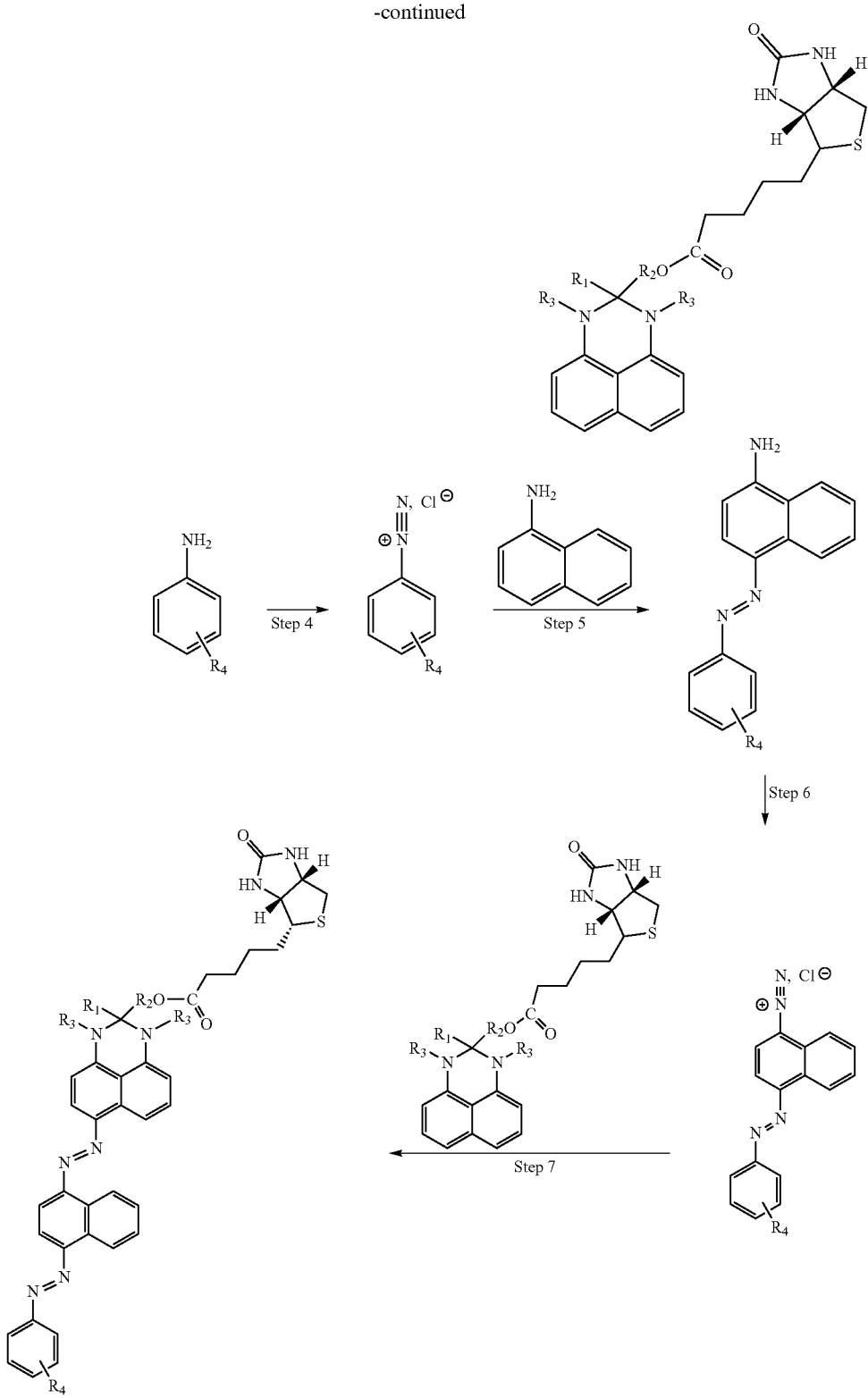

For the synthesis of compounds that belong to the general formula (6), the two aforementioned synthetic procedures can also be applied. Thus, in the first approach 8-amino-1-naphthylamine reacts with the substituted 4-hydroxybenzaldehyde resulting into 2-aryl substituted-2, 3-dihydro-1H- perimidines (Scheme 3.3). A hydroxyalkyl chain can be attached to the phenolic hydroxyl group via reaction with a hydroxyalkyl bromide under basic conditions. Subsequent reaction with phenylazonaphthylamine and esterification leads to the target compounds of the general formula (6).

With an analogous synthetic procedure, and starting from substituted 3-hydroxybenzaldehydes, compounds that have the biotin attached to the position 3 of the aryl group of the 2-aryl substituted-2, 3-dihydro-1H-perimidines can be prepared. When the second approach is used, the esterification with biotin takes place at the stage of the 2-aryl substituted-2, 3-dihydro-1H-perimidine and then the azo-coupling reaction with the phenylazonaphthylamine is the final step of the procedure (Scheme 3.4).

Scheme 3.3 Synthesis of compounds of the general formula (6).

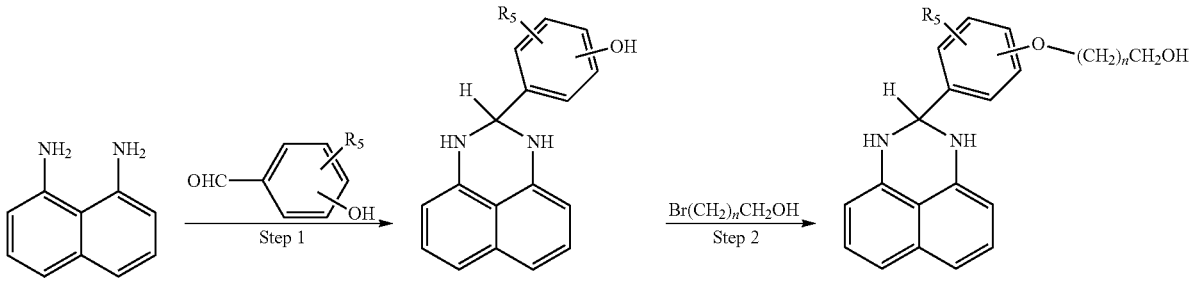

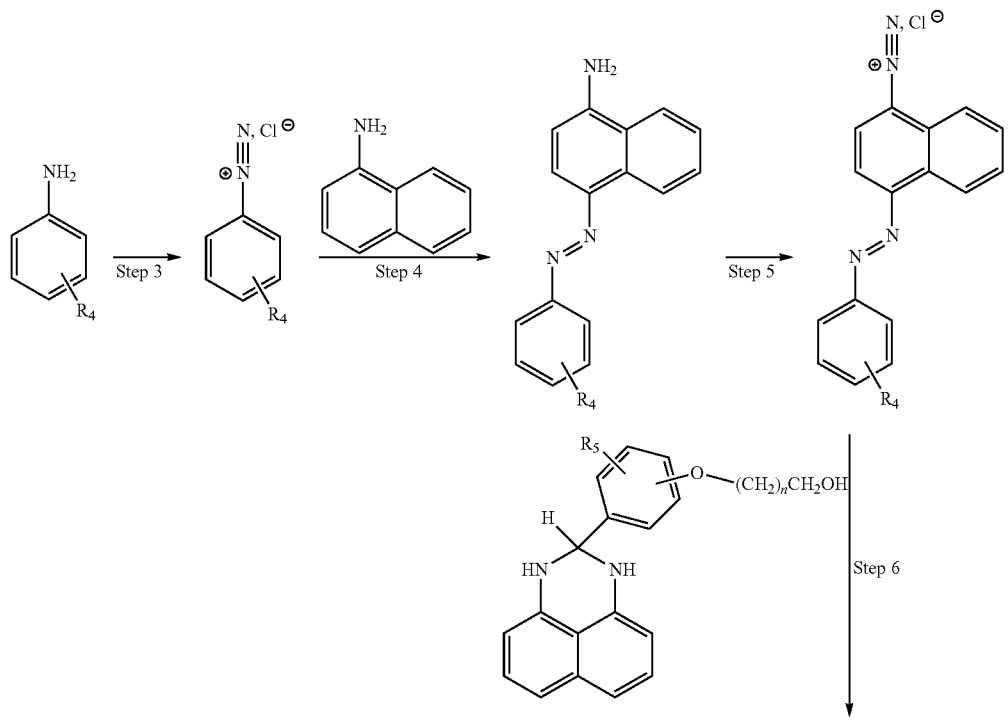

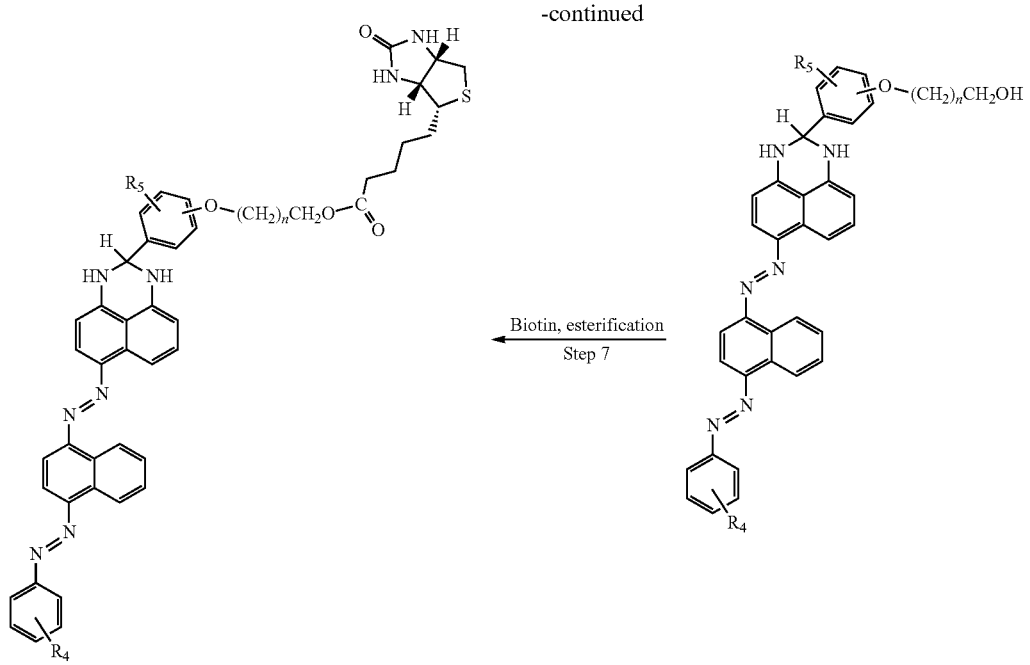
Scheme 3.4 Alternative synthetic procedure for the synthesis of compounds of the general formula (6). The esterification with biotin takes place at an earlier stage and the azo-coupling reaction with phenyldiazonaphthylamine is the final step.
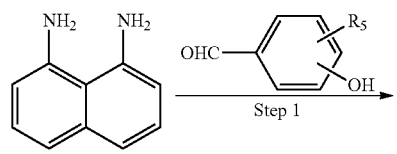
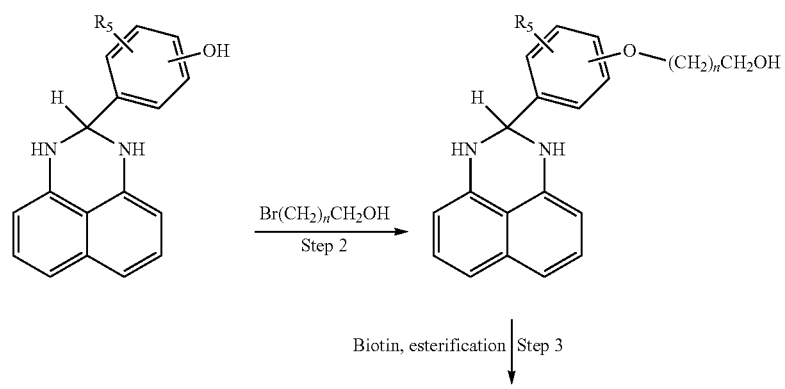

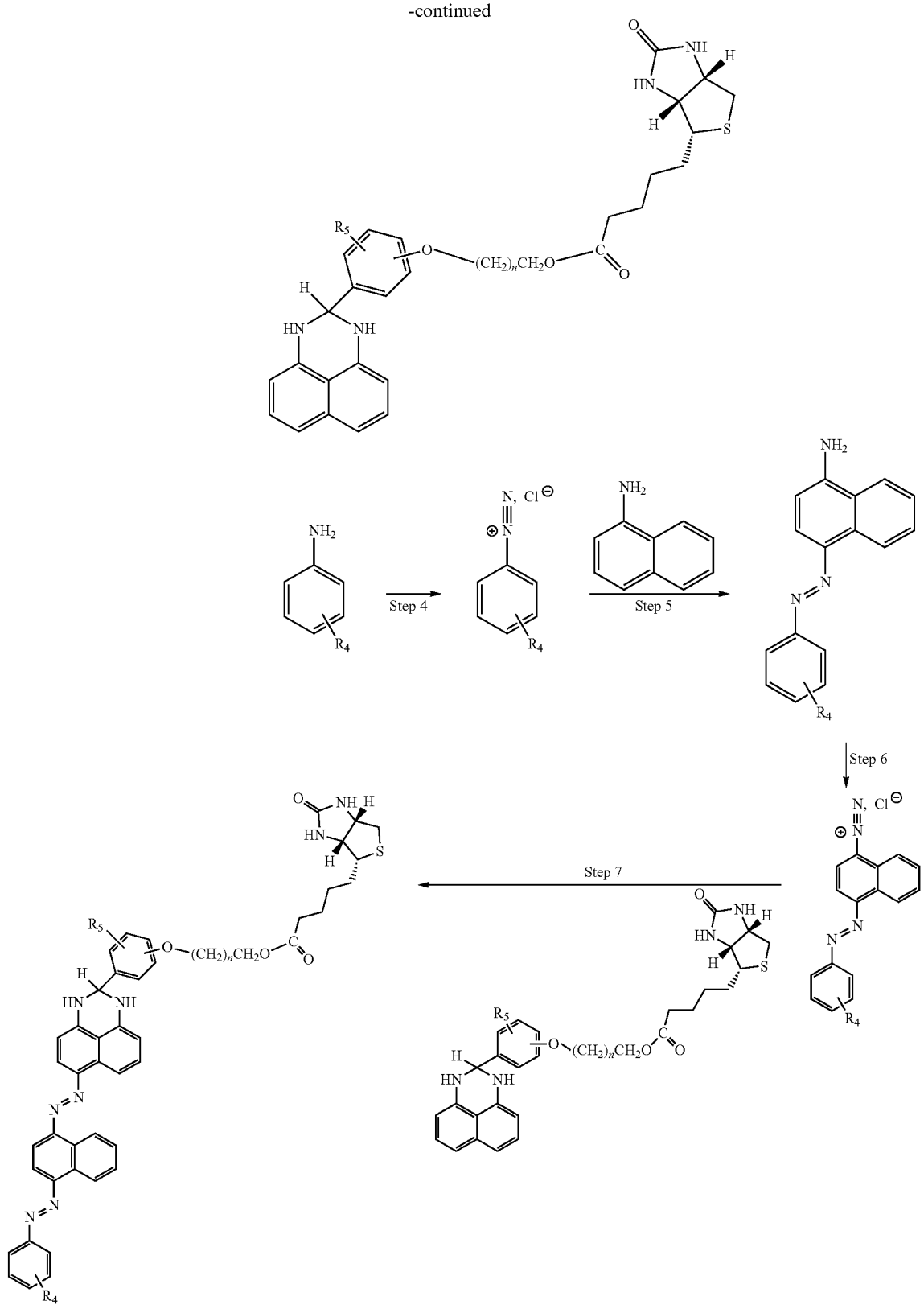
For the synthesis of compounds that belong to the general formula (7), in the first step 8-amino-1-naphthylamine reacts with the substituted ketone, and then alkyl chain can be inserted to nitrogens 1 and 3 of perimidine (Scheme 3.5). At the same time, the substituted 4-amino phenol is coupled to naphthylamine through diazotation reaction, followed by a second diazotation reaction for coupling of the former with the substituted perimidine. Finally, an esterification reaction takes place for the preparation of target compounds.

Concerning the analogues of the general formula (7) that possess an alkoxy chain between the biotin and the aniline ring of the chromophore system, these can be synthesized from the corresponding substituted 4-nitrophenols upon treatment with hydroxyalkyl bromides under basic conditions and subsequent reduction of the nitro group (Scheme 3.6).

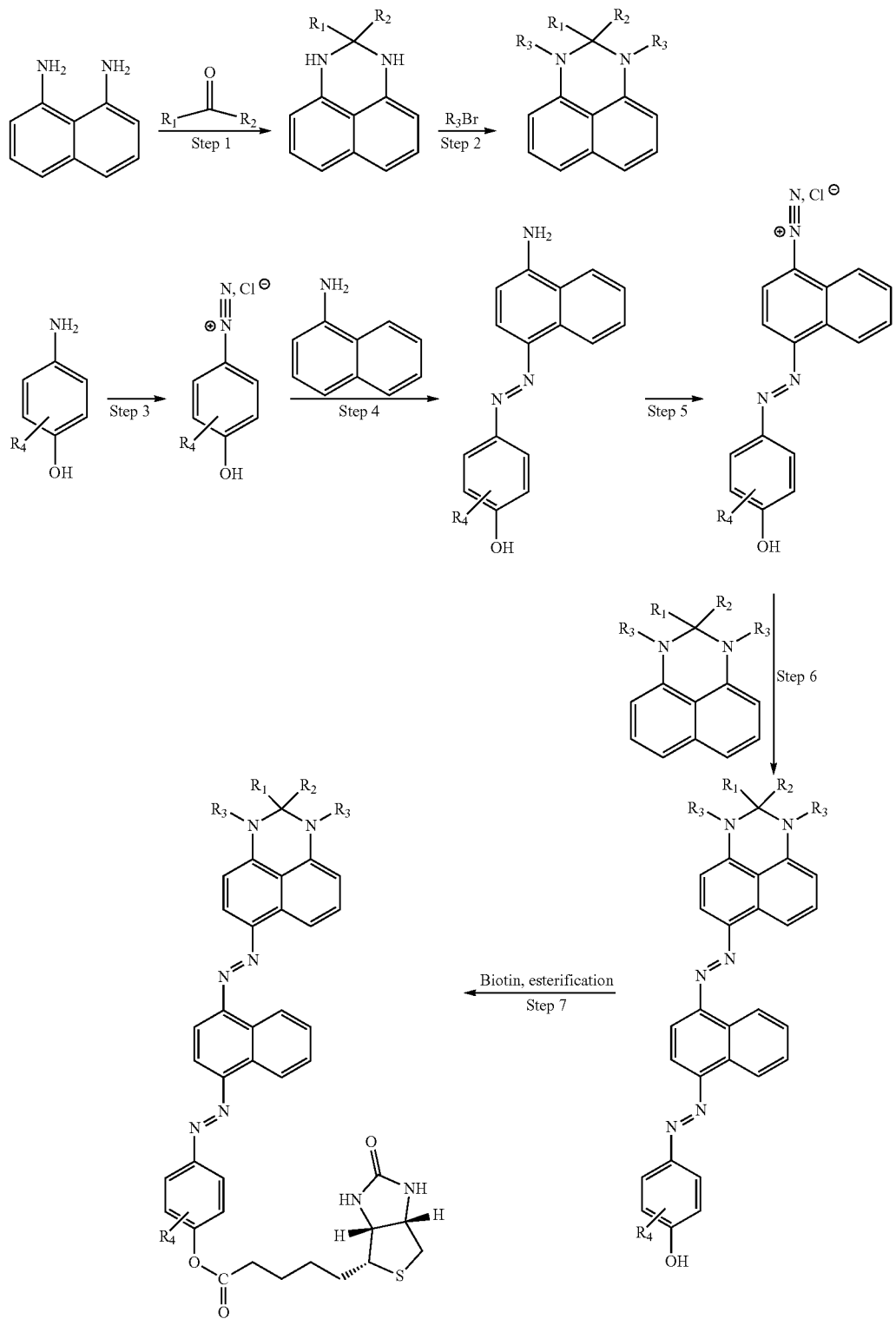

Scheme 3.5 Synthesis of compounds of the general formula (7).

Scheme 3.6 Synthesis of compounds of the general formula (7), that possess an alkoxy chain between the biotin and the aniline ring of the chromophore system.
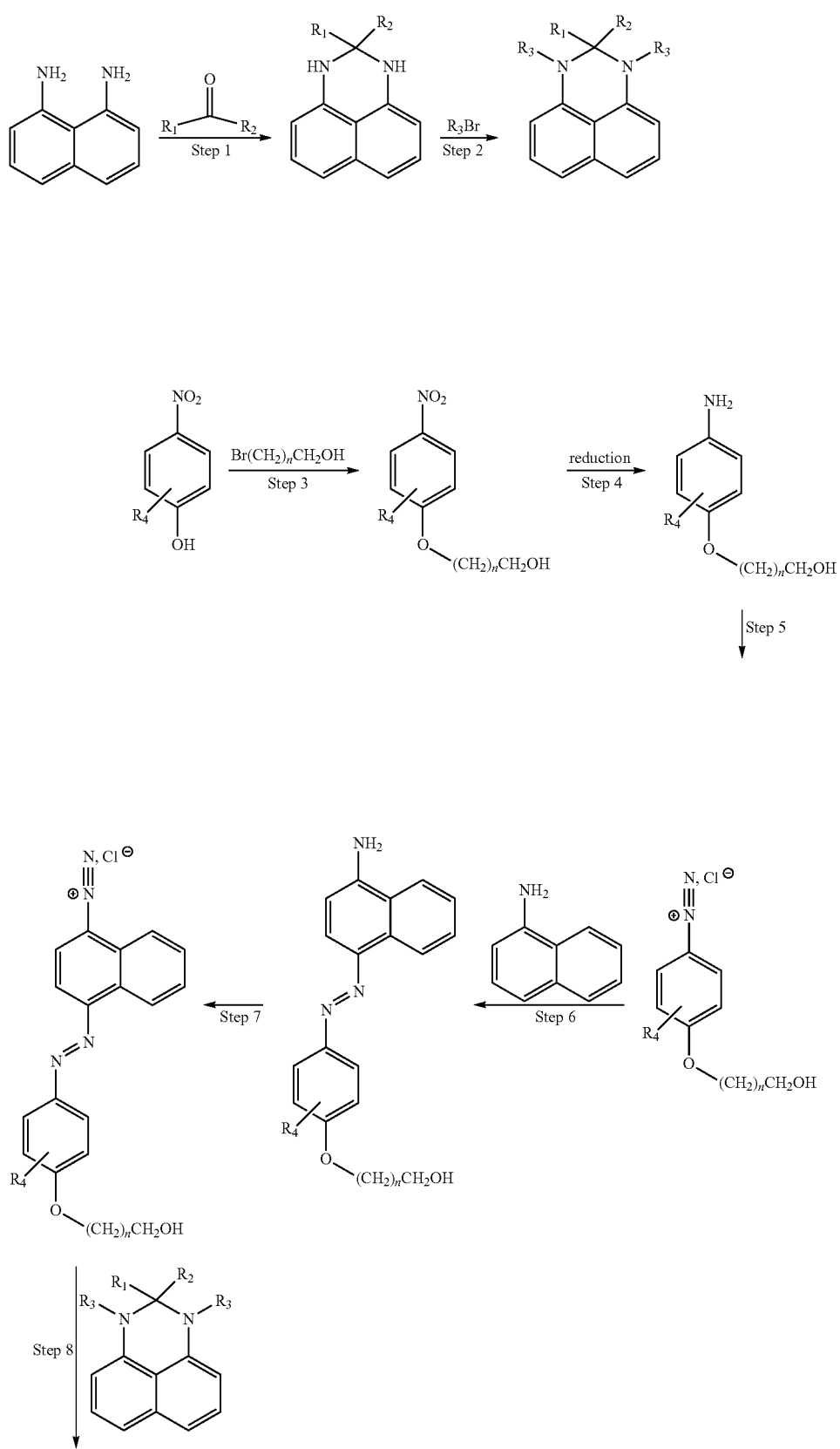

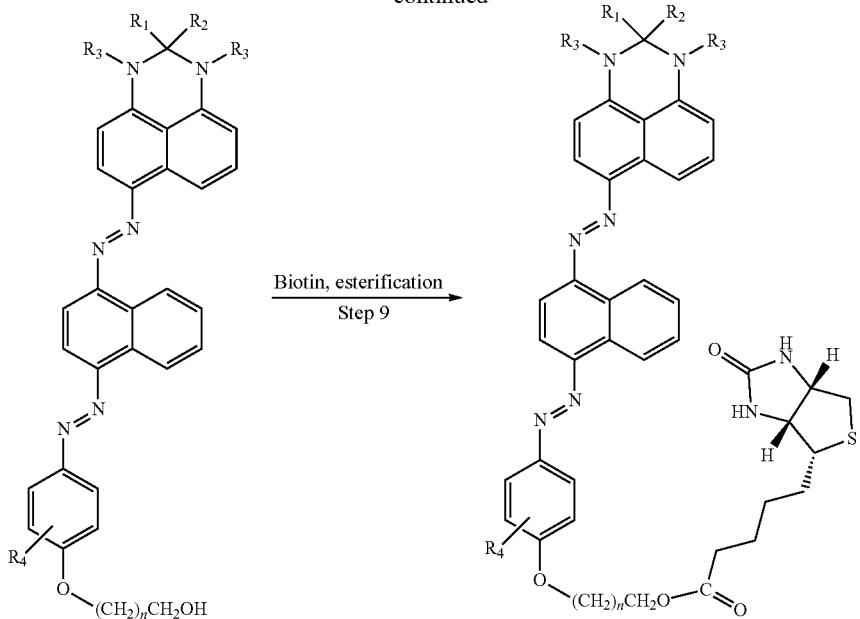

The synthesis of target compounds of the general formula (8) can be achieved by an analogous synthetic approach to the one that described above for the synthesis of compounds of general formula (7), by using the substituted 3-aminophenols as starting materials (Scheme 3.7). Concerning the analogues of the general formula (8) that possess an alkoxy chain between the biotin and the aniline ring of the chromophore system, these can be synthesized from the corresponding substituted 3-nitrophenols upon treatment with hydroxyalkyl bromides under basic conditions and subsequent reduction of the nitro group (Scheme 3.8).

Scheme 3.7 Synthesis of compounds of the general formula (8).

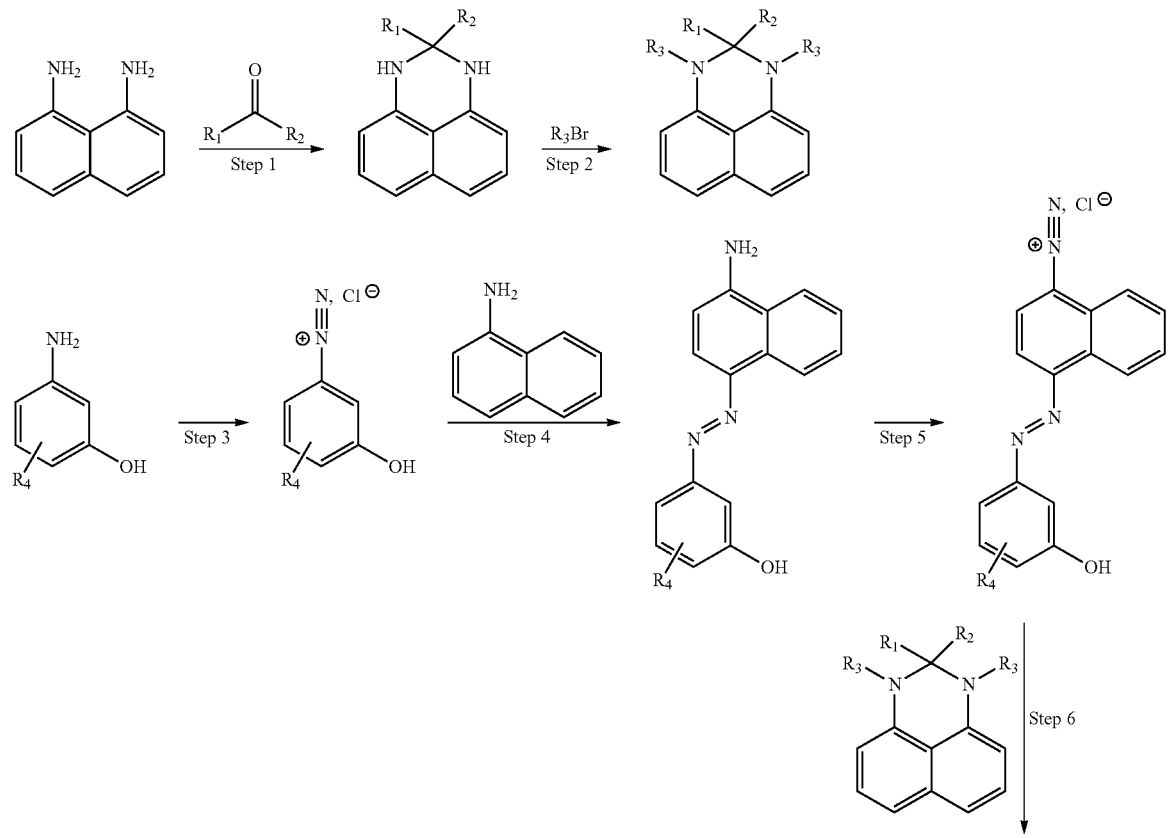

-continued
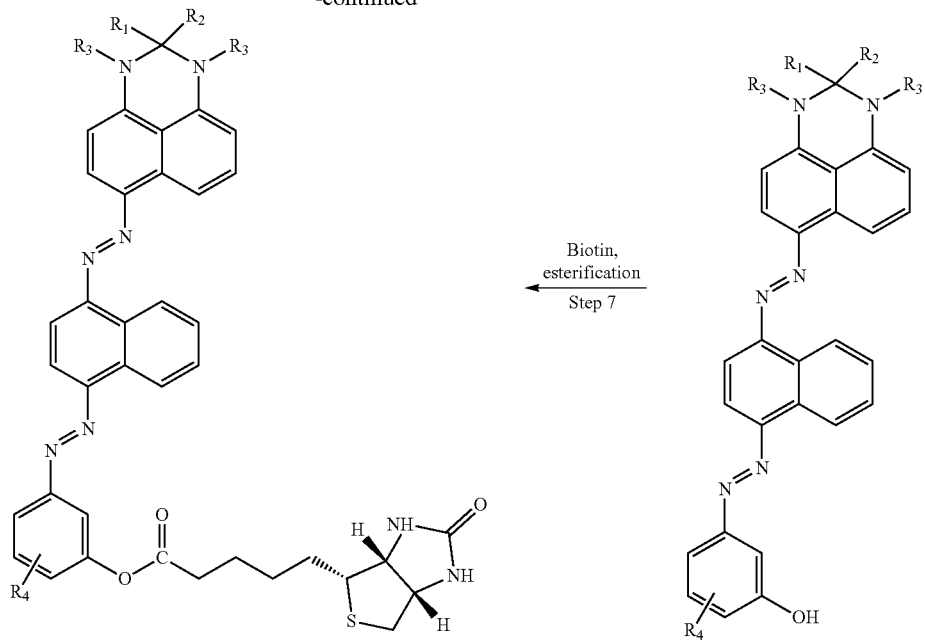
Scheme 3.8 Synthesis of compounds of the general formula (8), that possess an alkoxy chain between the biotin and the aniline ring of the chromophore system.
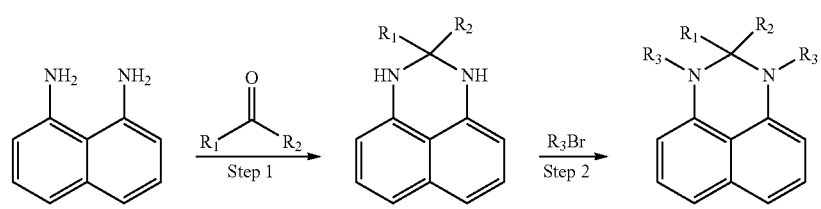
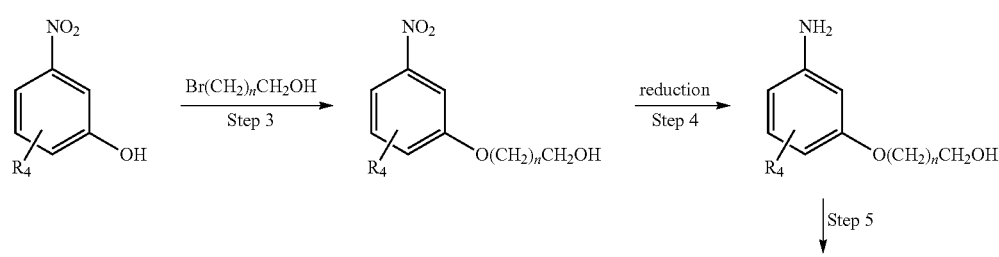

-continued

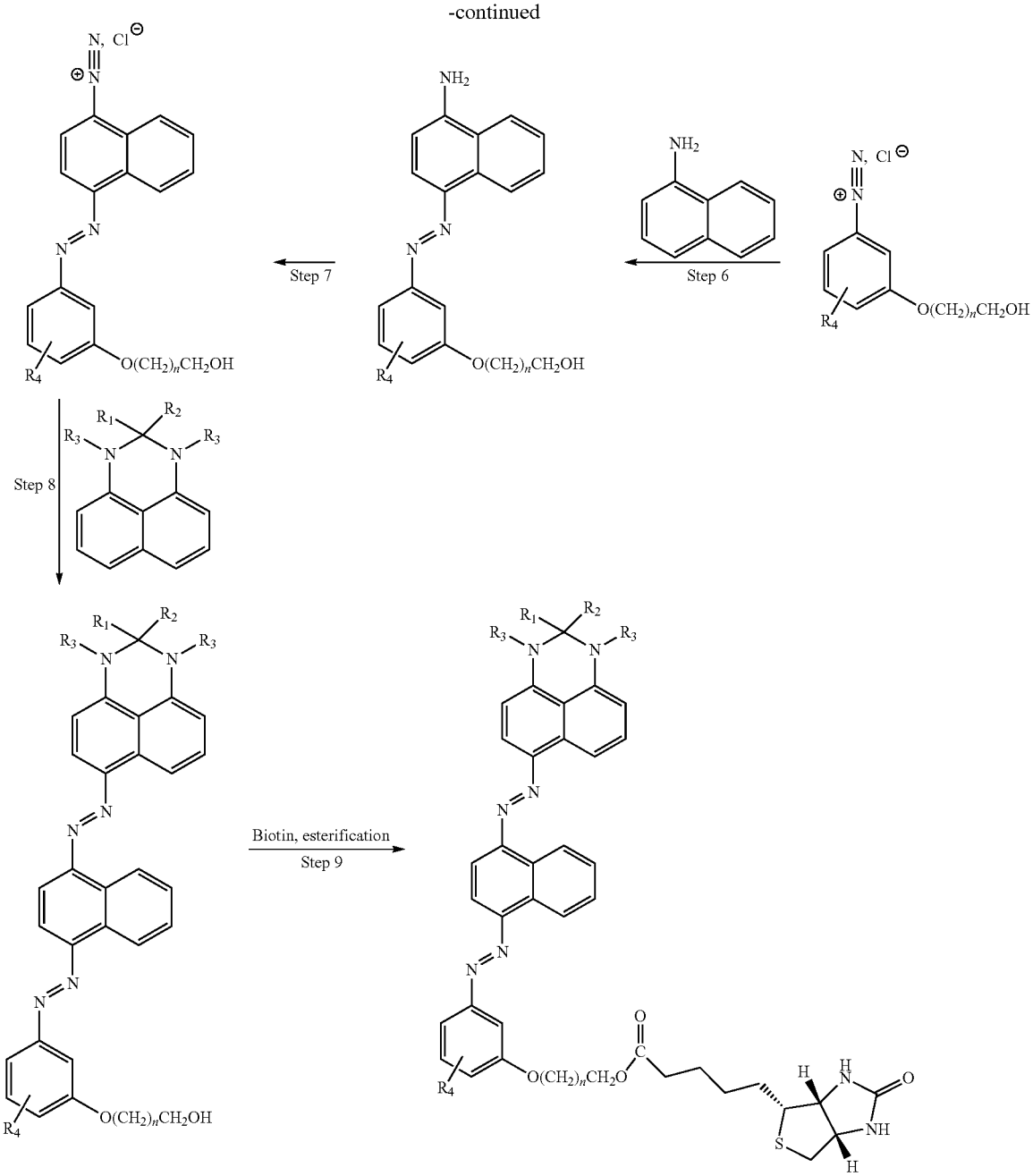

For the synthesis of target compounds that belong to the general formulas (9) and (10), the substituted para-amino phenyl alkyl alcohols or the substituted meta-amino phenyl alkyl alcohols can be used as starting materials (Schemes 3.9 and 3.10, respectively), and through the aforementioned reactions lead to the final products.

Scheme 3.9 Synthesis of compounds of the general formula (9).

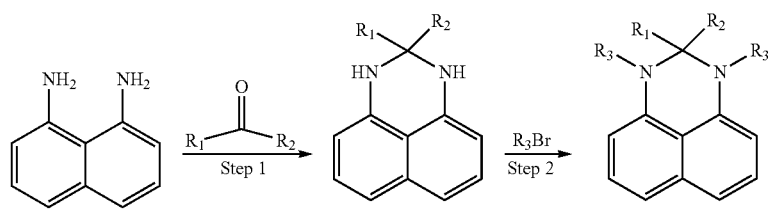

-continued
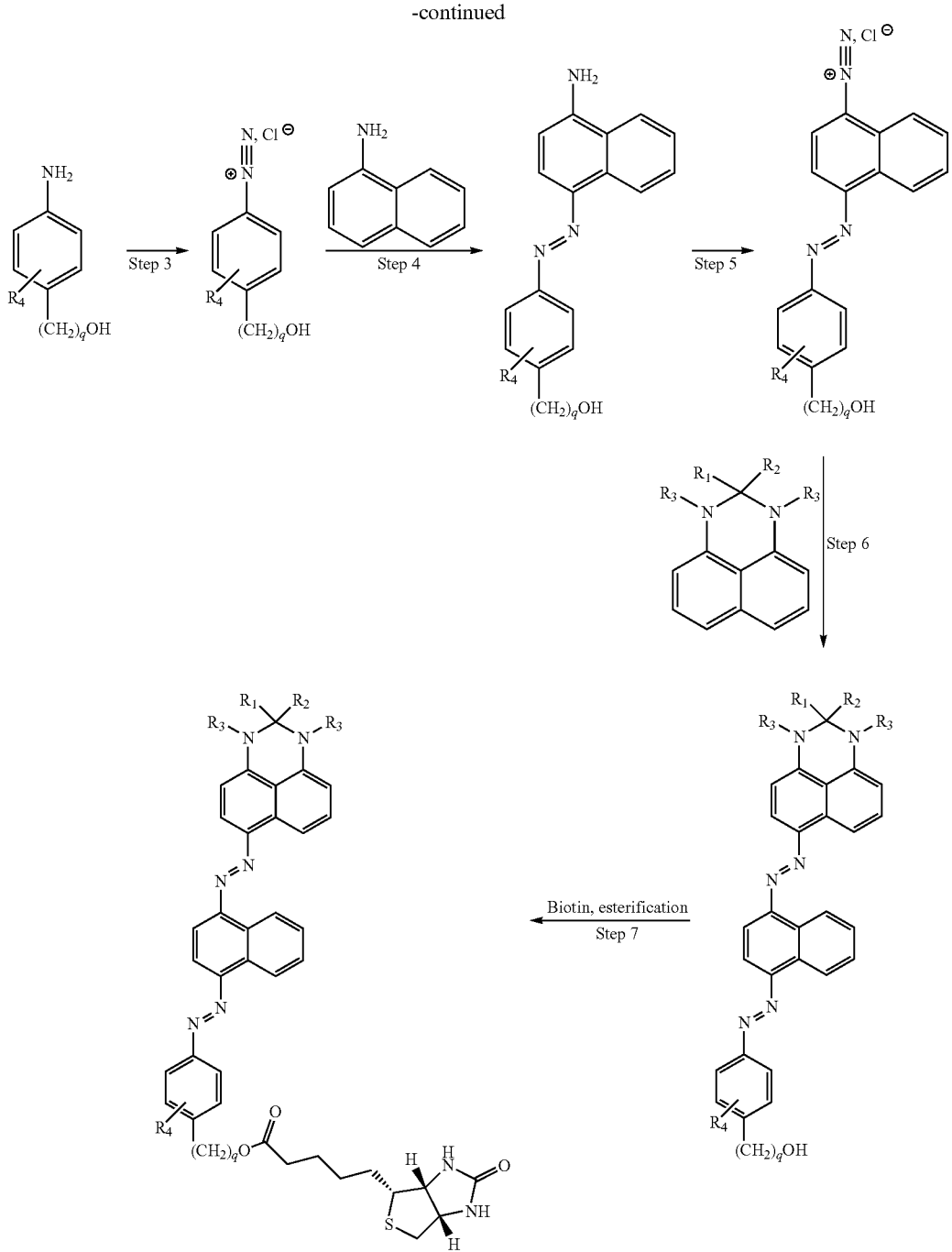
Scheme 3.10 Synthesis of compounds of the general formula (10).
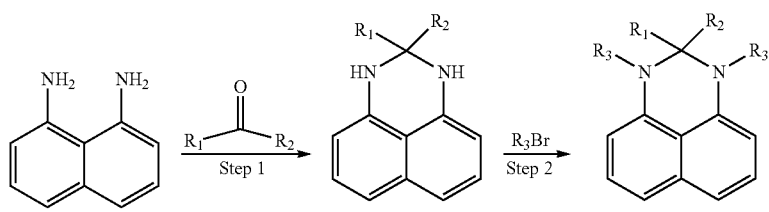

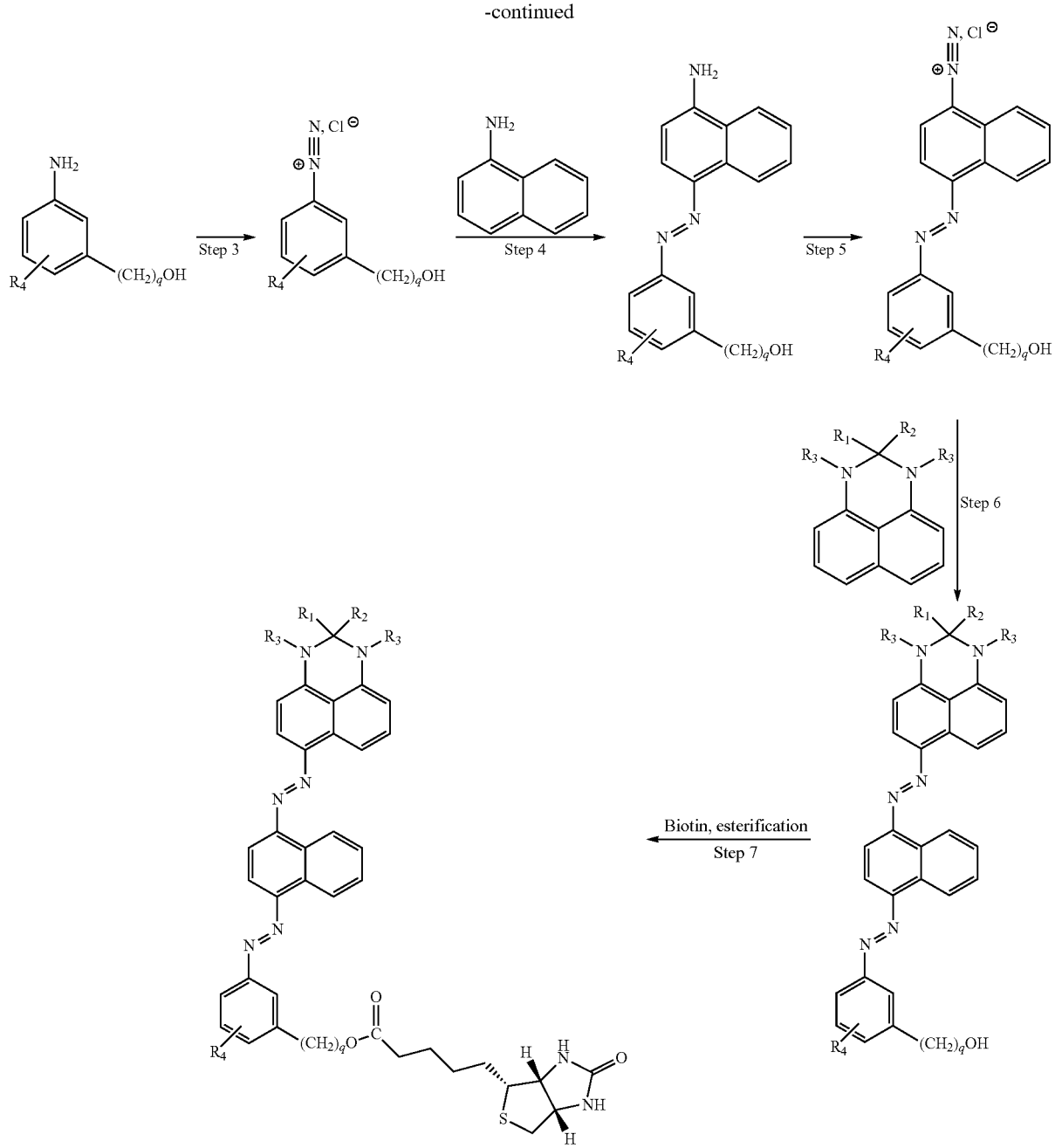

Uses and Applications

The present invention provides compounds that are capable of associating with lipofuscin and thus capable of application in the detection of senescent cells.

The present invention provides a use of a compound, as described hereinabove, for the detection of senescent cells.

Thus, in one aspect, the present invention provides the use of a compound of general formula (1) (or any one of compounds of sub-formulae (5) to (10)) for the detection of senescent cells.

The present invention also provides a use of a compound, as described hereinabove, for the detection of single senescent cells or senescent cells in mixed cell populations through reacting with lipofuscin in a similar manner to the Sudan Black B histochemical dye.

Moreover, the present invention also provides a use of a compound, as described hereinabove, for the detection of senescent cells in: i) tissues of animal origin, ranging from invertebrates to mammals, including humans; ii) single animal cells either derived from the above tissues or in suspension; or iii) plant tissues.

Furthermore, the present invention provides a use of a compound, as described hereinabove, for the detection of senescent cells in biological samples, characterized in that the biological samples are in a fresh or preserved state.

Thus, it will be appreciated that the described chemical compounds of the present invention can find applications in the following fields: biomedical research, clinical/health care, cosmetics, male and female infertility/subfertillity, animal/plant farming and the food industry. Specifically they can be used for routine detection of senescent cells by applying conventional immunohistochemical procedures in: i) tissues of animal origin, ranging from invertebrates to mammals, including humans that can be normal or of pathologic condition, ii) single animal cells either derived from the above tissues or in suspensions, body fluids and cell scrapes/smears, for example blood samples, urine specimens or cervical smears, or in laboratory culture, and iii) in tissues or cells of plant origin. All these biological materials can be either in a fresh state or preserved by physical means, such as freezing, or by chemical treatment, such as immersion in formaldehyde, including if necessary, embedding in inert supportive material, like paraffin. Notably, the vast majority of sample biobanks available in research and diagnostic laboratories, hospitals, private clinics etc, are in the later form.

Specific embodiments of this invention are described in detail in the following examples. These examples are intended to be illustrative and the claims are not limited to the materials, reaction conditions or process parameters that are going to be presented in these embodiments.

Methods and Kits

The present invention also provides a method for detecting senescence, the method comprising contacting (i.e. reacting) a compound, as defined hereinabove, with a sample of single or mixed cells, in the presence of lipofuscin.

In an embodiment, the sample of single or mixed cells is from a tissue sample of animal origin. It will be appreciated that the sample of single or mixed cells may be from normal tissue samples of animal origin or from tissue samples of a pathologic condition of animal origin.

In another embodiment, the sample of single or mixed cells is from a tissue sample of human origin. It will again be appreciated that the sample of single or mixed cells may be from normal tissue samples of human origin or from tissue samples of a pathologic condition of human origin.

In yet another embodiment, the sample of single or mixed cells is from a tissue sample of plant origin.

The compounds of the present invention described herein are compatible with senescent cell detection in a wide range of in vivo and in vitro biosamples. Specifically these samples can be:

1) Tissues of animal origin: senescent cells that accumulate lipofuscin can be detected in tissues (in situ) from lower (evolutionary) invertebrates up to mammals, including humans, using any of the compounds described herein.

2) Single animal cells: either derived from the above tissues using tissue disaggregation methods or that are in suspension, for example body fluids such as blood cells, or grown in laboratory culture can be evaluated for the senescence state by using any of the compounds described herein.

3) Plant origin: senescent cells that accumulate lipofuscin can be detected in such tissues, too.

4) The biological materials described at points 1), 2) and 3) can be either in:
   i) a fresh state; or
   ii) preserved (fixed), to avoid decomposition, by physical means such as freezing, or by chemical treatment, such as immersion in formaldehyde, including if necessary, embedding in inert supportive material, like paraffin.

Notably, the vast majority of sample biobanks available in hospitals, research institutions, private clinics, etc., are in the form of fixed tissues that are usually embedded in paraffin to facilitate thin-sectioning for further analyses.

The current invention is based on the ability of these new compounds to reveal the presence of senescent cells in vivo and in vitro, upon reacting with lipofuscin, and to distinguish them from non-senescent ones.

In one embodiment of the method of this invention fixed tissues section [e.g. using formaldehyde, paraformaldehyde or glutaraldehyde diluted in TBS (Tris-buffered saline) or PBS (Phosphate-buffered saline)] or fresh tissue sections or cell spreads are processed to reveal senescent cells as follows:
  a. Deparaffinization for 5 min at room temperature in xylene (if sections are obtained from paraffin embedded blocks) followed by gradual rehydration of biopsy material, usually tissues, in solutions of descending concentration of ethanol (100%, 80%, 70%, 50% v/v) and finally in TBS (Tris-buffered saline) or PBS (Phosphate-buffered saline) solution.
  b. For fresh tissue sections (cryosections) or cell spreads, 5-10 min incubation in 70% ice-cold ethanol or methanol (v/v) solution should be used instead of the above step.
  c. Blocking of non-specific endogenous activity in the biopsy material, such as blocking of peroxidase activity with the use of 3% $H_2O_2$ for 10 min in case an HRP detection system is employed.
  d. Gradual dehydration of biopsy material in 50% (v/v) ethanol followed by 70% (v/v) ethanol for 5 min each step.
  e. Application of the new hapten-linked compound, preferably coupled with biotin, diluted in ethanol and filtered, on biopsy material for 10 min.
  f. Quick wash in 50% (v/v) ethanol.
  g. Transfer and wash in TBS or PBS solution.
  h. Incubation in detection system, preferably Streptavidin conjugated to horseradish peroxidase (HRP) (dilution 1/200), for ½ hr at room temperature, if biotin is the linked hapten.
  i. Quick wash in TBS or PBS solution.
  j. Signal development, such as staining with 3,3'-Diaminobenzidine (DAB) solution (dilution 1/300 in TBS) for 1 min at room temperature, if biotin is the linked hapten.
  k. Counterstain with hematoxylin or Nuclear Fast Red, followed by mounting with DPX or glycerol and sealed with a cover slip, respectively.
  l. Microscopy observation.

A further alternative of the above method can employ fluorescent conjugated antibodies against biotin, or any other hapten, to enable fluorescent detection and observation of senescent cells.

In another embodiment of the method, single cells (e.g. as spreads on microscopy coverslips) or tissues sections can be histochemically stained as follows:
  a. Cell spreads should be immersed for 5-10 min in 70% ice-cold ethanol or methanol (v/v) solution.
  b. For fresh tissue sections (cryosections) 5-10 min incubation in 70% ice-cold ethanol or methanol (v/v) solution should be used instead of the above step.
  c. Fixed tissue sections should be deparaffinized for 5 min at room temperature in xylene (if sections are obtained from paraffin embedded blocks) followed by gradual rehydration of biopsy material, usually tissues, in solutions of descending concentration of ethanol (100%, 80%, 70%, 50% v/v) and finally in TBS (Tris-buffered saline) or PBS (Phosphate-buffered saline) solution.
  d. Application of the SBB analogue or the corresponding new compound that is linked with hapten diluted in ethanol and filtered, on biopsy material for 10 min.
  e. Quick wash in 50% (v/v) ethanol.
  f. Transfer and wash in TBS or PBS solution.
  g. Counterstain with hematoxylin or Nuclear Fast Red, followed by mounting with glycerol and sealed with a cover slip.
  h. Microscopy observation.

These procedures allow for identification of senescent cells using these new SBB analogues in a similar histochemical fashion like the SBB, but with improved performance and bypassing ethanol solubility problems.

According to a further aspect of the present invention, there is provided a kit for detecting senescence and differentiating senescent cells comprising:
a. a compound of general formula 1, as defined hereinabove; and
b. one or more additional reagents required to implement a method of the present inventions, as defined hereinabove.

According to another aspect of the present invention, there is provided a kit for detecting senescence and differentiating senescent cells comprising:
a. a lyophilized compound of general formula 1, as defined hereinabove;
b. ethanol solution to dilute the lyophilized compound;
c. streptavidin-HRP conjugated solution;
d. 3,3'-diaminobenzidine; and
e. hematoxylin or Nuclear Fast Red.

Thus, the above described methods can provide the basis to develop a kit for detection of senescence for commercial exploitation. The kit can find application in the following fields: biomedical research, clinical/health care, cosmetics, male and female infertility/subfertillity, animal/plant farming and the food industry. Routine detection of senescent cells can be achieved in: i) tissues of animal origin, ranging from invertebrates to mammals, including humans, ii) single animal cells either derived from the above tissues or in suspensions, body fluids and cell scrapes/smears, for example blood samples, urine specimens or cervical smears, or in laboratory culture, and iii) in tissues or cells of plant origin. Tissues or single cells can be either from healthy or pathological conditions such as aged tissues, regenerating tissues, tumors, degenerative diseases and the like. All these biological materials can be either in a fresh or preserved state (e.g. by physical or chemical means, such as freezing or formaldehyde treatment) as well as embedded in inert supportive material, like paraffin.

EXAMPLES

The following examples serve to illustrate certain preferred embodiments and aspects of the present disclosures and are not construed as limiting the scope of the invention.
Compound Synthesis
General Information:
Melting points were determined on a Büchi apparatus and are uncorrected. $^1$H-NMR spectra and $^{13}$C-NMR spectra were recorded on a Bruker Avance 600 instrument, in deuterated solvents and were referenced to TMS (δ scale). Flash chromatography was performed on Merck silica gel 60 (0.040-0.063 mm). Analytical thin layer chromatography (TLC) was carried out on precoated (0.25 mm) Merck silica gel F-254 plates. 1-Naphthylamine and 5-hydroxy-2-pentanone were purchased from Sigma-Aldrich, while the rest of the reagents were purchased from Alfa-Aesar, and all of them were used with no further purification.

Mass spectra were recorded with a LTQ Orbitrap Discovery instrument, possessing an Ionmax ionization source. Elemental analyses were undertaken using a PerkinElmer PE 240C elemental analyzer (Norwalk, Conn., U.S.) and the measured values for C, H, and N were within ±0.4% of the theoretical values.

The use of the terms "Compound 6", "GL13" and "LG13" used in the following illustrative examples synonymously refer to (2-methyl-6-((E)-(4-((E)-phenyldiazenyl)naphthalen-1-yl)diazenyl)-2,3-dihydro-1H-perimidin-2-yl)methyl 5-((3aR,4R,6aS)-2-oxohexahydro-1H-thieno[3,4-d]imidazol-4-yl)pentanoate, which has the following structure:

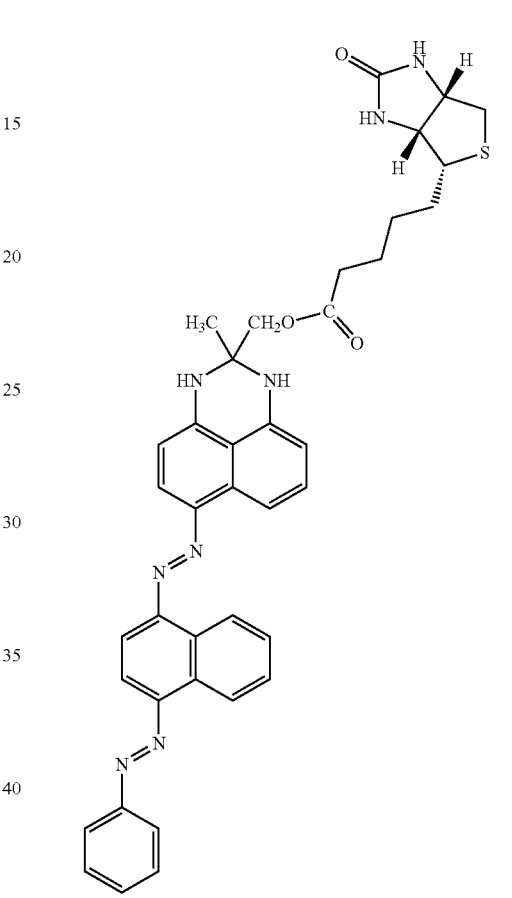

Example 1

Synthesis of (2-methyl-6-((E)-(4-((E)-phenyldiazenyl)naphthalen-1-yl)diazenyl)-2,3-dihydro-1H-perimidin-2-yl)methyl 5-((3aR,4R,6aS)-2-oxohexahydro-1H-thieno[3,4-d]imidazol-4-yl)pentanoate by Method A (Scheme 3.11)

Scheme 3.11. Synthesis of (2-methyl-6-((E)-(4-((E)-phenyldiazenyl)naphthalen-1-yl)diazenyl)-2,3-dihydro-1H-perimidin-2-yl)methyl 5-((3aR,4R,6aS)-2-oxohexahydro-1H-thieno[3,4-d]imidazol-4-yl)pentanoate by method A.

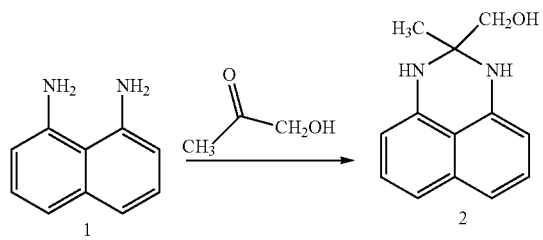

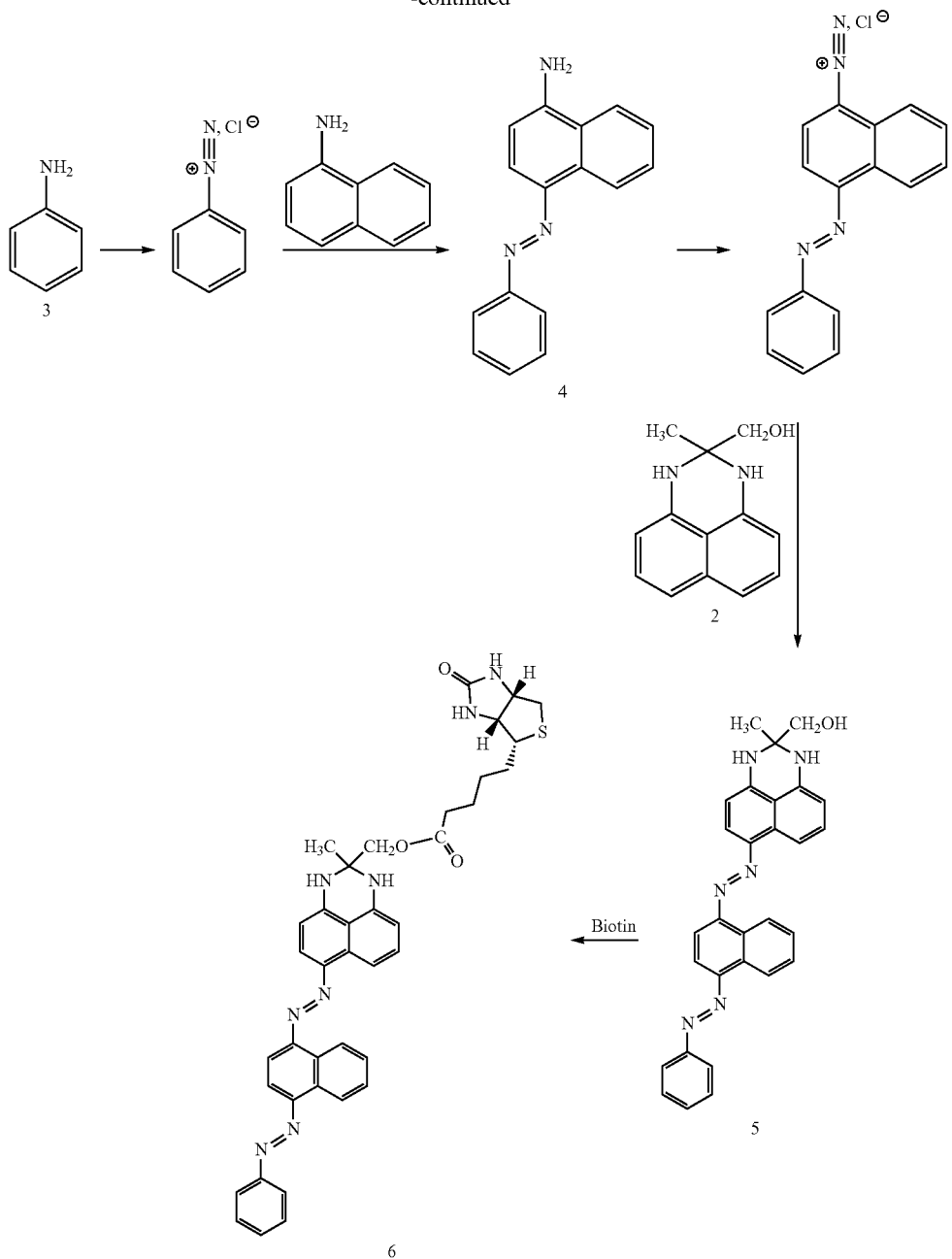

Step 1: Synthesis of (2-methyl-2,3-dihydro-1H-perimidin-2-yl)methanol (2)

1,8-Diaminonaphthalene (1, 4.3 g, 27.18 mmol) was added in a flask containing 5 ml (72.89 mmol) of hydroxyacetone and the resulting mixture was heated at 70° C. for 3 hrs. Upon completion of reaction (checked by TLC), the mixture was allowed to reach room temperature and then it was diluted with 100 ml of water, followed by extraction with $CH_2Cl_2$ (3×80 ml). Combined organic layers were washed with 200 ml of $H_2O$ and finally with 150 ml of a saturated aqueous solution of NaCl. Organic layer was dried over sodium sulfate and evaporated under reduced pressure, to provide 5.2 g of 2, as a beige solid, which was used to the next step without further purification. Yield 89%. M.p. 126-7° C. $^1$H-NMR (600 MHz, $CDCl_3$) δ 1.46 (s, 3H), 3.62 (s, 2H), 3.60-3.80 (brs, 2H, $D_2O$ exch.), 6.57 (d, 2H, J=7.2 Hz), 7.20 (d, 2H, J=7.5 Hz), 7.24 (t, 2H, J=8.2 Hz). $^{13}$C-NMR (151 MHz, $CDCl_3$) δ 24.69, 67.06, 67.13, 107.10, 113.34, 118.02, 127.18, 134.69, 139.20.

Step 2: Synthesis of (E)-4-(phenyldiazenyl)naphthalen-1-amine (4)

Aniline (3, 3.3 ml, 36.4 mmol) was added into a mixture of $H_2O$ (10 ml) and HCl (10N, 7.4 ml) at 0° C. followed by dropwise addition of an aqueous solution (6 ml) of $NaNO_2$ (2.52 g, 36.5 mmol) over a period of 5 minutes and then this mixture is left stirring at 0° C. for 2 hrs. Then sodium acetate trihydrate was added to the solution until pH was 5 and then the diazonium salt was added dropwise into a suspension of 1-naphthylamine (5.2 g, 36.32 mmol) in a mixture of H$_2$O (100 ml), EtOH (15 ml) and HCl (10N, 3.6 ml) over a period of 30 minutes. The deep purple coloured suspension was left stirring at 0° C. for 2 hours and then an additional amount of H$_2$O (50 ml) and EtOH (25 ml) was added and stirring was continued at room temperature for 16 hours. The solution was then neutralized with addition of saturated aqueous solution of NaHCO$_3$ and the resulting red precipitate was filtered under vacuum, washed with H$_2$O adequately and left air dried. Crude product was purified by column chromatography using a mixture of cyclohexane/dichloromethane (from 50/50 up to 0/100, v/v) as the eluent to provide 6.4 g of 4 as a red solid. Yield 71%. M.p. 126-8° C. $^1$H-NMR (600 MHz, CDCl$_3$) δ 4.55 (brs, 2H, D$_2$O exch.), 6.77 (d, 1H, J=7.8 Hz), 7.48 (t, 1H, J=8.2 Hz), 7.54 (m, 1H), 7.58 (t, 2H, J=7.9 Hz), 7.68 (m, 1H), 7.77 (d, 1H, J=9.3 Hz), 7.98 (d, 1H, J=7.8 Hz), 8.07 (d, 2H, J=7.2 Hz), 9.12 (d, 1H, J=10.3 Hz). $^{13}$C-NMR (151 MHz, CDCl$_3$) δ 109.15, 113.99, 120.71, 122.51, 122.73, 124.14, 125.39, 127.17, 129.13, 129.86, 133.22, 140.39, 146.39, 153.64.

Step 3: Synthesis of (2-methyl-6-((E)-(4-((E)-phenyldiazenyl)naphthalen-1-yl)diazenyl)-2,3-dihydro-1H-perimidin-2-yl)methanol (5)

(E)-4-(Phenyldiazenyl)naphthalen-1-amine (4, 0.5 g, 2.02 mmol) was dissolved in DMF (2 ml) and then H$_2$O (3 ml) and HCl (10N, 0.6 ml) were added. This mixture was cooled at 0° C. and then an aqueous solution (1 ml) of NaNO$_2$ (139 mg, 2.02 mmol) was added dropwise over a period of 5 minutes. The diazonium salt was left stirring at 0° C. for 2 hours and then was added dropwise into a beaker containing perimidine 2 (473 mg, 2.02 mmol) in ethanol (6 ml) under vigorous stirring at 0° C. The reaction mixture was left stirring at 0° C. for 30 minutes and then at room temperature for 90 minutes. The solution was then neutralized with addition of saturated aqueous solution of NaHCO$_3$ and the resulting dark precipitate was left standing at 0° C. for 60 minutes and then filtered under vacuum, washed with H$_2$O and left air dried. Crude product was purified by column chromatography using a mixture of dichloromethane/ethyl acetate (from 100/0 up to 100/30, v/v) as the eluent to provide 0.45 g of 5 as a black solid. Yield 47%. M.p.>270° C.$_{(decomp)}$. $^1$H NMR (600 MHz, acetone-d$_6$) δ 1.58 (s, 3H), 3.66 (d, 2H, J=5.7 Hz), 4.35 (t, 1H, D$_2$O exch., J=5.7 Hz), 5.99 (brs, 1H, D$_2$O exch.), 6.67 (d, 1H, J=7.4 Hz), 6.71 (d, 1H, J=8.4 Hz), 6.98 (brs, 1H, D$_2$O exch.), 7.44 (t, 1H, J=8.2 Hz), 7.56 (t, 1H, J=7.3 Hz), 7.62 (t, 2H, J=7.3 Hz), 7.77 (m, 2H), 8.05 (d, 1H, J=8.3 Hz), 8.08-8.12 (m, 3H), 8.23 (d, 1H, J=8.4 Hz), 8.35 (d, 1H, J=8.4 Hz), 9.09 (m, 1H), 9.17 (m, 1H). $^{13}$C NMR (151 MHz, acetone-d$_6$) δ 24.66, 67.57, 68.35, 106.27, 106.95, 111.97, 112.02, 112.41, 113.51, 118.83, 123.97, 124.16, 124.94, 127.62, 128.18, 130.27, 130.67, 132.11, 132.74, 133.56, 134.96, 140.41, 142.50, 147.74, 148.05, 151.53, 154.38. HR-MS (ESI) m/z: calcd for C$_{29}$H$_{25}$N$_6$O, [M1+H]$^+$=473.2084, found 473.2074. Anal. Calcd for C$_{29}$H$_{24}$N$_6$O: C, 73.71; H, 5.12; N, 17.78. Found: C, 73.84; H, 5.17; N, 17.61.

Step 4: Synthesis of (2-methyl-6-((E)-(4-((E)-phenyldiazenyl)naphthalen-1-yl)diazenyl)-2,3-dihydro-1H-perimidin-2-yl)methyl 5-((3aR,4R,6aS)-2-oxo-hexahydro-1H-thieno[3,4-d]imidazol-4-yl)pentanoate (6)

DCC (93 mg, 0.45 mmol) and DMAP (10 mg, 0.08 mmol) were added into a suspension of biotin (98 mg, 0.40 mmol) in 10 ml of anhydrous dichloromethane and this mixture was left stirring at room temperature for 15 minutes, followed by addition of a dichloromethane solution (6 ml) of alcohol 5 (200 mg, 0.42 mmol). The reaction mixture was left stirring at room temperature for 72 hours. Then it was diluted with a mixture of CH$_2$Cl$_2$/MeOH (20 ml, 100/5, v/v) and filtered through a celite pad. The filtrate was evaporated under reduced pressure and then crude product was purified by column chromatography, using a mixture of ethyl acetate/methanol (from 100/0 up to 100/8, v/v) as the eluent to provide 250 mg of 6 as a black solid. Yield 89%. M.p. 152-5° C. $^1$H NMR (600 MHz, DMSO-d6) δ 1.14-1.28 (m, 2H), 1.36-1.44 (m, 3H), 1.48-1.56 (m, 4H), 2.08-2.20 (m, 2H), 2.54 (d, 1H, J=12.5 Hz), 2.69-2.76 (m, 1H), 2.94-3.01 (m, 1H), 4.00-4.09 (m, 2H), 4.12-4.24 (m, 2H), 6.30 (brs, 1H, D$_2$O exch.), 6.36 (brs, 1H, D$_2$O exch.), 6.56 (d, 1H, J=7.5 Hz), 6.62 (dd, 1H, J=8.5 Hz+2.4 Hz), 6.97 (brs, 1H, D$_2$O exch.), 7.42 (t, 1H, J=8.1 Hz), 7.61 (t, 1H, J=7.2 Hz), 7.67 (t, 2H, J=7.3 Hz), 7.80-7.85 (m, 2H), 7.99-8.04 (m, 2H), 8.08 (d, 2H, J=7.3 Hz), 8.11 (brs, 1H, D$_2$O exch.), 8.15 (d, 1H, J=8.3 Hz), 8.18 (dd, 1H, J=8.5 Hz+2.9 Hz), 9.01 (d, 1H, J=9.2 Hz), 9.07-9.10 (m, 1H). $^{13}$C NMR (151 MHz, DMSO-d6) δ 24.20, 24.54, 27.97, 28.04, 33.21, 40.05, 55.31, 59.09, 60.94, 65.54, 67.76, 104.97, 105.24, 109.76, 109.96, 111.31, 112.77, 118.90, 122.92, 123.03, 123.78, 127.00, 127.65, 129.58, 130.25, 131.01, 131.51, 131.98, 133.23, 138.41, 141.59, 145.91, 147.46, 150.04, 152.84, 162.63, 172.51. HR-MS (ESI) m/z: calcd for C$_{39}$H$_{39}$N$_8$O$_3$S, [M1+1-1]$^+$=699.2860, found 699.2849. Anal. Calcd for C$_{39}$H$_{38}$N$_8$O$_3$S: C, 67.03; H, 5.48; N, 16.03. Found: C, 67.22; H, 5.60; N, 15.94.

Example 2

Synthesis of (2-methyl-6-((E)-(4-((E)-phenyldiazenyl)naphthalen-1-yl)diazenyl)-2,3-dihydro-1H-perimidin-2-yl)methyl 5-((3aR,4R,6aS)-2-oxohexahydro-1H-thieno[3,4-d]imidazol-4-yl)pentanoate by method B (Scheme 3.12)

Scheme 3.12. Synthesis of (2-methyl-6-((E)-(4-((E)-phenyldiazenyl)naphthalen-1-yl)diazenyl)-2,3-dihydro-1H-perimidin-2-yl)methyl 5-((3aR,4R,6aS)-2-oxohexahydro-1H-thieno[3,4-d]imidazol-4-yl)pentanoate by method B.

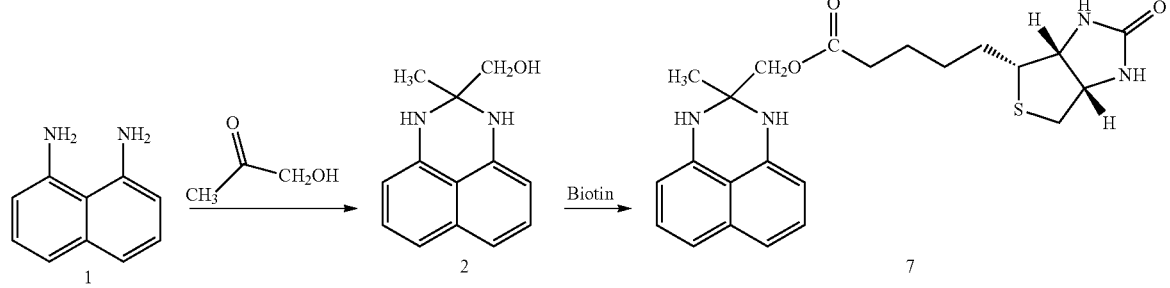

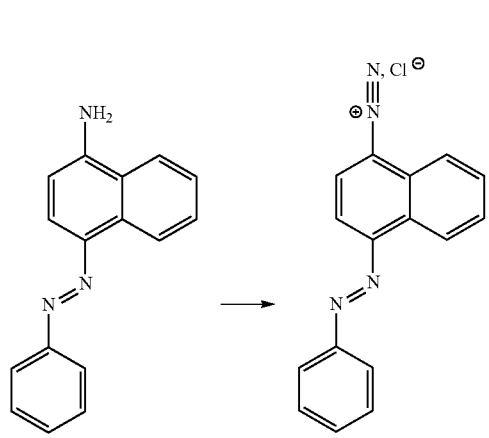

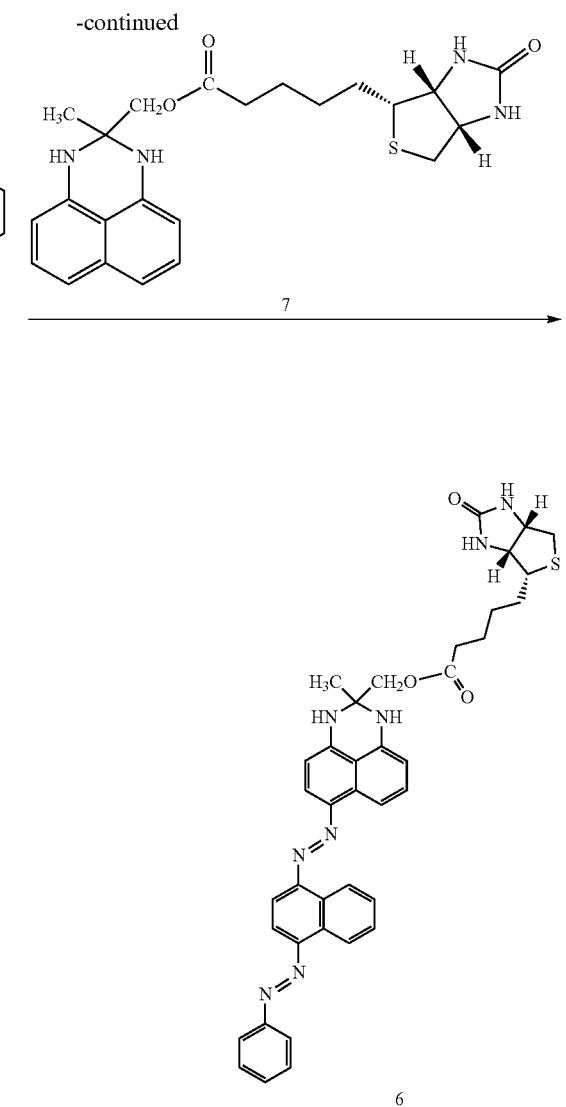

Step 1 Synthesis of (2-methyl-2,3-dihydro-1H-perimidin-2-yl)methyl 5-((3aR,4R,6aS)-2-oxohexahydro-1H-thieno[3,4-d]imidazol-4-yl)pentanoate (7)

DCC (304 mg, 1.48 mmol) and DMAP (23 mg, 0.18 mmol) were added into a suspension of biotin (300 mg, 1.23 mmol) in 15 ml of anhydrous dichloromethane and this mixture was left stirring at room temperature for 15 minutes, followed by addition of alcohol 2 (316 mg, 1.48 mmol, its synthesis is described at step 1 of the reference example 1). The reaction mixture was left stirring at room temperature for 70 hours. Then it was diluted with a mixture of $CH_2Cl_2$/MeOH (20 ml, 100/5, v/v) and filtered through a celite pad. The filtrate was evaporated under reduced pressure and then crude product was purified by column chromatography, using a mixture of ethyl acetate/methanol (from 100/0 up to 100/8, v/v) as the eluent to provide 510 mg of 7 as an off-white foam. Yield 94%. $^1$H-NMR (600 MHz, DMSO-d6) δ 1.20-1.34 (m, 2H), 1.38 (s, 3H), 1.42-1.64 (m, 3H), 1.66-1.74 (m, 1H), 2.24 (t, 2H, J=7.4 Hz), 2.58 (d, 1H, J=12.4 Hz), 2.81 (dd, 1H, J=12.4 Hz+5.1 Hz), 3.03-3.08 (m, 1H), 3.94 (s, 2H), 4.09-4.13 (m, 1H), 4.28-4.32 (m, 1H), 6.32 (brs, 1H, D$_2$O exch.), 6.40 (d, 2H, J=7.4 Hz), 6.42 (brs, 1H, D$_2$O exch.), 6.52 (brs, 2H, D$_2$O exch.), 6.91 (d, 2H, J=7.9 Hz), 7.11 (t, 2H, J=7.8 Hz). $^{13}$C-NMR (151 MHz, DMSO-d6) δ 24.29, 24.61, 27.98, 28.02, 33.28, 39.85, 55.36, 59.23, 61.05, 64.44, 66.96, 103.96, 111.38, 114.75, 127.06, 134.10, 140.77, 162.75, 172.72.

Step 2: Synthesis of (2-methyl-6-((E)-(4-((E)-phenyldiazenyl)naphthalen-1-yl)diazenyl)-2,3-dihydro-1H-perimidin-2-yl)methyl 5-((3aR,4R,6aS)-2-oxohexahydro-1H-thieno[3,4-d]imidazol-4-yl)pentanoate (6)

(E)-4-(Phenyldiazenyl)naphthalen-1-amine (4, 124 mg, 0.5 mmol, its synthesis is described at step 2 of the typical example 1) was dissolved in DMF (0.5 ml) and then H$_2$O (3 ml) and HCl (10N, 0.15 ml) were added. This mixture was cooled at 0° C. and then an aqueous solution (1 ml) of NaNO$_2$ (35 mg, 0.5 mmol) was added dropwise over a period of 3 minutes. The diazonium salt was left stirring at 0° C. for 2 hours and then sodium acetate trihydrate was added to the solution until pH was 6. This diazonium salt was added dropwise into a beaker containing ester 7 (220 mg, 0.5 mmol) in ethanol (4 ml) under vigorous stirring at 0° C. The reaction mixture was left stirring at 0° C. for 30 minutes and then at room temperature for 90 minutes. The solution was then neutralized with addition of saturated aqueous solution of NaHCO$_3$ and the resulting dark precipitate was left standing at 0° C. for 60 minutes and then filtered under vacuum, washed with H$_2$O and left air dried. Crude product was purified by column chromatography using a mixture of dichloromethane/methanol (from 100/3 up to 100/5, v/v) as the eluent to provide 240 mg of 6 as a blue-black film. Yield 69%. $^1$H-NMR and $^{13}$C-NMR identical to those referred at step 4 of typical example 1.

Example 3

Synthesis of 4-(6-((E)-4-((E)-phenyldiazenyl)naphthalen-1-yl)diazenyl)-2,3-dihydro-1H-perimidin-2-yl)phenyl 5-((3aR,4R,6aS)-2-oxohexahydro-1H-thieno[3,4-d]imidazol-4-yl)pentanoate by method A (Scheme 3.13)

Scheme 3.13. Synthesis of 4-(6-((E)-4-((E)-phenyldiazenyl)naphthalen-1-yl)diazenyl)-2,3-dihydro-1H-perimidin-2-yl)phenyl 5-((3aR,4R,6aS)-2-oxohexahydro-1H-thieno[3,4-d]imidazol-4-yl)pentanoate by method A.

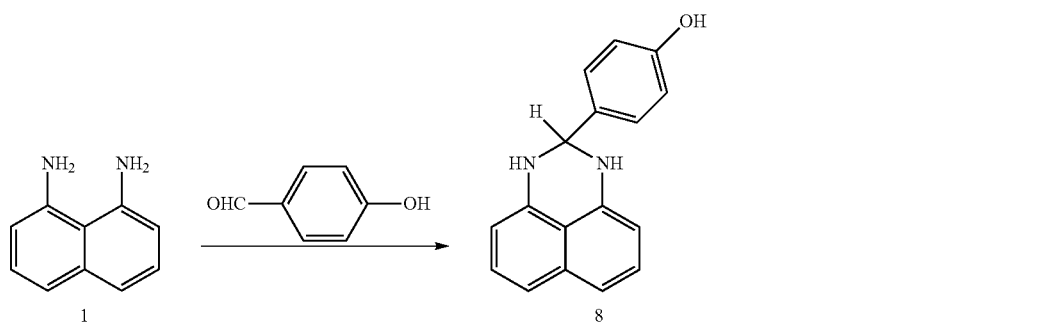

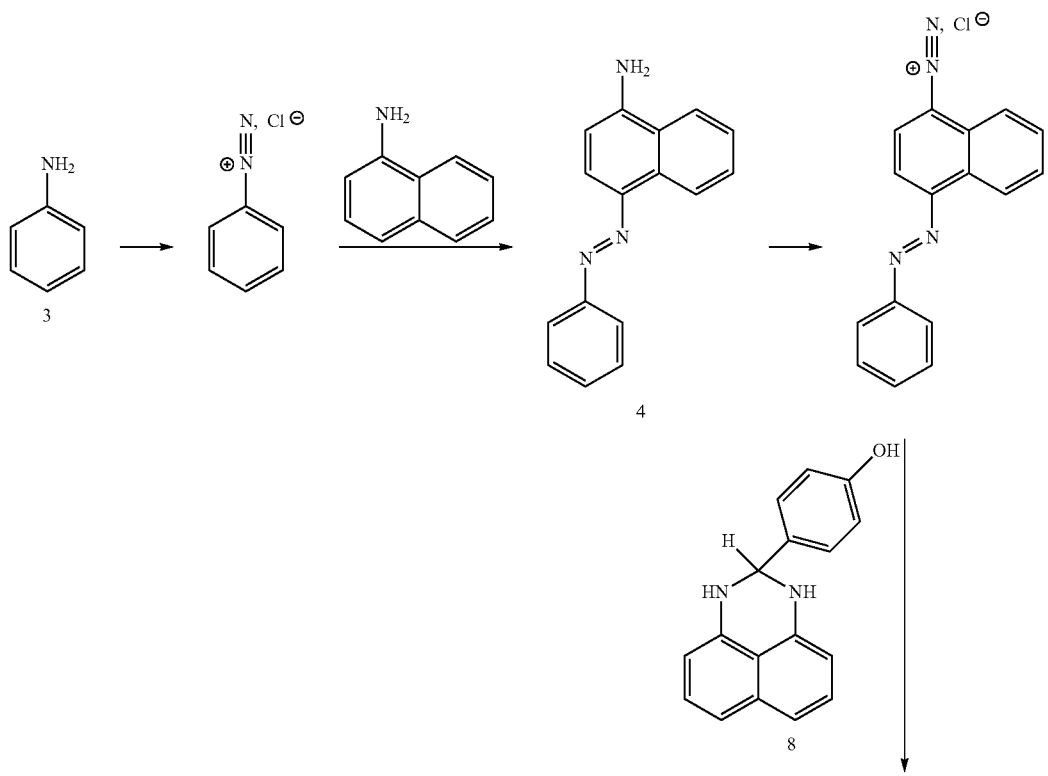

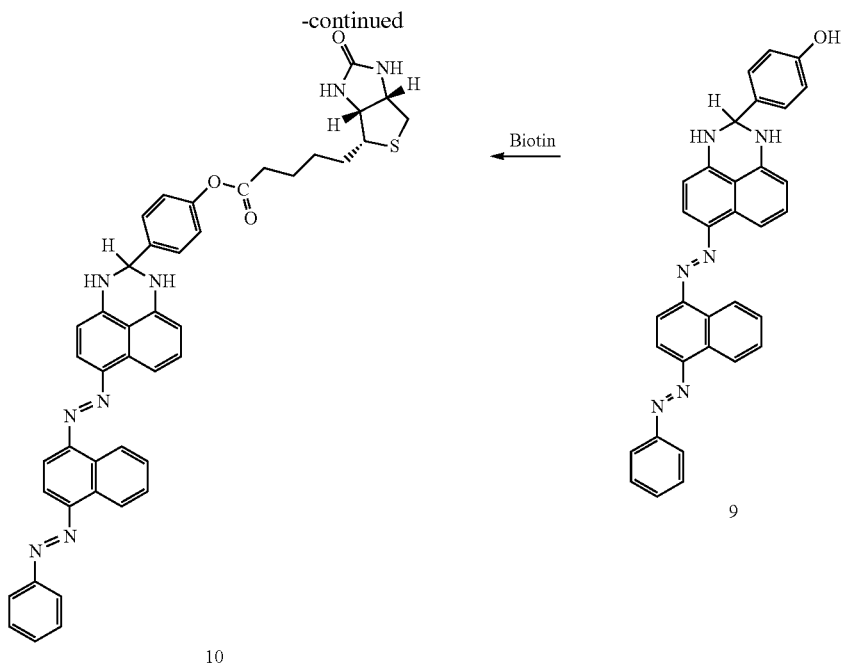

Step 1: Synthesis of 4-(2,3-dihydro-1H-perimidin-2-yl)phenol (8)

4-Hydroxybenzaldehyde (2.32 g, 18.96 mmol) was added into a solution of 1,8-diaminonaphthalene (1, 3 g, 18.96 mmol) in ethanol (15 mL) and this mixture was refluxed for 40 minutes. Upon completion of reaction, the mixture was allowed to reach room temperature and the solid that precipitated was filtered under vacuum, washed with ethanol (10 mL) and left air-dried. Finally, 4.95 g of compound 8 were obtained as an off-white solid. Yield 100%. M.p. 169-171° C. $^1$H-NMR (600 MHz, DMSO-d6) δ 5.25 (s, 1H), 6.48 (d, 2H, J=7.4 Hz), 6.58 (brs, 2H, D$_2$O exch.), 6.81 (d, 2H, J=8.5 Hz), 6.97 (d, 2H, J=8.1 Hz), 7.14 (t, 2H, J=7.7 Hz), 7.41 (d, 2H, J=8.5 Hz), 9.48 (brs, 1H, D$_2$O exch.). $^{13}$C-NMR (151 MHz, DMSO-d6) δ 66.32, 104.22, 112.48, 114.86, 115.13, 126.80, 129.13, 131.96, 134.42, 143.44, 157.73.

Step 2: Synthesis of 4-(6-((E)-(4-((E)-phenyldiazenyl)naphthalen-1-yl)diazenyl)-2,3-dihydro-1H-perimidin-2-yl)phenol (9)

(E)-4-(Phenyldiazenyl)naphthalen-1-amine (4, 0.5 g, 2.02 mmol, its synthesis is described at step 2 of the typical example 1) was dissolved in DMF (2 ml) and then H$_2$O (6 ml) and HCl (10N, 0.6 ml) were added. This mixture was cooled at 0° C. and then an aqueous solution (1 ml) of NaNO$_2$ (139 mg, 2.02 mmol) was added dropwise over a period of 5 minutes. The diazonium salt was left stirring at 0° C. for 2 hours and then it was added dropwise into a beaker containing perimidine 8 (529 mg, 2.02 mmol) in ethanol (10 ml) under vigorous stirring at 0° C. The reaction mixture was left stirring at 0° C. for 30 minutes and then at room temperature for 90 minutes. The solution was then neutralized with addition of saturated aqueous solution of NaHCO$_3$ and the resulting dark precipitate was left standing at 0° C. for 60 minutes and then filtered under vacuum, washed with H$_2$O and left air dried. Crude product was purified by column chromatography using a mixture of dichloromethane/ethyl acetate (from 100/0 up to 100/4, v/v) as the eluent to provide 0.62 g of 9 as a black solid. Yield 59%. M.p.>270° C.$_{(decomp)}$. $^1$H NMR (600 MHz, DMSO-d6) δ 5.59 (s, 1H), 6.68 (d, 1H, J=6.9 Hz), 6.72 (d, 1H, J=8.5 Hz), 6.87 (d, 2H, J=8.5 Hz), 7.07 (brs, 1H, D$_2$O exch.), 7.43-7.49 (m, 3H), 7.59 (t, 1H, J=7.4 Hz), 7.65 (t, 2H, J=7.6 Hz), 7.77-7.84 (m, 2H), 7.99 (d, 1H, J=8.4 Hz), 8.04 (d, 1H, J=8.4 Hz), 8.08 (d, 2H, J=7.5 Hz), 8.17-8.21 (m, 2H), 8.24 (d, 1H, J=8.4 Hz), 9.01 (m, 1H), 9.10 (m, 1H), 9.61 (brs, 1H, D$_2$O exch.). $^{13}$C NMR (151 MHz, DMSO-d6) δ 65.89, 105.23, 105.76, 110.51, 110.81, 111.34, 112.77, 115.09, 118.73, 122.93, 123.04, 123.82, 126.98, 127.60, 129.03, 129.55, 130.07, 131.05, 131.20, 131.46, 132.01, 133.55, 138.64, 143.63, 145.94, 149.10, 150.06, 152.85, 158.05. HR-MS (ESI) m/z: calcd for C$_{33}$H$_{25}$N$_6$O, [M1+H]$^+$= 521.2084, found 521.2078. Anal. Calcd for C$_{33}$H$_{24}$N$_6$O: C, 76.14; H, 4.65; N, 16.14. Found: C, 76.02; H, 4.59; N, 16.21.

Step 3: Synthesis of 4-(6-((E)-4-((E)-phenyldiazenyl)naphthalen-1-yl)diazenyl)-2,3-dihydro-1H-perimidin-2-yl)phenyl 5-((3aR,4R,6aS)-2-oxohexahydro-1H-thieno[3,4-d]imidazol-4-yl)pentanoate (10)

DCC (174 mg, 0.85 mmol) and DMAP (20 mg, 0.15 mmol) were added into a suspension of biotin (188 mg, 0.77 mmol) in 20 ml of anhydrous dichloromethane and this mixture was left stirring at room temperature for 15 minutes, followed by addition of a dichloromethane solution (10 ml) of alcohol 9 (400 mg, 0.77 mmol). The reaction mixture was left stirring at room temperature for 86 hours. Then it was diluted with a mixture of CH$_2$Cl$_2$/MeOH (20 ml, 100/5, v/v) and filtered through a celite pad. The filtrate was evaporated under reduced pressure and then crude product was purified by column chromatography, using a mixture of dichloromethane/methanol (from 100/0 up to 100/6, v/v) as the eluent to provide 140 mg of 10 as a black solid. Yield 24%. M.p. 166-169° C. 1H NMR (600 MHz, acetone-d6) δ

1.52-1.60 (m, 2H), 1.64-1.72 (m, 1H), 1.76-1.86 (m, 3H), 2.62 (t, 2H, J=7.5 Hz), 2.71 (d, 1H, J=12.5 Hz), 2.94 (dd, 1H, J=12.5 Hz+5.1 Hz), 3.22-3.26 (m, 1H), 4.31-4.36 (m, 1H), 4.47-4.51 (m, 1H), 5.71 (s, 1H), 5.75 (brs, 1H, D$_2$O exch.), 5.84 (brs, 1H, D$_2$O exch.), 6.31 (brs, 1H, D$_2$O exch.), 6.77 (d, 1H, J=7.4 Hz), 6.81 (d, 1H, J=8.4 Hz), 7.18 (brs, 1H, D$_2$O exch.), 7.19 (d, 2H, J=8.5 Hz), 7.49 (t, 1H, J=7.9 Hz), 7.59 (t, 1H, J=7.3 Hz), 7.65 (t, 2H, J=7.5 Hz), 7.70 (d, 2H, J=8.5 Hz), 7.77-7.82 (m, 2H), 8.06 (d, 1H, J=8.3 Hz), 8.10-8.13 (m, 3H), 8.25 (d, 1H, J=8.4 Hz), 8.42 (d, 1H, J=8.4 Hz), 9.09 (m, 1H), 9.18 (m, 1H). $^{13}$C NMR (151 MHz, acetone-d6) δ 25.68, 29.27, 29.31, 34.54, 41.12, 56.52, 60.89, 62.55, 67.75, 106.46, 107.18, 112.59, 112.92, 113.52, 118.38, 122.94, 124.05, 124.24, 124.96, 127.81, 128.30, 129.93, 130.36, 130.51, 132.27, 132.87, 133.57, 135.12, 139.19, 140.93, 144.19, 148.04, 149.28, 149.34, 151.43, 152.64, 154.43, 163.76, 172.61. HR-MS (ESI) m/z: calcd for C$_{43}$H$_{39}$N$_8$O$_3$S, [M1+H]$^+$=747.2860, found 747.2860; calcd for C$_{43}$H$_{38}$N$_8$O$_3$SNa, [M1+Na]$^+$=769.2680, found 769.2679. Anal. Calcd for C$_{43}$H$_{38}$N$_8$O$_3$S: C, 69.15; H, 5.13; N, 15.00. Found: C, 69.32; H, 5.22; N, 14.84.

Example 4

Synthesis of 4-(6-((E)-4-((E)-phenyldiazenyl)naphthalen-1-yl)diazenyl)-2,3-dihydro-1H-perimidin-2-yl)phenyl 5-((3aR,4R,6aS)-2-oxohexahydro-1H-thieno[3,4-d]imidazol-4-yl)pentanoate by Method B (Scheme 3.14)

Scheme 3.14. Synthesis of 4-(6-((E)-4-((E)-phenyladiazenyl)naphthalen-1-yl)diazenyl)-2,3-dihydro-1H-perimidin-2-yl)phenyl 5-((3aR,4R,6aS)-2-oxohexahydro-1H-thieno[3,4-d]imidazol-4-yl)pentanoate by method B

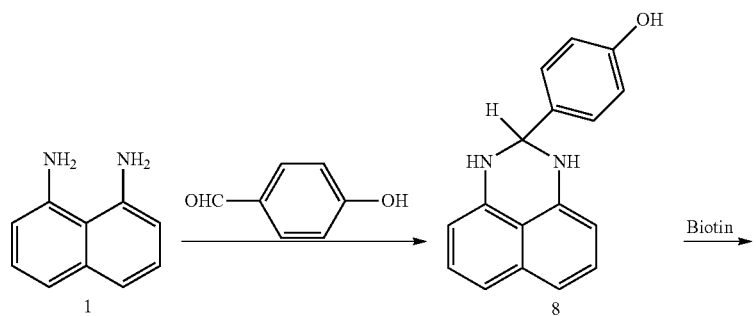

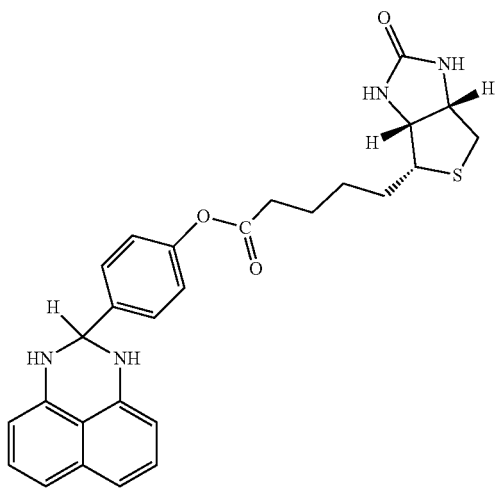

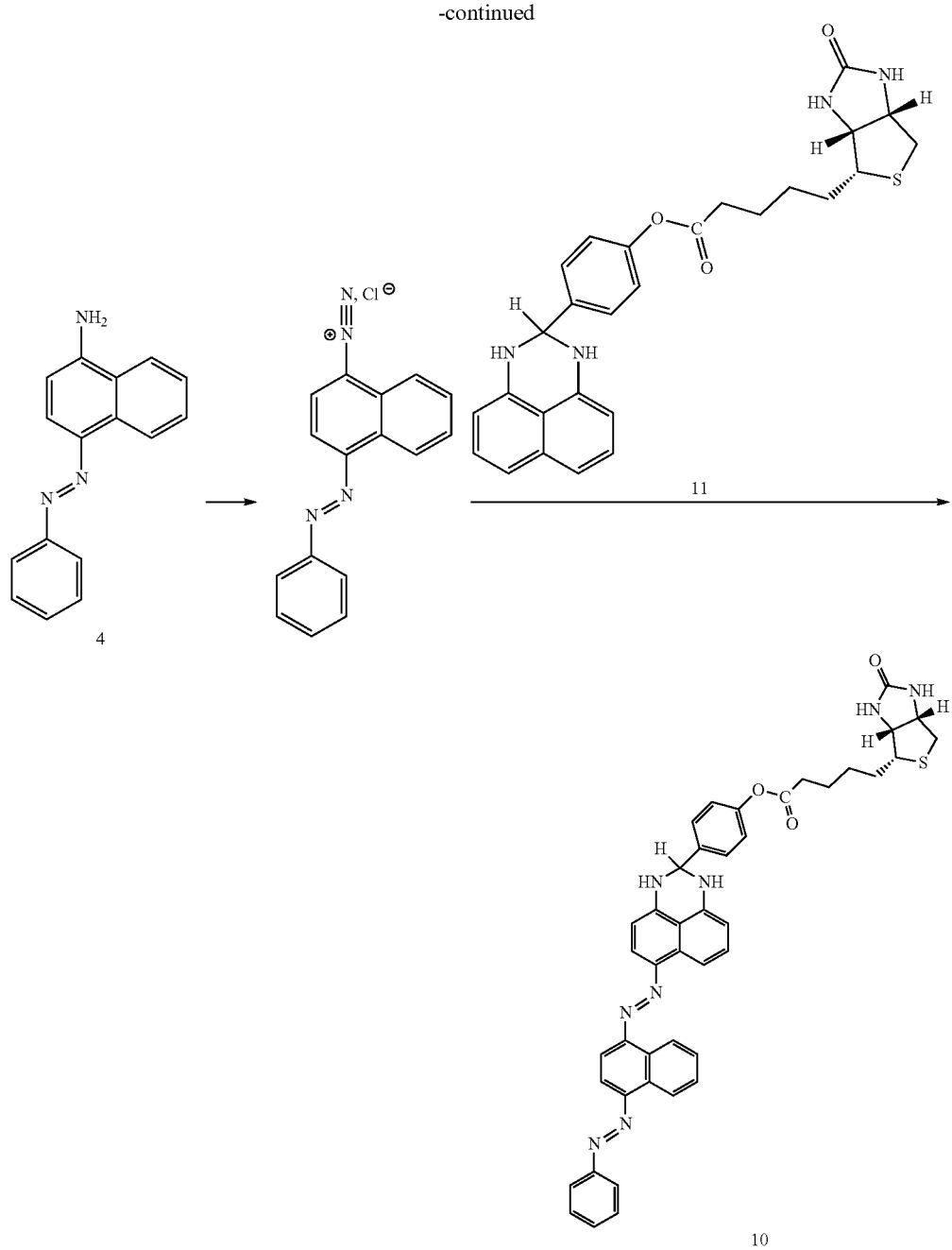

Step 1: Synthesis of 4-(2,3-dihydro-1H-perimidin-2-yl)phenyl 5-((3aR,4R,6aS)-2-oxohexahydro-1H-thieno[3,4-d]imidazol-4-yl)pentanoate (11)

DCC (304 mg, 1.48 mmol) and DMAP (23 mg, 0.18 mmol) were added into a suspension of biotin (300 mg, 1.23 mmol) in 15 ml of anhydrous dichloromethane and this mixture was left stirring at room temperature for 15 minutes, followed by addition of phenol 8 (387 mg, 1.48 mmol, its synthesis is described at step 1 of the typical example 3). The reaction mixture was left stirring at room temperature for 70 hours. Then it was diluted with a mixture of $CH_2Cl_2$/MeOH (20 ml, 100/5, v/v) and filtered through a celite pad. The filtrate was evaporated under reduced pressure and then crude product was purified by column chromatography, using a mixture of ethyl acetate/methanol (from 100/0 up to 100/10, v/v) as the eluent to provide 660 mg of 11 as a beige foam. Yield 92%. $^1$H-NMR (600 MHz, DMSO-d6) δ 1.20-1.30 (m, 2H), 1.41-1.50 (m, 1H), 1.64-1.73 (m, 3H), 2.58-2.62 (m, 3H), 2.83 (dd, 1H, J=12.4 Hz+5.1 Hz), 3.12-3.16 (m, 1H), 4.14-4.18 (m, 1H), 4.29-4.34 (m, 1H), 5.35 (s, 1H), 6.37 (brs, 1H, $D_2O$ exch.), 6.45 (brs, 1H, $D_2O$ exch.), 6.49 (d, 2H, J=7.2 Hz), 6.77 (brs, 2H, $D_2O$ exch.), 6.98 (d, 2H, J=7.8 Hz), 7.13-7.18 (m, 4H), 7.63 (d, 2H, J=8.5 Hz). $^{13}$C-NMR (151 MHz, DMSO-d6) δ 24.40, 27.94, 28.00, 33.31, 39.87, 55.32, 59.23, 61.06, 65.83, 104.36, 112.43, 115.33, 121.62, 126.85, 129.04, 134.36, 139.28, 142.97, 150.61, 162.74, 171.79.

Step 2: Synthesis of 4-(6-((E)-4-((E)-phenyldiazenyl)naphthalen-1-yl)diazenyl)-2,3-dihydro-1H-perimidin-2-yl)phenyl 5-((3aR,4R,6aS)-2-oxohexahydro-1H-thieno[3,4-d]imidazol-4-yl)pentanoate (10)

(E)-4-(Phenyldiazenyl)naphthalen-1-amine (4, 180 mg, 0.73 mmol, its synthesis is described at step 2 of the typical example 1) was dissolved in DMF (0.7 ml) and then H$_2$O (4.4 ml) and HCl (10N, 0.22 ml) were added. This mixture was cooled at 0° C. and then an aqueous solution (1 ml) of NaNO$_2$ (51 mg, 0.73 mmol) was added dropwise over a period of 3 minutes. The diazonium salt was left stirring at 0° C. for 2 hours and then sodium acetate trihydrate was added to the solution until pH was 6. This diazonium salt was added dropwise into a beaker containing ester 11 (356 mg, 0.73 mmol) in ethanol (8 ml) under vigorous stirring at 0° C. The reaction mixture was left stirring at 0° C. for 30 minutes and then at room temperature for 90 minutes. The solution was then neutralized with addition of saturated aqueous solution of NaHCO$_3$ and the resulting dark precipitate was left standing at 0° C. for 60 minutes and then filtered under vacuum, washed with H$_2$O and left air dried. Crude product was purified by column chromatography using a mixture of dichloromethane/methanol (from 100/1 up to 100/5, v/v) as the eluent to provide 160 mg of 10 as a blue-black film. Yield 29%. $^1$H-NMR and $^{13}$C-NMR identical to those referred at step 3 of typical example 3.

Example 5

Synthesis of 2-(2-Methyl-6-((E)-(4-((E)-phenyldiazenyl)naphthalen-1-yl)diazenyl)-2,3-dihydro-1H-perimidin-2-yl)ethyl 5-43aR,4R,6aS)-2-oxohexahydro-1H-thieno[3,4-d]imidazol-4-yl)pentanoate (17) by Method B

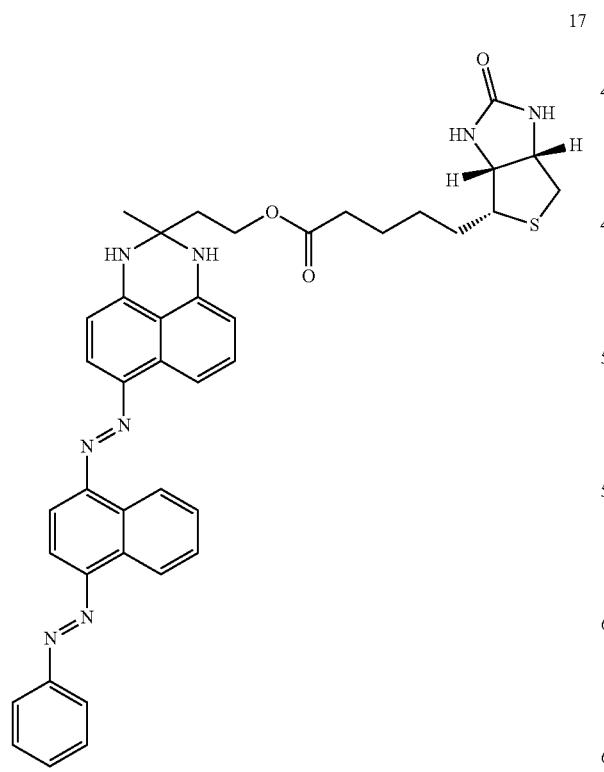

17

Compound 17 (2-(2-Methyl-6-((E)-(4-((E)-phenyldiazenyl)naphthalen-1-yl)diazenyl)-2,3-dihydro-1H-perimidin-2-yl)ethyl 5-((3aR,4R,6aS)-2-oxohexahydro-1H-thieno[3,4-d]imidazol-4-yl)pentanoate) was prepared according to the general procedure described in respect of Example 1 above.

Step 1: Synthesis of 2-(2-Methyl-2,3-dihydro-1H-perimidin-2-yl)ethano (12)

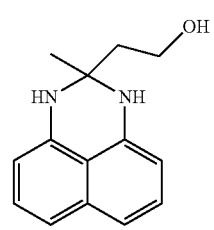

12

This compound was synthesized according to the general procedure described in respect of Step 1 of Example 1 above, upon reaction of 1,8-diaminonaphthalene with 4-hydroxy-2-butanone, in 95% yield. Beige solid. M.p. 132-3° C. NMR (600 MHz, acetone-d6) δ 1.46 (s, 3H), 2.00 (t, 2H, J=6.5 Hz), 3.70 (brs, 1H, D$_2$O exch.), 3.85 (m, 2H), 5.65 (brs, 2H, D$_2$O exch.), 6.44 (d, 2H, J=7.4 Hz), 6.99 (d, 2H, J=7.9 Hz), 7.14 (t, 2H, J=7.8 Hz). $^{13}$C NMR (151 MHz, acetone-d$_6$) δ 26.85, 43.56, 59.06, 67.06, 105.74, 113.53, 116.37, 127.92, 135.76, 142.42.

Step 2: Synthesis of (E)-4-(phenyldiazenyl)naphthalen-1-amine (4)

This compound was synthesized according to the general procedure described in respect of Step 2 of Example 1 above.

Step 3: Synthesis of 2-(2-Methyl-6-((E)-(4-((E)-phenyldiazenyl)naphthalen-1-yl)diazenyl)-2,3-dihydro-1H-perimidin-2-yl)ethanol (15)

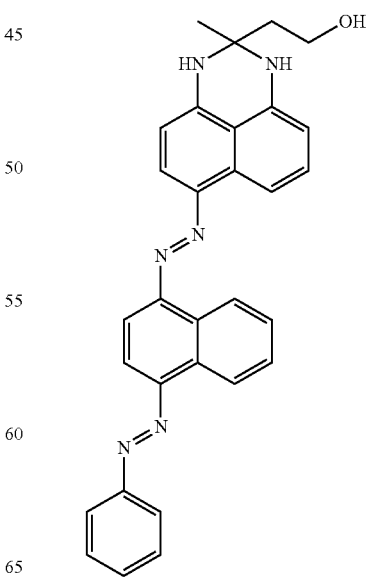

15

This compound was prepared according to the general procedure described in respect of Step 3 of Example 1 above, upon reaction of 4 with perimidine 12. The crude product was purified by column chromatography using a mixture of chloroform/methanol (from 100/1 up to 100/4, v/v) as the eluent to provide pure 15 as a black solid, in 54% yield. Mp 129-131° C. $^1$H NMR (600 MHz, acetone-d6) δ 1.60 (s, 3H), 2.13 (m, 2H), 3.83 (m, 1H, D$_2$O exch.), 3.88-3.95 (m, 2H), 6.04 (brs, 1H, D$_2$O exch.), 6.63 (d, 1H, J=7.4 Hz), 6.66 (d, 1H, J=8.4 Hz), 7.03 (brs, 1H, D$_2$O exch.), 7.44 (t, 1H, J=8.2 Hz), 7.58 (m, 1H), 7.65 (t, 2H, J=7.5 Hz), 7.76-7.82 (m, 2H), 8.06 (d, 1H, J=8.3 Hz), 8.09-8.13 (m, 3H), 8.23 (d, 1H, J=8.5 Hz), 8.33 (d, 1H, J=8.4 Hz), 9.09 (m, 1H), 9.17 (m, 1H). $^{13}$C NMR (151 MHz, acetone-d$_6$) δ 26.91, 43.67, 58.83, 68.03, 106.31, 107.04, 112.01, 112.06, 112.41, 113.54, 119.03, 123.99, 124.17, 124.96, 127.65, 128.22, 130.32, 130.77, 132.15, 132.75, 133.59, 135.04, 140.38, 142.83, 147.74, 148.25, 151.60, 154.42. HR-MS (ESI) m/z: calcd for C$_{30}$H$_{27}$N$_6$O, [M1+H]$^+$=487.2241, found 487.2232. Anal. Calcd for C$_{30}$H$_{26}$N$_6$O: C, 74.05; H, 5.39; N, 17.27. Found: C, 73.96; H, 5.34; N, 17.38.

Step 4: 2-(2-Methyl-6-((E)-(4-((E)-phenyldiazenyl) naphthalen-1-yl)diazenyl)-2,3-dihydro-1H-perimidin-2-yl)ethyl 5-((3aR,4R,6aS)-2-oxohexahydro-1H-thieno[3,4-d]imidazol-4-yl)pentanoate (17)

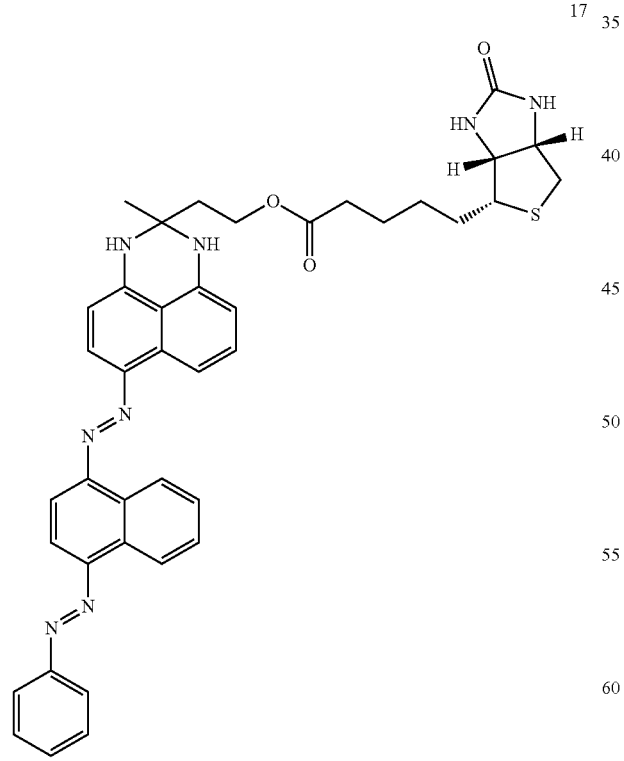

17

This compound was prepared according to the general procedure described in respect of Step 4 of Example 1 above, upon reaction of D-biotin with alcohol 15. The crude product was purified by column chromatography using a mixture of dichloromethane/methanol (from 100/1 up to 100/5, v/v) as the eluent to provide pure 17 as a black solid, in 58% yield. Mp 139-142° C. $^1$H NMR (600 MHz, acetone-d$_6$) δ 1.39-1.47 (m, 2H), 1.55-1.65 (m, 6H), 1.68-1.76 (m, 1H), 2.22-2.26 (m, 2H), 2.28-2.33 (m, 2H), 2.68 (dd, 1H, J=12.5 Hz+4.5 Hz), 2.85-2.90 (m, 1H), 3.12-3.17 (m, 1H), 4.23-4.29 (m, 1H), 4.31-4.35 (m, 2H), 4.42-4.48 (m, 1H), 5.75 (d, 1H, D$_2$O exch., J=10.2 Hz), 5.79 (d, 1H, D$_2$O exch., J=7.5 Hz), 6.13 (brs, 0.5H, D$_2$O exch.), 6.17 (brs, 0.5H, D$_2$O exch.), 6.65 (d, 1H, J=7.4 Hz), 6.69 (d, 1H, J=8.4 Hz), 7.13 (brs, 0.5H, D$_2$O exch.), 7.19 (brs, 0.5H, D$_2$O exch.), 7.44 (t, 1H, J=7.4 Hz), 7.59 (m, 1H), 7.65 (t, 2H, J=7.9 Hz), 7.76-7.82 (m, 2H), 8.06 (d, 1H, J=8.3 Hz), 8.09-8.13 (m, 3H), 8.23 (d, 1H, J=8.4 Hz), 8.33 (d, 1H, J=8.3 Hz), 9.09 (m, 1H), 9.17 (m, 1H). $^{13}$C NMR (151 MHz, acetone-d$_6$) δ 25.66, 25.70, 27.80, 29.20, 34.49, 40.08, 41.02, 56.50, 60.94, 61.26, 62.50, 67.41, 106.37, 107.02, 111.97, 112.08, 112.47, 113.57, 188.99, 124.02, 124.21, 124.99, 127.72, 128.27, 130.36, 130.82, 132.22, 132.79, 133.61, 135.01, 140.47, 142.71, 147.83, 148.23, 151.60, 154.45, 163.76, 173.85. HR-MS (ESI) m/z: calcd for C$_{40}$H$_{41}$N$_8$O$_3$S, [M1+H]$^+$=713.3016, found 713.3005. Anal. Calcd for C$_{40}$H$_{40}$N$_8$O$_3$S: C, 67.39; H, 5.66; N, 15.72. Found: C, 67.56; H, 5.75; N, 15.59.

Example 6

Synthesis of 3-(2-Methyl-6-((E)-(4-((E)-phenyldiazenyl)naphthalen-1-yl)diazenyl)-2,3-dihydro-1H-perimidin-2-yl)propyl 5-43aR,4R,6aS)-2-oxohexahydro-1H-thieno[3,4-d]imidazol-4-yl)pentanoate (18)

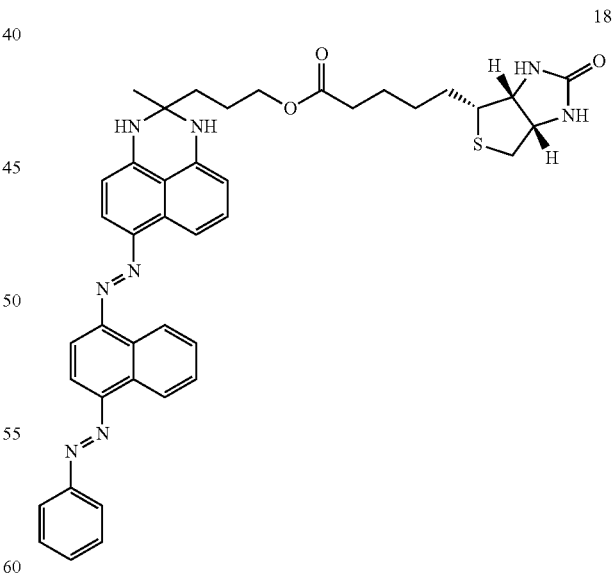

18

Compound 18 (3-(2-Methyl-6-((E)-(4-((E)-phenyldiazenyl)naphthalen-1-yl)diazenyl)-2,3-dihydro-1H-perimidin-2-yl)propyl 5-((3aR,4R,6aS)-2-oxohexahydro-1H-thieno[3, 4-d]imidazol-4-yl)pentanoate) was prepared according to the general procedure described in respect of Example 1 above.

Step 1: Synthesis of 3-(2-Methyl-2,3-dihydro-1H-perimidin-2-yl)propan-1-ol (13)

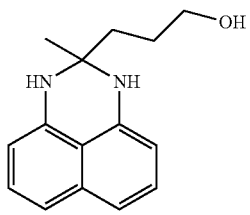

13

This compound was synthesized according to the general procedure described in respect of Step 1 of Example 1 above, upon reaction of 1,8-diaminonaphthalene with 5-hydroxy-2-pentanone, in 97% yield. Grey solid. M.p. 149-150° C. $^1$H NMR (600 MHz, acetone-$d_6$) δ 1.43 (s, 3H), 1.68-1.74 (m, 2H), 1.79-1.83 (m, 2H), 3.45-3.53 (m, 3H), 5.61 (brs, 2H, $D_2O$ exch.), 6.43 (d, 2H, J=7.4 Hz), 6.95 (d, 2H, J=8.1 Hz), 7.12 (t, 2H, J=7.9 Hz). $^{13}$C NMR (151 MHz, acetone-d6) δ 27.20, 28.28, 38.32, 62.90, 67.07, 105.35, 113.48, 116.06, 127.93, 135.82, 142.71.

Step 2: Synthesis of (E)-4-(phenyldiazenyl)naphthalen-1-amine (4)

This compound was synthesized according to the general procedure described in respect of Step 2 of Example 1 above

Step 3: Synthesis of 3-(2-Methyl-6-((E)-(4-((E)-phenyldiazenyl)naphthalen-1-yl)diazenyl)-2,3-dihydro-1H-perimidin-2-yl)propan-1-ol (16)

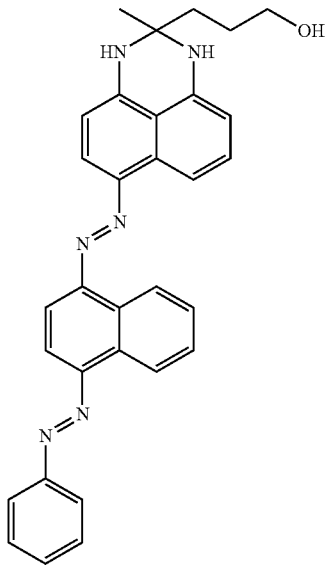

16

This compound was prepared according to the general procedure described in respect of Step 3 of Example 1 above, upon reaction of 4 with perimidine 13. The crude product was purified by column chromatography using a mixture of cyclohexane/ethyl acetate (from 1/1 up to 2/8, v/v) as the eluent to provide pure 16 as a black solid, in 50% yield. Mp 124-6° C. $^1$H NMR (600 MHz, acetone-$d_6$) δ 1.56 (s, 3H), 1.74-1.80 (m, 2H), 1.92-1.97 (m, 2H), 3.53-3.59 (m, 3H), 6.03 (brs, 1H, $D_2O$ exch.), 6.63 (d, 1H, J=7.3 Hz), 6.66 (d, 1H, J=8.5 Hz), 7.06 (brs, 1H, $D_2O$ exch.), 7.43 (t, 1H, J=7.8 Hz), 7.58 (m, 1H), 7.65 (t, 2H, J=7.2 Hz), 7.76-7.82 (m, 2H), 8.07 (d, 1H, J=8.4 Hz), 8.09-8.13 (m, 3H), 8.23 (d, 1H, J=8.4 Hz), 8.31 (d, 1H, J=8.4 Hz), 9.09 (m, 1H), 9.17 (m, 1H). $^{13}$C NMR (151 MHz, acetone-$d_6$) δ 27.42, 28.02, 38.46, 62.58, 68.02, 106.06, 106.69, 111.77, 112.29, 113.45, 119.09, 123.85, 124.04, 124.85, 127.44, 128.03, 130.11, 130.74, 131.92, 132.59, 133.47, 134.93, 140.19, 142.87, 147.48, 148.34, 151.46, 154.21. HR-MS (ESI) m/z: calcd for $C_{31}H_{29}N_6O$, [M1+H]$^+$=501.2397, found 501.2388. Anal. Calcd for $C_{31}H_{28}N_6O$: C, 74.38; H, 5.64; N, 16.79. Found: C, 74.53; H, 5.71; N, 16.61.

Step 4: Synthesis of 3-(2-Methyl-6-((E)-(4-((E)-phenyldiazenyl)naphthalen-1-yl)diazenyl)-2,3-dihydro-1H-perimidin-2-yl)propyl 5-((3aR,4R,6aS)-2-oxohexahydro-1H-thieno[3,4-d]imidazol-4-yl)pentanoate (18)

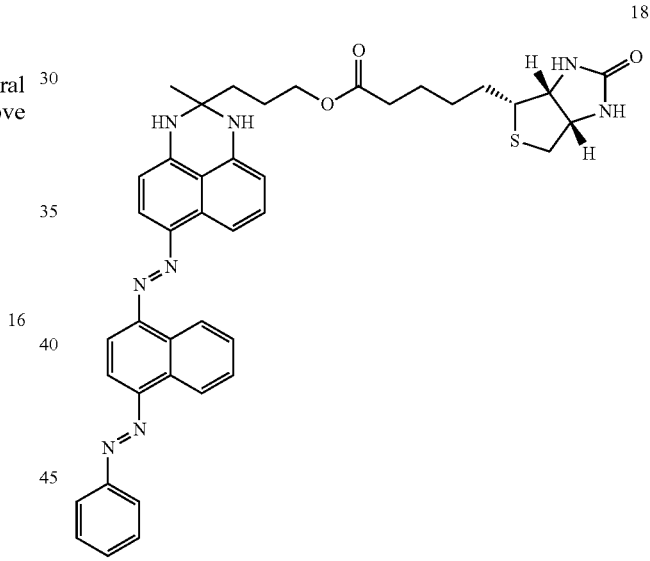

18

This compound was prepared according to the general procedure described in respect of Step 4 of Example 1 above, upon reaction of D-biotin with alcohol 16. The crude product was purified by column chromatography using a mixture of dichloromethane/methanol (from 100/1 up to 100/6, v/v) as the eluent to provide pure 18 as a black solid, in 72% yield. Mp 149-151° C. $^1$H NMR (600 MHz, acetone-$d_6$) δ 1.35-1.45 (m, 2H), 1.50-1.62 (m, 6H), 1.65-1.74 (m, 1H), 1.85-1.97 (m, 4H), 2.23 (q, 2H, J=7.3 Hz), 2.66 (d, 1H, J=12.5 Hz), 2.80-2.84 (m, 1H), 3.10-3.15 (m, 1H), 4.02-4.10 (m, 2H), 4.21-4.27 (m, 1H), 4.39-4.44 (m, 1H), 5.74 (brs, 1H, $D_2O$ exch.), 5.79 (brs, 1H, $D_2O$ exch.), 6.07 (brs, 0.5H, $D_2O$ exch.), 6.09 (brs, 0.5H, $D_2O$ exch.), 6.64 (d, 1H, J=7.4 Hz), 6.69 (d, 1H, J=8.5 Hz), 7.12 (brs, 0.5H, $D_2O$ exch.), 7.16 (brs, 0.5H, $D_2O$ exch.), 7.43 (t, 1H, J=7.6 Hz), 7.58 (m, 1H), 7.65 (t, 2H, J=7.8 Hz), 7.76-7.82 (m, 2H), 8.06 (d, 1H, J=8.4 Hz), 8.09-8.13 (m, 3H), 8.22 (dd, 1H, J=8.4 Hz+1.6 Hz), 8.32 (d, 1H, J=8.3 Hz), 9.09 (m, 1H), 9.17 (m, 1H). $^{13}$C NMR (151 MHz, acetone-d$_6$) δ 24.29, 25.71, 27.39, 29.12, 29.19, 34.32, 37.99, 41.05, 56.56, 60.89, 62.49, 64.76, 68.03, 106.24, 106.85, 111.84, 111.94, 112.43, 113.59, 119.18, 124.01, 124.19, 125.00, 127.69, 128.26, 130.36, 130.88, 132.19, 132.77, 133.63, 135.07, 140.34, 143.00, 147.74, 148.51, 151.66, 154.46, 163.78, 173.75. HR-MS (ESI) m/z: calcd for C$_{41}$H$_{43}$N$_8$O$_3$S, [M1+H]$^+$=727.3173, found 727.3164. Anal. Calcd for C$_{41}$H$_{42}$N$_8$O$_3$S: C, 67.75; H, 5.82; N, 15.42. Found: C, 67.64; H, 5.78; N, 15.50.

Example 7

Synthesis of 4-((E)-(4-((E)-(2,2-Dimethyl-2,3-dihydro-1H-perimidin-6-yl)diazenyl)naphthalen-1-yl)diazenyl)phenethyl 5-((3aR,4R,6aS)-2-oxohexahydro-1H-thieno[3,4-d]imidazol-4-yl)pentanoate (24)

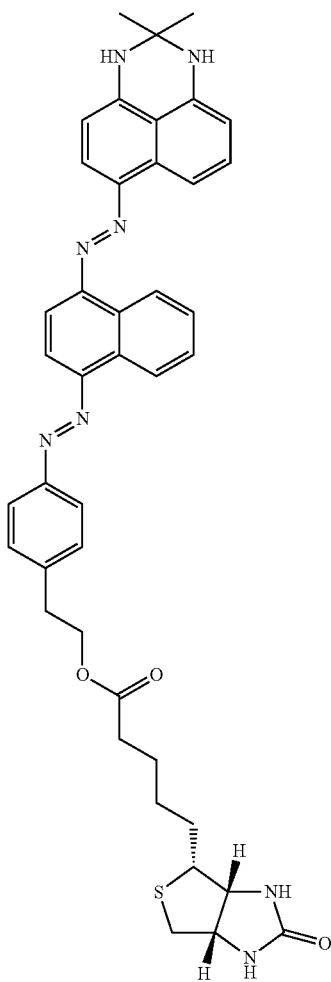 [SMILES: CC1(C)Nc2cccc3c(/N=N/c4ccc(/N=N/c5ccc(CCOC(=O)CCCC[C@H]6SC[C@H]7NC(=O)N[C@H]76)cc5)c5ccccc45)ccc(c23)N1]

Step 1: Synthesis of 2,2-Dimethyl-2,3-dihydro-1H-perimidine (30)

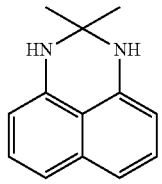

A solution of 1,8-diaminonaphthalene (6, 4 g, 25.28 mmol) in acetone (14 mL) was stirred at room temperature for 4 days. Upon completion of the reaction, the solvent was evaporated under reduced pressure, diethylether (40 mL) was added into the oily residue and evaporated, causing the crystallization of the perimidine 30. By this procedure 5 g of the perimidine 16 were obtained, as a beige solid. Yield 100%. Mp 114-116° C. (Ref. 115-116° C.) (Zhang & Zhang, 2007). $^1$H NMR (600 MHz, CDCl$_3$) δ 1.46 (s, 6H), 4.14 (brs, 2H, D$_2$O exch.), 6.48 (d, 2H, J=7.3 Hz), 7.19 (d, 2H, J=7.9 Hz), 7.27 (t, 2H, J=7.4 Hz+8.1 Hz). $^{13}$C NMR (151 MHz, CDCl$_3$) δ 28.80, 64.62, 106.06, 113.05, 117.14, 127.12, 134.70, 140.34.

Step 2: Synthesis of (E)-2-(4-((4-Aminonaphthalen-1-yl)diazenyl)phenyl)ethanol (22)

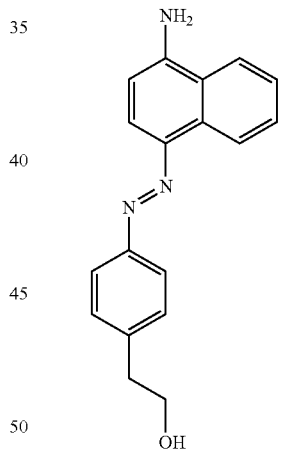

2-(4-Aminophenyl)ethanol (21, 4 g, 29.16 mmol) was added into a mixture of H$_2$O (12 mL) and HCl (10N, 6.4 mL) at 0° C. followed by dropwise addition of an aqueous solution (6 mL) of NaNO$_2$ (2.21 g, 32.03 mmol) over a period of 10 minutes and then this mixture was stirred at 0° C. for 100 minutes. Then 0.6 g of sodium acetate trihydrate was added to the solution and stirring was continued for 15 more minutes. This solution of the diazonium salt was added dropwise into a suspension of 1-naphthylamine (4.15 g, 29 mmol) in a mixture of H$_2$O (80 mL), EtOH (9 mL) and HCl (10N, 3 mL) over a period of 30 minutes. The deep purple colored suspension was stirred at 0° C. for 90 minutes and then at room temperature for 16 hours. The solution was then neutralized with addition of saturated aqueous solution of NaHCO$_3$ and the resulting precipitate was filtered under vacuum, washed with H₂O adequately and air dried. The crude product was purified by column chromatography using a mixture of dichloromethane/ethyl acetate (from 100/5 up to 100/25, v/v) as the eluent to provide 5.2 g of 22 as an orange colored solid. Yield 62%. Mp 110-2° C. ¹H NMR (600 MHz, DMSO-d6) δ 2.81 (t, 2H, J=6.9 Hz), 3.67 (q, 2H, J=6.9 Hz+5.5 Hz), 4.69 (t, 1H, D₂O exch., J=5.3 Hz), 6.77 (d, 1H, J=8.5 Hz), 6.85 (brs, 2H, D₂O exch.), 7.38 (d, 2H, J=8.1 Hz), 7.48 (t, 1H, J=7.8 Hz+7.3 Hz), 7.62 (t, 1H, J=7.9 Hz+7.3 Hz), 7.80 (d, 2H, J=8.1 Hz), 7.88 (d, 1H, J=8.5 Hz), 8.20 (d, 1H, J=8.5 Hz), 8.90 (d, 1H, J=8.5 Hz). ¹³C NMR (151 MHz, DMSO-d6) δ 38.82, 62.01, 107.31, 114.78, 121.23, 121.76, 122.61, 122.72, 124.28, 127.29, 129.72, 133.14, 136.84, 141.16, 149.96, 151.60.

Step 3: Synthesis of 2-(4-((E)-(4-((E)-(2,2-dimethyl-2,3-dihydro-1H-perimidin-6-yl)diazenyl)naphthalen-1-yl)diazenyl)phenyl)ethanol (23)

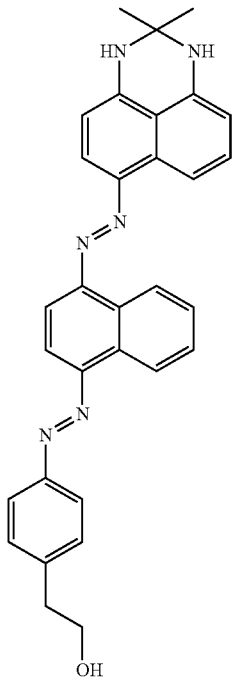

This compound was synthesized following an analogous procedure to that described in respect of Step 3 of Example 1 above, upon reaction of (E)-2-(4-((4-aminonaphthalen-1-yl)diazenyl)phenyl)ethanol (22) with perimidine 30. The crude product was purified by column chromatography using a mixture of dichloromethane/ethyl acetate (from 100/1 up to 100/10, v/v) as the eluent to provide pure alcohol 23 as a black solid, in 67% yield. Mp 249-252° C.(decomp.). ¹H NMR (600 MHz, DMSO-d6) δ 1.48 (s, 6H), 2.86 (t, 2H, J=6.9 Hz), 3.71 (q, 2H, J=6.9 Hz+5.1 Hz), 4.74 (t, 1H, D₂O exch., J=5.1 Hz), 6.56 (d, 1H, J=6.9 Hz), 6.60 (d, 1H, J=8.6 Hz), 6.78 (brs, 1H, D₂O exch.), 7.43 (t, 1H, J=8.1 Hz+7.7 Hz), 7.48 (d, 2H, J=8.4 Hz), 7.76-7.83 (m, 2H), 7.96-8.02 (m, 5H), 8.17 (d, 1H, J=8.9 Hz), 8.20 (d, 1H, J=8.6 Hz), 9.00 (m, 1H), 9.09 (m, 1H). ¹³C NMR (151 MHz, DMSO-d6) δ 28.27, 38.89, 61.82, 64.59, 105.07, 105.52, 109.82, 109.95, 111.21, 112.64, 119.12, 122.78, 123.02, 123.77, 126.83, 127.45, 130.01, 130.27, 130.99, 131.94, 133.51, 138.25, 142.28, 143.83, 145.83, 147.82, 149.95, 151.38. HR-MS (ESI) m/z: calcd for C₃₁H₂₉N₆O, [M1+H]⁺=501.2397, found 501.2391. Anal. Calcd for C₃₁H₂₈N₆O: C, 74.38; H, 5.64; N, 16.79. Found: C, 74.47; H, 5.68; N, 16.69.

Step 4: Synthesis of 4-((E)-(4-((E)-(2,2-Dimethyl-2,3-dihydro-1H-perimidin-6-yl)diazenyl)naphthalen-11-yl)diazenyl)phenethyl 5-((3aR,4R,6aS)-2-oxo-hexahydro-1H-thieno[3,4-d]imidazol-4-yl)pentanoate (24)

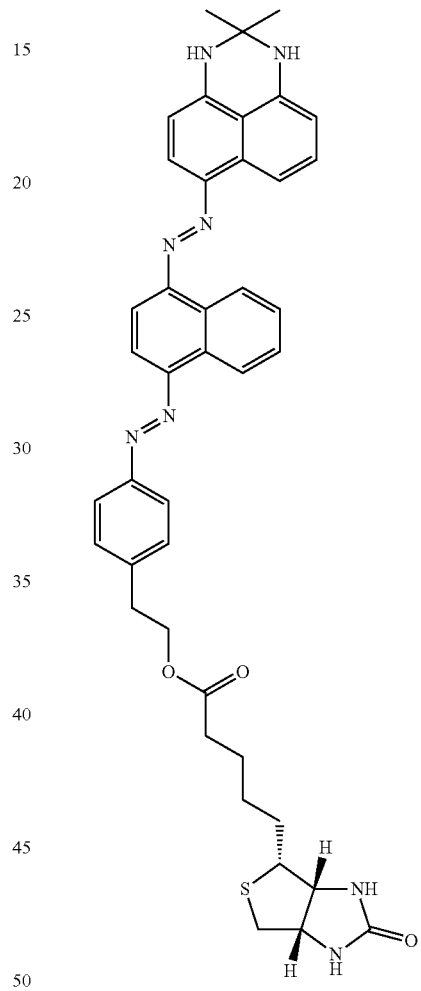

This compound was synthesized following an analogous procedure to that described in respect of Step 4 of Example 1 above, upon reaction of alcohol 23 with D-biotin. The crude product was purified by column chromatography, using a mixture of dichloromethane/methanol (from 100/0 up to 100/6, v/v) as the eluent to provide 24 as a black solid, in 62% yield. Mp 173-5° C. ¹H NMR (600 MHz, acetone-d6) δ 1.36-1.43 (m, 2H), 1.55-1.65 (m, 9H), 1.68-1.77 (m, 1H), 2.32 (t, 2H, J=7.4 Hz), 2.65 (d, 1H, J=12.5 Hz), 2.86 (dd, 1H, J=12.5 Hz+5.1 Hz), 3.09 (t, 2H, J=6.7 Hz), 3.12-3.16 (m, 1H), 4.26-4.29 (m, 1H), 4.36-4.42 (m, 3H), 5.66 (brs, 1H, D₂O exch.), 5.79 (brs, 1H, D₂O exch.), 6.03 (brs, 1H, D₂O exch.), 6.62 (d, 1H, J=7.4 Hz), 6.65 (d, 1H, J=8.5 Hz), 7.04 (brs, 1H, D₂O exch.), 7.43 (t, 1H, J=7.8 Hz), 7.55 (d, 2H, J=8.4 Hz), 7.75-7.81 (m, 2H), 8.04-8.08 (m, 3H), 8.10 (d, 1H, J=8.4 Hz), 8.22 (d, 1H, J=8.4 Hz), 8.33 (d, 1H, J=8.4 Hz), 9.09 (m, 1H), 9.17 (m, 1H). $^{13}$C NMR (151 MHz, acetone-d6) δ 25.78, 28.85, 29.29, 34.51, 35.73, 41.09, 56.53, 60.84, 62.49, 64.95, 66.03, 106.21, 106.90, 111.95, 112.11, 112.45, 113.51, 119.03, 124.13, 124.23, 124.97, 127.67, 128.22, 130.77, 130.98, 132.78, 133.57, 135.11, 140.38, 143.10, 143.31, 147.82, 148.46, 151.53, 153.21, 163.70, 173.66. HR-MS (ESI) m/z: calcd for $C_{41}H_{42}N_8O_3SNa$, $[M1+Na]^+$=749.2993, found 749.2992; calcd for $C_{41}H_{43}N_8O_3S$, $[M1+H]^+$=727.3173, found 727.3172. Anal. Calcd for $C_{41}H_{42}N_8O_3S$: C, 67.75; H, 5.82; N, 15.42. Found: C, 67.82; H, 5.87; N, 15.34.

Detection of Senescent Cells

General Information:

1. Biological Material

A wide range of biological materials that present senescence was utilized to assess the efficacy of the generated compounds to reveal such cells, in comparison to the commercially available SBB reagent. This material consisted of in vitro and in vivo models and clinical samples, known to exhibit robust cellular senescence, either by means of proliferative exhaustion (Replicative Senescence, RS) or upon stress induction (Premature or Stress Induced Senescence, SIPS), including oncogenic stress signals (Oncogene Induced Senescence, NS) (Georgakopoulou et al., 2013; Liakou et al., 2016; Galanos et al., 2016; Petrakis et al., 2016; Bartkova et al., 2006; Liontos et al., 2007; Liontos et al., 2009; Hellevik & Martinez-Zubiaurre, 2014). The employed senescence models were the following:

1.1 In Vitro Models

The in vitro models comprised seven cellular systems. The first one was primary human diploid lung fibroblasts (DLFs) at late passages, exhibiting replicative senescence and were compared to early proliferative passages devoid of senescence (Georgakopoulou et al., 2013; Liakou et al., 2016). The same cellular system was used at early passages that underwent SIPS upon y-irradiation and was compared in relation to non-irradiated counterparts. Another set of models comprised two inducible Saos2 Tet-ON osteosarcoma cell lines carrying p53 and $p21^{WAF1/Cip1}$, respectively, two well established effectors of senescence (Georgakopoulou et al., 2013; Galanos et al., 2016). Finally, the U2OS-E2F1 ER, U2O5-Cdt1 Tet-ON and HBECs-Cdc6 Tet-ON inducible systems that undergo SIPS due to oncogenic stress signals were also utilized (Petrakis et al., 2016; Liontos et al., 2007; Liontos et al., 2009). Parental cell lines were obtained either directly from ATCC or from collaborating laboratories that generated them. In addition, the human cancer cell line HeLa and near normal Li-Fraumeni fibroblasts (Galanos et al., 2016) were also employed as control cell lines for the specificity of staining of the SBB compounds.

1.2 In Vivo Models

The in vivo material included tissues from three mouse models and three human clinical settings.

1.2.1 Animal Models

In the first mouse model, the K-ras$^{V12}$ oncogene is conditionally activated in the lung, generating adenomas (pre-neoplastic lesions) and adenocarcinomas, as previously reported (Collado et al., 2005). Senescence occurs in adenoma cells, as an anti-tumor barrier (Bartkova et al., 2006), while in adenocarcinomas it is bypassed and therefore not detected (Georgakopoulou et al., 2013; Collado et al., 2005).

Secondly, a mouse model of bleomycin induced pneumopathy was generated, as previously described (Aoshiba et al., 2013). In brief, C57BL/6 mice were intratracheally injected with 30 ul of PBS or with 30 ul of a solution containing 2.5 mg/kg (mouse weight) of bleomycin. Two weeks later mice were sacrificed and lungs were collected, fixed and embedded in paraffin blocks. Bleomycin administration is well known to induce at initial stages robust senescence in alveolar epithelial cells, while prolonged treatment (over two weeks) results in gradual interstitial lung fibrosis as a consequence of a SASP (Senescence Associated Secretory Phenotype) phenomenon (Aoshiba et al., 2013).

The third mouse model is a xenograft one, in which tumors were generated by the subcutaneous injection of 1E-6 Mel9 human melanoma cells in athymic nude mice. After tumor development, mice were injected intravenously (everyday, for 2 weeks) with 200 ul vehicle or with 200 ul of a solution containing 50 mg/kg palbociclib (Pfizer). Palbociclib acts as a Cdk4/6 inhibitor that has been recently demonstrated to inhibit melanoma progression through senescence induction (Yoshida et al., 2016).

1.2.2 Human Clinical Samples

The clinical settings used in the current study included tissue samples from patients suffering from head/neck (Evangelou et al., 2013) and breast carcinomas that were irradiated to achieve shrinkage of the tumors prior to surgery. Irradiation is well established to induce senescence either in vitro (in cells isolated from solid tumors) or in vivo affecting different cellular compartments of solid tumors, including cancer associated fibroblasts (CAFs) (Liakou et al., 2016; Hellevik & Martinez-Zubiaurre, 2014; Gewirtz, 2014). In the case of irradiated breast tumors we recently demonstrated that ionizing radiation provokes premature senescence of stromal fibroblasts in vivo (Liakou et al., 2016). Corresponding non-irradiated cases served as negative controls. The third model employed, consisted of a set of congenital nevi. These melanocytic lesions are well known to exhibit robust senescence as an antitumor barrier, induced via activation of the DNA damage response (Halazonetis et al., 2008; Michaloglou et al., 2005). We also included in the analysis a limited number of cases of melanomas that developed either on pre-existing or in the vicinity of congenital nevi. This is a very useful tool since, as previously described, when senescence is bypassed in melanoma cells (Michaloglou et al., 2005), no evidence of senescent markers expression is obtained. In this setting, we were able to evaluate and directly compare the staining results in a positive for senescence preoneoplastic lesion (congenital nevi) and in neoplastic lesion (melanoma), negative for senescence, as both conditions were located in the same tissue section. Generally, all findings were always compared to the corresponding adjacent normal epidermis relative to the location of melanocytes.

A set of reference tissues were also employed for the initial screening to reveal among the new generated chemical compounds those with the most optimal performance for senescence detection. These tissues are known to exhibit high cellular content of lipofuscin that makes them ideal in vivo positive controls and were obtained from:

i. Liver Tissue from Young and Aged Patients.

Liver tissue from five (three male and two female) and seven (four male and three female) specimens from young and old individuals respectively, were analyzed. Age of young patients ranged from 18-23 years, while the corresponding one for old patients was 66-80 years. The material consisted of two surgical segments and three biopsies for the young cases while the corresponding one for the old cases included three surgical segments and four biopsies. For the young individuals the material was obtained in the frame of non pathological conditions (liver transplantation donors and surgical manipulations to deal with abdominal injury). Liver tissues from old individuals came from the surgical margins of hepatectomy segments and biopsies that were performed during clinical investigations.

ii. Seminal Vesicles Included in Prostatectomy Segments with Prostatic Cancer.

Tissues from patients with benign prostatic hyperplasia (BPH), a condition related to senescence were also employed (Castro et al., 2013). Adjacent normal prostatic glands served as negative controls.

Protocols for animal tissues and clinical sample collection, and their experimental use were approved by the Bio-Ethics Committee of Medical School of Athens, in accordance with the Declaration of Helsinki and local laws and regulations, following also written consent from the patients in the case of clinical samples.

2. General Staining Methods
2.1 Preparation of the Biological Material
2.1.1 Materials:
1. Cells (From Aspiration or Cell Culture)
2. Cover Slips
3. Various fixative media such as 100% Methanol, 100% Ethanol, and 1-5% (w/v) Paraformaldehyde/PBS Solution can be applied
4. 1-5% (w/v) Paraformaldehyde/PBS Solution: Dissolve 1-5 gr of Paraformaldehyde (PFH) in 100 ml of PBS in a glass beaker. Heat and stir the mixture until it becomes transparent. Let the solution to cool and adjust pH to 7.4.
5. Phosphate Buffered Saline (PBS; 10×): 1.37 M NaCl, 27 mM KCl, 100 mM $Na_2HPO_4$, 18 mM $KH_2PO_4$, pH 7.4
6. Incubation Chambers for Cover Slips
7. Tissue samples (Fixed in 10% Buffered Formalin Solution and Paraffin Embedded, FFPE)
8. 10% Buffered Formalin Solution (Sigma-Aldrich)
9. 1% (v/v) formaldehyde/PBS: Add in a volumetric cylinder, of appropriate size, 10 ml of Buffered Formalin Solution 10%, adjust volume to 100 ml with PBS and stir at room temperature (RT). Store at 4° C.
10. Positively Charged Glass Slides
11. Coplin Jars
12. Glass Beaker
13. Volumetric Cylinder
14. Thin edged Forceps 2.1.2 Procedures:
1. Cells. Mount cells on cover slips and fix them in 1-5% (w/v) paraformaldehyde/PBS solution for 5 min at RT. Then wash three times (approx. 1 min) with PBS.
2. Tissue samples (FFPE sections): Cut thin paraffin sections and mount them on positively charged glass slides. Incubate at 37° C. overnight. Store at room temperature (RT) until staining.

2.2. General Preparation of the Compound (LG13) Solution
2.2.1 Substances:
1. Compound (LG13)
2. 100% ethanol (100% EtOH)
3. Parafilm
4. Fritted glass filter of medium porosity
5. Airtight Dye Container 2.2.2 General Procedure:
1. Dissolve 40 mg of the compound (LG13) in 7.4 ml 100% EtOH in a glass beaker and cover it with parafilm.
2. Incubate at 56° C. in a waterbath for 120 min until the compound is completely dissolved.

2.3. General Method for Compound (LG13) Staining
2.3.1 Materials:
1. Xylene
2. Gradually Decreased (96%, 80%, 70%, 50%) EtOH Solutions
3. Syringe
4. 13 mm filter, membrane 0.22 μm
5. Soft paper (dry or dipped in ethanol)
6. Anti-biotin antibody ([Hyb-8] ab201341, Abcam)
7. Ultravision Quanto Detection System HRP DAB kit (Cat no: TL-125-QHD)
8. Glycerol (Sigma-Aldrich)
9. Tris Buffered Saline (TBS; 10×): 1.5 M NaCl, 0.1 M Tris-HCl, pH 7.4. Store at 4° C.
10. 0.5% Triton X/TBS: 0.5 ml Triton X diluted in 99.5 ml TBS
11. Mounting media Glycergel (DakoCytomation).
12. Light Microscope
13. Anti-p21$^{WAF1/Cip1}$ mouse primary antibody [(F-5)(sc-6246) Santa-Cruz]
14. Anti-p16$^{INK4A}$ mouse primary antibody [(sc-74401) Santa-Cruz]
15. Anti-Ki67 rabbit polyclonal antibody [ab16667, Abcam]
16. Secondary goat anti-mouse antibody Alexa Fluor 568 conjugated [Thermo Fisher Scientific (Cat no: A-11004)]
17. DAPI (4',6-Diamidino-2-Phenylindole, Dihydrochloride) [Thermo Fisher Scientific (Cat no: D1306)]
18. Fluorescence microscope 2.3.2 General Procedures:
2.3.2.1 General Staining Protocol for Cells Mounted on Coverslips
1. Wash ×1 in TBS for 5 min at RT.
2. Block the endogenous hydrogen peroxidase, using the UltraVision Hydrogen Peroxide Block included in the Ultravision Quanto Detection System HRP DAB kit (Cat no: TL-125-QHD) for 10 min at RT and in dark conditions.
3. Wash ×2 in TBS for 30 sec and ×1 for 5 min at RT.
4. Wash ×1 in EtOH 50% for 5 min at RT.
5. Wash ×1 EtOH 70% for 5 min at RT.
6. Incubate with the compound (LG13) at RT. A drop of freshly prepared compound (LG13) is placed on a clean slide with the use of a syringe that carried a 45 μm filter (see also FIG. 1 from Evangelou & Gorgoulis, 2016). Then the cover-slip with the cells is turned down (using thin edged forceps) on the slide and attached on the dye drop in a way that the material faces down the drop on the slide, (see also FIG. 1 from Evangelou & Gorgoulis, 2016).
7. The staining reaction is monitored under the light microscope until detection of the signal (average time 5-8 min).
8. Wash ×2 in EtOH 50%.
9. Repeat washing ×2 in fresh EtOH 50%.
10. Wash ×2 in TBS for 30 sec and ×1 for 5 min at RT.
11. Incubate with 0.5% Triton X/TBS for 3 min at RT.
12. Wash ×1 in TBS for 5 min at RT.
13. Incubate with the primary anti-biotin antibody diluted 1:500 in TBS ([Hyb-8] ab201341, Abcam) for 60 min at 37° C.
14. Wash ×3 in TBS for 5 min at RT.
15. Incubate with the Primary antibody amplifier Quanto included in the Ultravision Quanto Detection System HRP DAB kit (Cat no: TL-125-QHD), for 10 min at RT.
16. Wash ×3 in TBS for 5 min at RT.
17. Incubate with the HRP Polymer Quanto included in the Ultravision Quanto Detection System HRP DAB kit (Cat no: TL-125-QHD), for 10 min at RT.

18. Wash ×2 in TBS for 30 sec and ×1 for 5 min at RT.
19. Application of DAB Plus Chromogen diluted ⅟300 in DAB Plus Substrate [Ultravision Quanto Detection System HRP DAB kit (Cat no: TL-125-QHD)]. The staining reaction is monitored under the light microscope until detection of the dark brown signal (average time 30 sec-1 min) at RT 1.
20. Wash in tap water for 5 min at RT.
21. Counterstain with Hematoxylin diluted 1:4 in deionized water
22. Wash in tap water for 5 min at RT.
23. Apply permanent mounting media Glycergel (DakoCytomation).
24. Observation under the light microscope.

2.3.2.2. General Staining Protocol for Tissue Sections Mounted on Glass Slides

1. Deparaffinize Sections by:
    a. Incubation at 60° C. for 30 min.
    b. Washing in Xylene for 15 min at RT.
2. Gradual Rehydration in:
    a. EtOH 100% for 15 min at RT.
    b. EtOH 96% for 10 min at RT.
    c. EtOH 80% for 5 min at RT.
    d. EtOH 70% for 3 min at RT.
    e. EtOH 50% for 3 min at RT.
3. Wash ×1 in TBS for 5 min at RT.
4. Block endogenous hydrogen peroxidase, using the UltraVision Hydrogen Peroxide Block included in the Ultravision Quanto Detection System HRP DAB kit (Cat no: TL-125-QHD) for 10 min at RT and in dark conditions.
5. Wash ×2 in TBS for 30 sec and ×1 for 5 min at RT.
6. Wash ×1 in EtOH 50% for 5 min at RT.
7. Wash ×1 EtOH 70% for 5 min at RT.
8. Incubate with the compound (LG13) at RT. A drop of freshly prepared compound (LG13) is placed on a clean slide with the use of a syringe that carrying a 2 mm filter (see also FIG. 1 from Evangelou & Gorgoulis, 2016). Then the cover-slip with the cells is turned down (using thin edged forceps) on the slide and attached on the dye drop in a way that the material faces down the drop on the slide, (see also FIG. 1 from Evangelou & Gorgoulis, 2016).
9. The staining reaction is monitored under the light microscope until detection of the signal (average time 5-8 min).
10. Wash ×2 in EtOH 50%.
11. Repeat ×2 in fresh EtOH 50%.
12. Wash ×2 in TBS for 30 sec and ×1 for 5 min at RT.
13. Incubate with 0.5% Triton X/TBS for 3 min at RT.
14. Wash ×1 in TBS for 5 min at RT.
15. Incubate with the primary anti-biotin antibody diluted 1:500 in TBS ([Hyb-8] ab201341, Abcam) for 60 min at 37° C.
16. Wash ×3 in TBS for 5 min at RT.
17. Incubate with the Primary antibody amplifier Quanto included in the Ultravision Quanto Detection System HRP DAB kit (Cat no: TL-125-QHD), for 10 min at RT.
18. Wash ×3 in TBS for 5 min at RT.
19. Incubate with the HRP Polymer Quanto included in the Ultravision Quanto Detection System HRP DAB kit (Cat no: TL-125-QHD), for 10 min at RT.
20. Wash ×2 in TBS for 30 sec and ×1 for 5 min at RT.
21. Apply DAB Plus Chromogen diluted ⅟300 in DAB Plus Substrate [Ultravision Quanto Detection System HRP DAB kit (Cat no: TL-125-QHD)]. The staining reaction was monitored under the light microscope until detection of the dark brown signal (average time 30 sec-1 min) at RT.
22. Wash in tap water for 5 min at RT.
23. Counterstain with Hematoxylin diluted 1:4 in deionized water.
24. Wash in tap water for 5 min at RT.
25. Apply permanent mounting media Glycergel (DakoCytomation).
26. Observation under the light microscope.

2.3.2.3. General Co-Staining Protocol for Cells Mounted on Coverslips

1. Wash ×1 in TBS for 5 min at RT.
2. Block the endogenous hydrogen peroxidase, using the UltraVision Hydrogen Peroxide Block included in the Ultravision Quanto Detection System HRP DAB kit (Cat no: TL-125-QHD) for 10 min at RT and in dark conditions.
3. Wash ×2 in TBS for 30 sec and ×1 for 5 min at RT.
4. Incubate with Ultra Protein Block included in the Ultravision Quanto Detection System HRP DAB kit (Cat no: TL-125-QHD) for 7 min in RT.
5. Wash ×1 in TBS for 5 min at RT.
6. Wash with 0.5% Triton X/TBS for 3 min at RT.
7. Wash ×1 in TBS for 5 min at RT.
8. Incubate with primary antibody.
9. Wash ×2 in TBS for 30 sec and ×1 for min RT.
10. Incubate with the Primary antibody amplifier Quanto included in the Ultravision Quanto Detection System HRP DAB kit (Cat no: TL-125-QHD), for 10 min at RT.
11. Wash ×3 in TBS for 5 min at RT.
12. Incubate with the HRP Polymer Quanto included in the Ultravision Quanto Detection System HRP DAB kit (Cat no: TL-125-QHD), for 10 min at RT.
13. Wash ×2 in TBS for 30 sec and ×1 for 5 min at RT.
14. Apply DAB Plus Chromogen diluted ⅟100 in DAB Plus Substrate [Ultravision Quanto Detection System HRP DAB kit (Cat no: TL-125-QHD)]. The staining reaction was monitored under the light microscope until detection of the dark brown signal (average time 30 sec-1 min) at RT.
15. Wash in tap water for 5 min at RT.
16. Wash ×1 in EtOH 50% for 5 min at RT.
17. Wash ×1 EtOH 70% for 5 min at RT.
18. Incubate with the compound (LG13) at RT. A drop of freshly prepared compound (LG13) is placed on a clean slide with the use of a syringe that carried a 2 mm filter (see also FIG. 1 from Evangelou & Gorgoulis, 2016). Then the cover-slip with the cells is turned down (using thin edged forceps) on the slide and attached on the dye drop in a way that the material faces down the drop on the slide, (see also FIG. 1 from Evangelou & Gorgoulis, 2016).
19. The staining reaction is monitored under the light microscope until detection of the signal (average time 5-8 min).
20. Wash ×3 in EtOH 50%.
21. Repeat washing ×3 in fresh EtOH 50%.
22. Wash ×2 in TBS for 30 sec and ×1 for 5 min at RT.
23. Incubate with the anti-biotin antibody diluted 1:500 in TBS ([Hyb-8] ab201341, Abcam) for 60 min at 37° C.
24. Wash ×3 in TBS for 5 min at RT.
25. Incubate with the secondary goat anti-mouse antibody AP conjugated (Invitrogen, Cat no: G21060) diluted 1:800 in TBS, for 60 min at RT.
26. Wash ×3 in TBS for 5 min at RT.
27. Wash ×2 in TBS for 30 sec and ×1 for 5 min at RT.
28. Application of NBT/BCIP substrate [dilute 1 tablet in 10 ml ddH$_2$O (Roche kit, Cat no: REF 11 697 471 001)] with the addition of 20 μl of 100 mM Levamisol. The staining reaction is monitored under the light microscope until detection of the dark blue signal (average time 5-7 min) at RT.
29. Wash ×2 in KTBT buffer for 5 min at RT
30. Wash ×2 in tap water for 5 min at RT.
31. Apply permanent mounting media Glycergel (DakoCytomation).
32. Observation under the light microscope.

2.3.2.4. General Co-Staining Protocol for Tissue Sections Mounted on Glass Slides
1. Deparaffinize sections by:
   a. Incubation at 60° C. for 30 min.
   b. Washing in Xylene for 15 min at RT.
2. Gradual rehydration in:
   a. EtOH 100% for 15 min at RT.
   b. EtOH 96% for 10 min at RT.
   c. EtOH 80% for 5 min at RT.
   d. EtOH 70% for 3 min at RT.
   e. EtOH 50% for 3 min at RT.
3. Wash ×1 in TBS for 5 min at RT.
4. Block endogenous hydrogen peroxidase, using the Ultra-Vision Hydrogen Peroxide Block included in the Ultravision Quanto Detection System HRP DAB kit (Cat no: TL-125-QHD) for 10 min at RT and in dark conditions.
5. Wash ×2 in TBS for 30 sec and ×1 for min at RT.
6. Blocking with Ultra V Block for 7 min at RT.
7. Wash ×1 in TBS for 5 min at RT.
8. Wash with 0.5% Triton X/TBS for 3 min at RT.
9. Wash ×1 in TBS for 5 min at RT.
10. Incubate with primary antibody.
11. Wash ×2 in TBS for 30 sec and ×1 for min RT.
12. Incubate with the Primary antibody amplifier Quanto included in the Ultravision Quanto Detection System HRP DAB kit (Cat no: TL-125-QHD), for 10 min at RT.
13. Wash ×3 in TBS for 5 min at RT.
14. Incubate with the HRP Polymer Quanto included in the Ultravision Quanto Detection System HRP DAB kit (Cat no: TL-125-QHD), for 10 min at RT.
15. Wash ×2 in TBS for 30 sec and ×1 for 5 min at RT.
16. Apply DAB Plus Chromogen diluted 1/300 in DAB Plus Substrate [Ultravision Quanto Detection System HRP DAB kit (Cat no: TL-125-QHD)]. The staining reaction was monitored under the light microscope until detection of the dark brown signal (average time 30 sec-1 min) at RT.
17. Wash in tap water for 5 min at RT.
18. Wash ×1 in EtOH 50% for 5 min at RT.
19. Wash ×1 EtOH 70% for 5 min at RT.
20. Incubate with the compound (LG13) at RT. A drop of freshly prepared compound (LG13) is placed on a clean slide with the use of a syringe attached to a 2 mm filter (see also FIG. 1 from Evangelou & Gorgoulis, 2016). Subsequently, the cover-slip with the cells is turned down (using thin edged forceps) on the slide and attached on the dye drop in a way that the material faces down the drop on the slide, (see also FIG. 1 from Evangelou & Gorgoulis, 2016).
21. The staining reaction is monitored under the light microscope until detection of the signal (average time 5-8 min).
22. Wash ×3 in EtOH 50%.
23. Repeat washing ×3 in fresh EtOH 50%.
24. Wash ×2 in TBS for 30 sec and ×1 for 5 min at RT.
25. Incubate with the anti-biotin antibody diluted 1:500 in TBS ([Hyb-8] ab201341, Abcam) for 60 min at 37° C.
26. Wash ×3 in TBS for 5 min at RT.
27. Incubate with the secondary goat anti-mouse antibody AP conjugated (Invitrogen, Cat no: G21060) diluted 1:800 in TBS, for 60 min at RT.
28. Wash ×3 in TBS for 5 min at RT.
29. Wash ×2 in TBS for 30 sec and ×1 for 5 min at RT.
30. Application of NBT/BCIP substrate [dilute 1 tablet in 10 ml ddH$_2$O (Roche kit, Cat no: REF 11 697 471 001)] with the addition of 20 µl of 100 mM Levamisol. The staining reaction is monitored under the light microscope until detection of the dark brown signal (average time 5-7 min) at RT.
31. Wash ×2 in KTBT buffer [KTBT buffer: dissolve 0.395 gr Tris-HCl, 0.43 gr NaCl and 0.03375 gr KCl in 1 lt double distilled water] for 5 min at RT.
32. Wash in tap water for 5 in at RT.
33. Wash in tap water for 5 min at RT.
34. Apply permanent mounting media Glycergel (DakoCytomation).
35. Observation under the light microscope.

Comparative Example 1

In the following comparative example 1 the histochemical dye SBB was used to detect senescent cells in tissue sections by the histochemical method previously described [Georgakopoulou et al, Aging (Albany N.Y.) 2013].

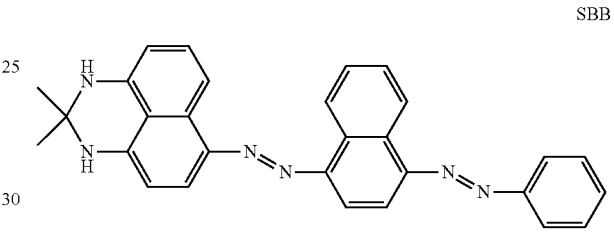

SBB

Tissue sections were obtained from paraffin embedded, formalin fixed: (a) irradiated human laryngeal tumors and (b) mouse lung adenomas, with established presence of senescent cells. Subsequently, they were immobilized on glass microscopy slides by standard procedures and processed as follows:
a. Deparaffinization for 5 min at room temperature in xylene.
b. Gradual rehydration in solutions of descending concentration of ethanol (100%, 80%, 70%, 50% v/v) and finally in TBS (Tris-buffered saline) or PBS (Phosphate-buffered saline) solution.
c. The SBB dye was diluted in 70% ethanol (v/v), filtered and then applied on tissue sections for 10 min.
d. Quick wash in 50% (v/v) ethanol.
e. Transfer and wash in TBS or PBS solution.
f. Counterstain with Hematoxylin or Nuclear Fast Red, followed by mounting with glycerol and sealed with a cover slip.
g. Microscopy observation.

Results from the application of the above described histochemical method are depicted in FIGS. 2a,b. Although senescent cells are clearly stained, the resolution of these cells require experienced pathologists. In addition, the necessity to have saturated ethanol-SBB solutions to achieve optimal performance for this staining process imposes practical difficulties during its application.

Comparative Example 2

In comparative example 2 the SBB histochemical dye was used to detect lipofuscin rich cells in tissue sections by the histochemical method previously described [Georgakopoulou et al, Aging (Albany N.Y.) 2013].

Tissue sections were obtained from paraffin embedded, formalin fixed: (a) human seminal vesicle and (b) human liver with steatohepatitis that have high content of lipofusin making them ideal reference (control) tissues to test the SBB assay. Subsequently, they were immobilized on glass microscopy slides by standard procedures and processed as follows:
 a. Deparaffinization for 5 min at room temperature in xylene.
 b. Gradual rehydration in solutions of descending concentration of ethanol (100%, 80%, 70%, 50% v/v) and finally in TBS (Tris-buffered saline) or PBS (Phosphate-buffered saline) solution.
 c. The SSB dye was diluted in 70% ethanol (v/v), filtered and then applied on tissue sections for 10 min.
 d. Quick wash in 50% (v/v) ethanol.
 e. Transfer and wash in TBS or PBS solution.
 f. Counterstain with Hematoxylin or Nuclear Fast Red, followed by mounting with glycerol and sealed with a cover slip.
 g. Microscopy observation.

Figure 3:
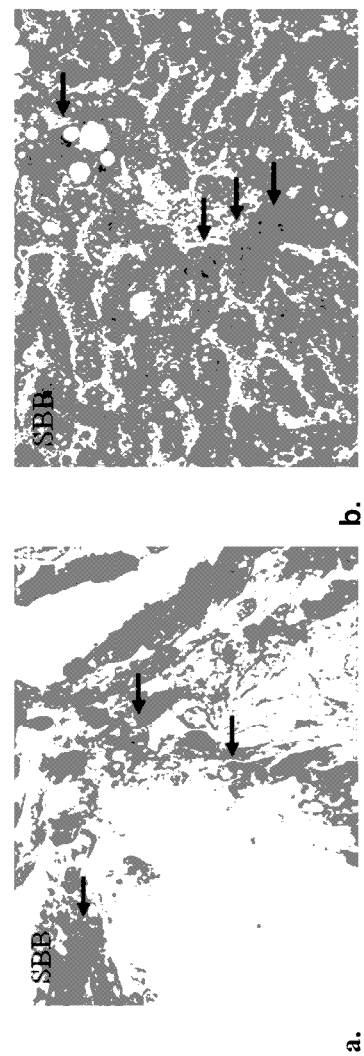
FIG. 3. Control experiments for lipofuscin detection using SBB staining in human (a) seminal vesicle and (b) liver with steatohepatitis, as reference tissues with high lipofuscin content. Arrows depict stained cells.

Results from the application of the above described histochemical method are depicted in FIG. 3.

Inventive Example 1

In inventive example 1 compounds of the general formula (5), prepared according to typical example 1 or 2, and specifically the linked with biotin derivative named as LG13 (2-methyl-6-((E)-(4-((E)-phenyldiazenyl)naphthalen-1-yl)diazenyl)-2,3-dihydro-1H-perimidin-2-yl)methyl 5-((3aR, 4R,6aS)-2-oxohexahydro-1H-thieno[3,4-d]imidazol-4-yl)pentanoate) was used to detect senescent cells in tissue sections by the same histochemical method used for SBB.

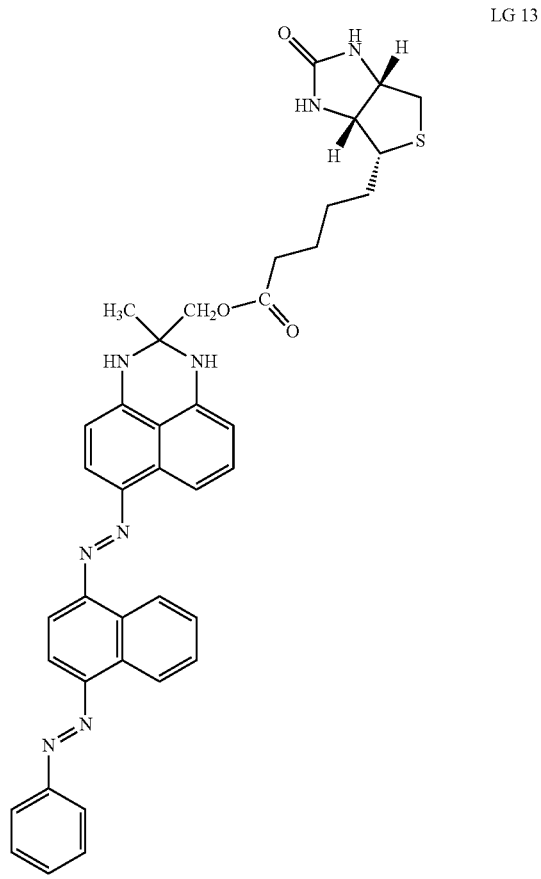

LG 13

Tissue sections were obtained from paraffin embedded, formalin fixed: (a) irradiated human laryngeal tumors and (b) mouse lung adenomas, with established presence of senescent cells. Subsequently, they were immobilized on glass microscopy slides by standard procedures and processed as follows:
 a. Deparaffinization for 5 min at room temperature in xylene.
 b. Gradual rehydration in solutions of descending concentration of ethanol (100%, 80%, 70%, 50% v/v) and finally in TBS (Tris-buffered saline) or PBS (Phosphate-buffered saline) solution.
 c. The LG13 new compound was diluted in 70% ethanol (v/v), filtered and then applied on tissue sections for 10 min.
 d. Quick wash in 50% (v/v) ethanol.
 e. Transfer and wash in TBS or PBS solution.
 f. Counterstain with Hematoxylin or Nuclear Fast Red, followed by mounting with glycerol and sealed with a cover slip.
 g. Microscopy observation.

Figure 4:
FIG. 4. Detection of senescent cells with histochemical staining using the new compound LG13, which is an SBB-analogue coupled with biotin, in tissue sections from (a) irradiated human laryngeal tumors and (b) mouse lung adenomas, with established presence of senescent. Arrows depict stained senescent cells.

Representative results from the application of this method are shown in FIGS. 4*a,b*. It should be noted that the above histochemical method using the novel SBB analogues does not encounter the ethanol solubility problems that the SBB stain exhibits in comparative example 1.

Figure 2:
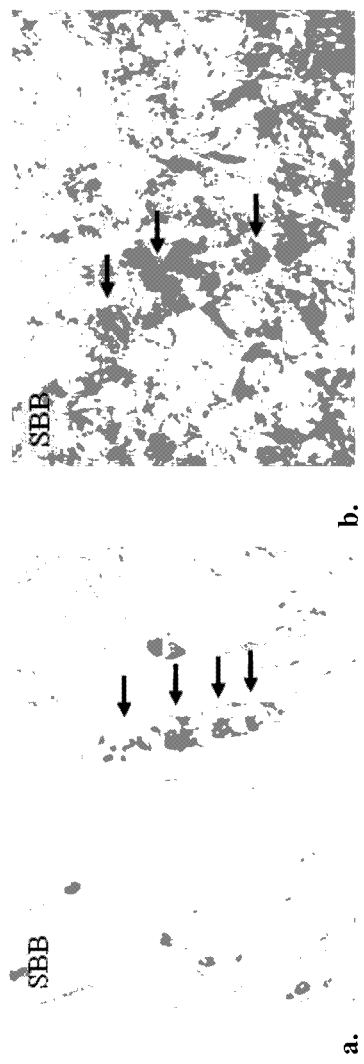
FIG. 2. Detection of senescent cells with SBB histochemical staining in tissue sections from (a) irradiated human laryngeal tumors and (b) mouse lung adenomas, with established presence of senescent cells, as a comparative example. Arrows depict stained senescent cells.

Use of the LG13 compound provides similar and even better resolution of senescent cells in biological samples as compared to the SBB staining, shown FIG. 2.

Inventive Example 2

In the inventive example 2, the derivative LG13 was used to detect senescent cells in tissue sections using streptavidin-horse radish peroxidase (HRP)/DAB labeling.

Tissue sections were obtained from paraffin embedded, formalin fixed: (a) irradiated human laryngeal tumors, (b) palbociclib treated human melanoma cell xenografts, (c) mouse bleomycin-injected lung and (d) mouse lung adenomas. Subsequently, they were immobilized on glass microscopy slides by standard procedures and processed as follows:
 a. Deparaffinization for 5 min at room temperature in xylene
 b. Gradual rehydration in solutions of descending concentration of ethanol (100%, 80%, 70%, 50% v/v) and finally in TBS (Tris-buffered saline) or PBS (Phosphate-buffered saline) solution.
 c. Blocking of endogenous peroxidase activity with 3% $H_2O_2$ for 10 min.
 d. Gradual dehydration of biopsy material in 50% (v/v) ethanol followed by 70% (v/v) ethanol for 5 min each step.
 e. Application of the new compound LG13, linked with biotin, diluted in ethanol and filtered, on biopsy material for 10 min.
 f. Quick wash in 50% (v/v) ethanol.
 g. Transfer and wash in TBS or PBS solution.
 h. Incubation in streptavidin-HRP (horse radish peroxidase) conjugated (dilution 1/200), for ½ hr at room temperature.
 i. Quick wash in TBS or PBS solution.
 j. Staining with 3,3'-Diaminobenzidine (DAB) solution (dilution 1/300 in TBS or PBS) for 1 min at room temperature.
 k. Counterstain with Hematoxylin or Nuclear Fast Red, followed by mounting with DPX or glycerol and sealed with a cover slip, respectively. The steps of this method differ from that of inventive example 1 (inclusion of steps c, d, h and j) as it exploits the presence of the conjugated hapten on LG13 compound, which in this case is biotin, thus increases the detection sensitivity.

l. Microscopy observation.

Representative results from the application of this method are shown in FIG. 5ai-di. Senescent cells are depicted by a clear dark-brown or blue color, as described in FIG. 1, due to the presence of the biotin coupled to the SBB analogues that is detected by the streptavidin-HRP/DAB complex.

Figure 5:
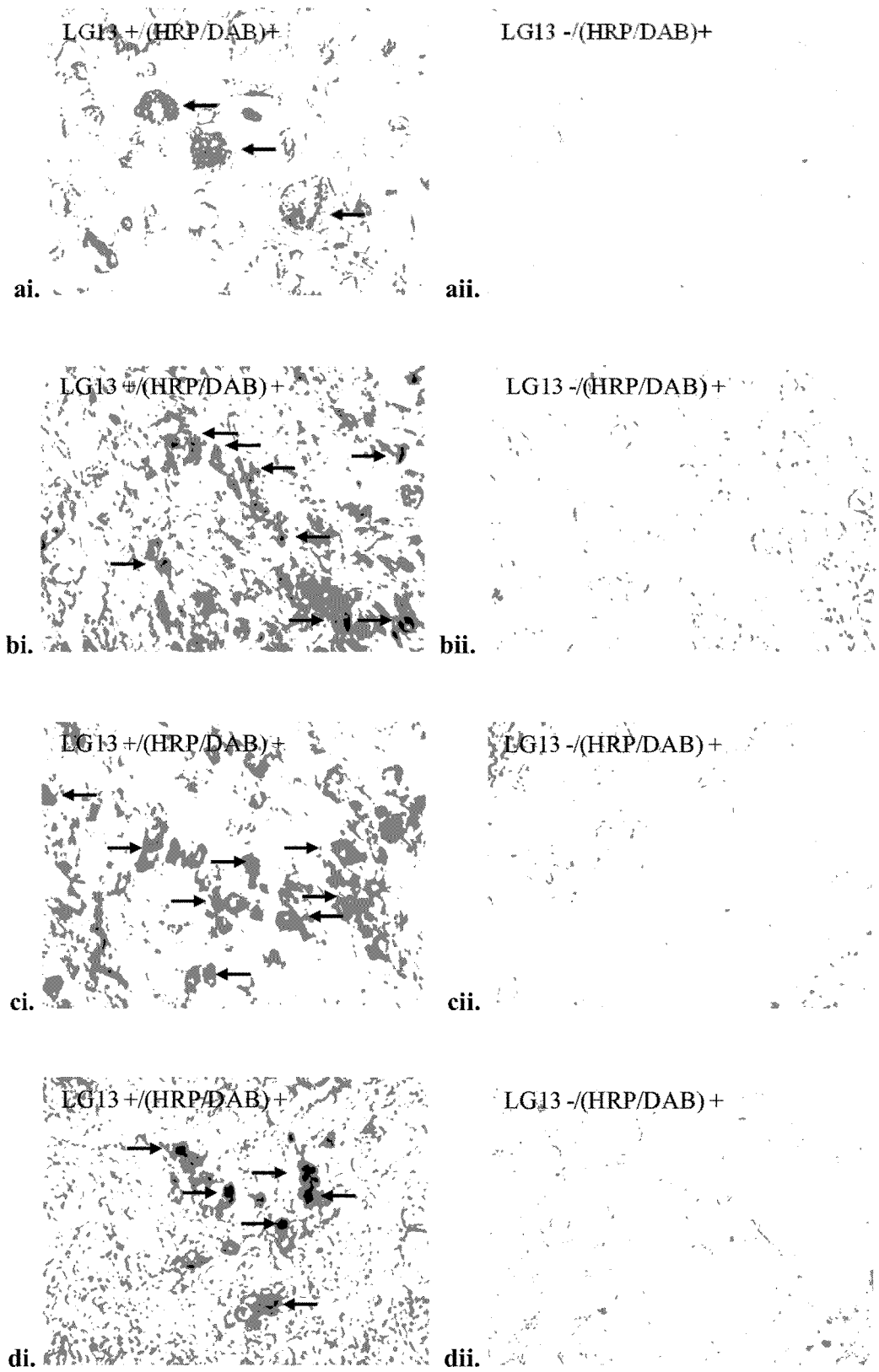
FIG. 5. Detection of senescent cells in tissue sections from (a) irradiated human laryngeal tumors, (b) palbociclib treated human melanoma cells xenografts, (c) mouse bleomycin-injected lung and (d) mouse lung adenomas, using the new compound LG13, reacting with the streptavidin-HRP/DAB complex due to the linked hapten, which is biotin in this case. Panels aii, bii, cii and dii represent application of the streptavidin-HRP/DAB complex without employing the new compound LG13 (control experiment for the specificity of the LG13 reaction in panels ai-di). Arrows depict stained senescent cells.

The linking of haptens, preferably biotin, permits even better visualization of senescent cells by applying conventional immunohistochemical-like staining, as the positive signal is amplified, especially in cases that may suffer partial striping of lipofuscin during the preparative steps. This method also exploits the better ethanol solubility of the SSB analogue compounds. This makes easier the recognition of senescent cells, as shown in FIG. 5ai-di in comparison to FIGS. 2,3,4, making this method a better choice for many researchers and non-researchers, avoiding experienced personnel, like pathologists. Panels aii-dii of FIG. 5 represent application of the streptavidin-HRP/DAB complex without use of the new compound LG13 representing control experiment for the specificity of the LG13 reaction in panels ai-di of FIG. 5.

Inventive Example 3

In inventive example 3, the derivative LG was used to detect senescent cells in cell spreads using streptavidin-horse radish peroxidase (HRP)/DAB labeling.

Induced and non-induced Saos2-p21$^{WAF1/Cip1}$ Tet-OFF cells as well as human lung fibroblasts (DLFs) non- and γ-irradiated were grown on cover slips and collected before and after the mentioned respective treatments for induction of senescence. Cover slips were treated as follows:

a. Fixation in ice-cold ethanol or methanol for 4 min.
b. Blocking of endogenous peroxidase activity with 3% $H_2O_2$ for 10 min.
c. Quick wash in 50% (v/v) ethanol.
d. Application of LG13 dye, diluted in ethanol and filtered, on cells for 10 min.
e. Quick wash in 50% (v/v) ethanol.
f. Transfer and wash in TBS or PBS solution.
g. Incubation in streptavidin-HRP (horse radish peroxidase) conjugated (dilution 1/200), for ½ hr at room temperature.
h. Quick wash in TBS or PBS solution.
i. Staining with 3,3'-Diaminobenzidine (DAB) solution (dilution 1/300 in TBS or PBS) for 1 min at room temperature.
j. Counterstain with Nuclear Fast Red, followed by mounting with glycerol and sealing with a cover slip.
k. Microscopy observation.

Figure 6:
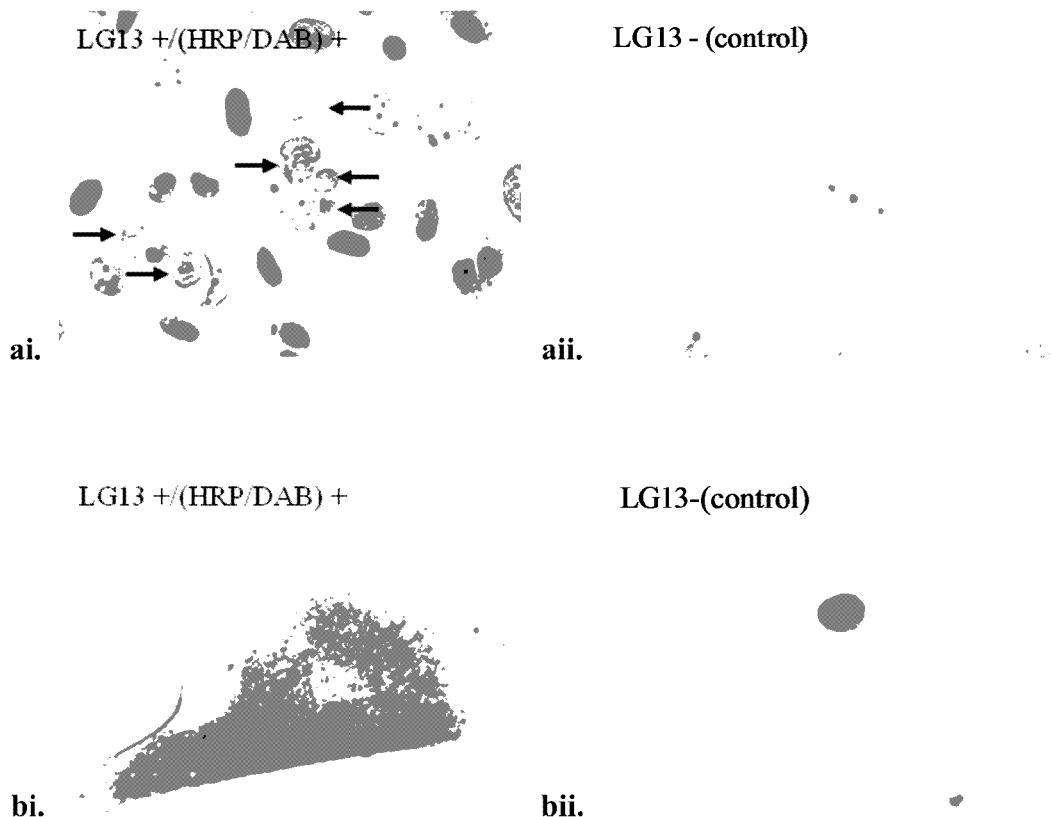
FIG. 6. Detection of senescent cells in (a) induced Saos2-p21 Tet-ON cells and (b) irradiated human diploid lung fibroblasts (DLFs), using the new compound LG13 reacting with the streptavidin-HRP/DAB complex due to the linked hapten, which is biotin in this case. Panels aii and bii represent application of the new compound LG13 in control experiment for the specificity of the reaction in panels ai and bi.

Results from the application of this method are depicted in FIG. 6. Senescent cells are depicted by a clear dark-brown color in panels 6ai and 6bi, as described in FIG. 1, due to the presence of the biotin coupled to LG13 that is detected by the streptavidin-HRP/DAB complex.

The improved ethanol solubility of such compounds and the ability to detect them by employing streptavidin-HRP/DAB complexes provides improved resolution. This makes easier the recognition of senescent cells, making this method a better choice for many researchers and non-researchers, avoiding experienced personnel, like pathologists. Panels 6aii and 6bii of FIG. 6 represent control experiment for the specificity of the LG13 reaction in panels ai-di of FIG. 6.

The overall ease of use of compounds like the LG13, in the above inventive examples, makes the methods related to its application ideal in the following fields: biomedical research, clinical/health care, cosmetics, male and female infertility/subfertillity, animal farming and the food industry. Routine detection of senescent cells can be achieved in single animal cells either derived from tissues of animal origin, (ranging from invertebrates to mammals, including humans) or in suspensions, body fluids and cell scrapes/smears, for example blood samples, urine specimens or cervical smears, or in laboratory culture, and in cells of plant origin. All these biological materials can be either in a fresh or preserved state (e.g. by physical or chemical means, such as freezing or formaldehyde treatment) as well as embedded in inert supportive material, like paraffin.

Inventive Example 4

In inventive example 4 the derivative compound LG13 was used to detect lipofuscin rich cells in tissue sections by the histochemical method previously described [Georgakopoulou et al, Aging (Albany N.Y.) 2013].

Tissue sections were obtained from paraffin embedded, formalin fixed: (a) human seminal vesicle and (b) human liver with steatohepatitis that have high content of lipofusin making them ideal reference (control) tissues to test the performance of the LG13 compound. Subsequently, they were immobilized on glass microscopy slides by standard procedures and processed as follows:

a. Deparaffinization for 5 min at room temperature in xylene.
b. Gradual rehydration in solutions of descending concentration of ethanol (100%, 80%, 70%, 50% v/v) and finally in TBS (Tris-buffered saline) or PBS (Phosphate-buffered saline) solution.
c. The SSB dye was diluted in 70% ethanol (v/v), filtered and then applied on tissue sections for 10 min.
d. Quick wash in 50% (v/v) ethanol.
e. Transfer and wash in TBS or PBS solution.
f. Counterstain with Hematoxylin or Nuclear Fast Red, followed by mounting with glycerol and sealed with a cover slip.
g. Microscopy observation.

Figure 7:
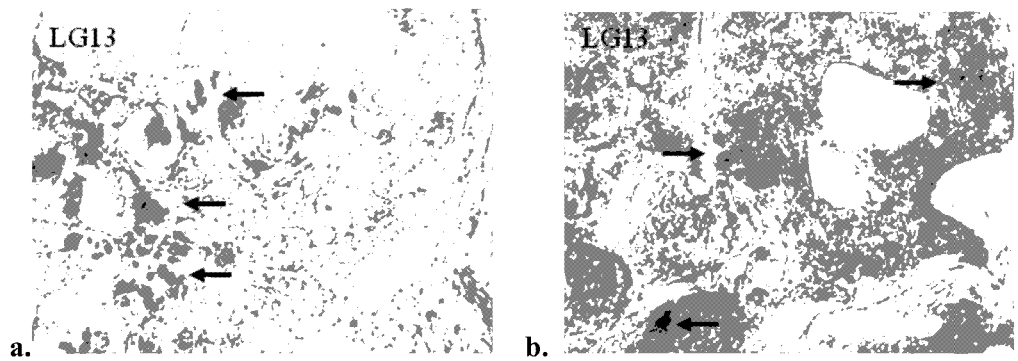
FIG. 7. Control experiments for lipofuscin detection using LG13 histochemical staining in human (a) seminal vesicle and (b) liver with steatohepatitis, as reference tissues with high lipofuscin content. Arrows depict stained cells.

Results from the application of the above described histochemical method are depicted in FIG. 7.

Inventive Example 5

In inventive example 5 the derivative LG13 was used to detect lipofuscin rich cells in tissue sections using streptavidin-horse radish peroxidase (HRP)/DAB labeling.

Tissue sections were obtained from paraffin embedded, formalin fixed: (a) human seminal vesicle and (b) human liver with steatohepatitis that have high content of lipofusin making them ideal reference (control) tissues to test the performance of the LG13 compound. Subsequently, they were immobilized on glass microscopy slides by standard procedures and processed as follows:

a. Deparaffinization for 5 min at room temperature in xylene
b. Gradual rehydration in solutions of descending concentration of ethanol (100%, 80%, 70%, 50% v/v) and finally in TBS (Tris-buffered saline) or PBS (Phosphate-buffered saline) solution.
c. Blocking of endogenous peroxidase activity with 3% $H_2O_2$ for 10 min.
d. Gradual dehydration of biopsy material in 50% (v/v) ethanol followed by 70% (v/v) ethanol for 5 min each step.
e. Application of the new compound LG13, linked with biotin, diluted in ethanol and filtered, on biopsy material for 10 min.

f. Quick wash in 50% (v/v) ethanol.
g. Transfer and wash in TBS or PBS solution.
h. Incubation in streptavidin-HRP (horse radish peroxidase) conjugated (dilution 1/200), for ½ hr at room temperature.
i. Quick wash in TBS or PBS solution.
j. Staining with 3,3'-Diaminobenzidine (DAB) solution (dilution 1/300 in TBS or PBS) for 1 min at room temperature.
k. Counterstain with Hematoxylin or Nuclear Fast Red, followed by mounting with DPX or glycerol and sealed with a cover slip, respectively. The steps of this method differ from that of inventive example 1 (inclusion of steps c, d, h and j) as it exploits the presence of the conjugated hapten on LG13 compound, which in this case is biotin, thus increases the detection sensitivity.
l. Microscopy observation.

Figure 8:
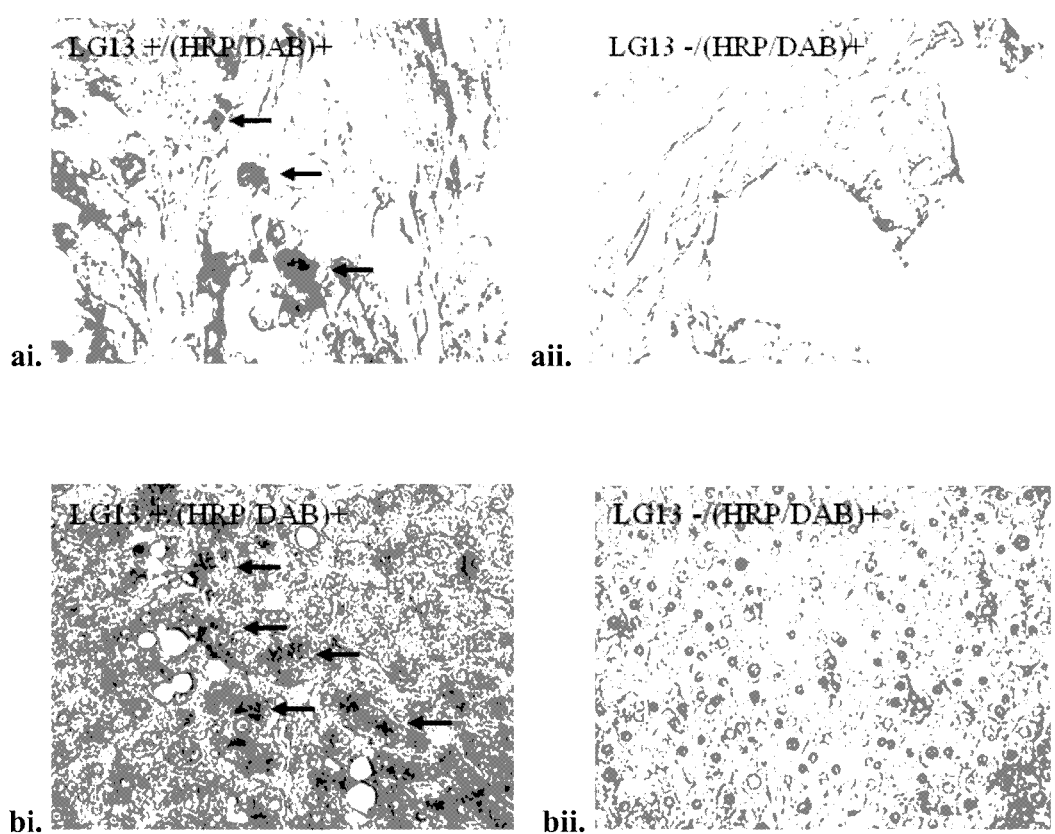
FIG. 8. Control experiments for lipofuscin detection using the new compound LG13, reacting with streptavidin-HRP/DAB complex in human (a) seminal vesicle and (b) liver with steatohepatitis, as reference tissues with high lipofuscin content. Panels aii and bii, represent application of the streptavidin-HRP/DAB complex without employing the new compound LG13 (control experiment for the specificity of the LG13 reaction in panels ai, bi). Arrows depict stained cells.

Representative results from the application of this method are shown in FIG. 8.

Inventive Example 6

In inventive example 6 the derivative LG13 was used to detect lipofuscin rich cells in cell spreads from cell culture by immunofluorescence staining.
Immunofluorescence staining protocol cellsor ounted on coverslips
1. Wash ×1 in TBS for 5 min at RT.
2. Wash ×1 in EtOH 50% for 5 min at RT.
3. Wash ×1 EtOH 70% for 5 min at RT.
4. Incubate with the compound (LG13) at RT. A drop of freshly prepared compound (LG13) is placed on a clean slide with the use of a syringe that carrying a 2 mm filter (see also FIG. 1 from Evangelou & Gorgoulis, 2016). Then the cover-slip with the cells is turned down (using thin edged forceps) on the slide and attached on the dye drop in a way that the material faces down the drop on the slide (All incubations were performed in chambers (cover slips) and coplin jars (glass slides) to avoid exsiccation of the material), (see also FIG. 1 from Evangelou & Gorgoulis, 2016).
5. The staining reaction is monitored under the light microscope until detection of the signal (average time 5-8 min).
6. Wash ×2 in EtOH 50%.
7. Repeat washing ×2 in fresh EtOH 50%.
8. Wash ×2 in TBS for 30 sec and ×1 for 5 min at RT.
9. Incubate with 0.5% Triton X/TBS for 3 min at RT.
10. Wash ×1 in TBS for 5 min at RT.
11. Incubate with the primary anti-biotin antibody diluted 1:400 in TBS ([Hyb-8] ab201341, Abcam) for 60 min at 37° C.
12. Wash ×3 in TBS for 5 min at RT.
13. Incubate with goat anti-mouse secondary antibody, 568 Alexa Fluor conjugated, diluted 1:200 in TBS [Thermo Fisher Scientific (Cat no: A-11004)] for 60 min in RT.
14. Wash ×5 in TBS for 5 min at RT.
15. Incubate with DAPI diluted 1:1000 in TBS for 5 min at RT.
16. Wash ×2 in TBS for 5 min at RT.
17. Apply permanent mounting medium Glycergel (Dako-Cytomation).
18. Observe under the fluorescence microscope
(N.B. The Fluorescent Microscope can be used in control experiments. Lipofuscin that accumulates in senescent cells is well known to exhibit autofluorescent properties that are quenched not only with SBB (Georgakopoulou et al., 2013), but also by the current compound (LG13) staining. We used a Leica DMRAZ microscope equipped with a Leica DFC350FX camera. The sample was mounted in 40% glycerol/TBS medium, after its appropriate preparation and observed by excitation at 450-490 nm, using a dichromatic mirror at 510 nm and a long pass filter at 515 nm (Georgakopoulou et al., 2013).

Figure 9:
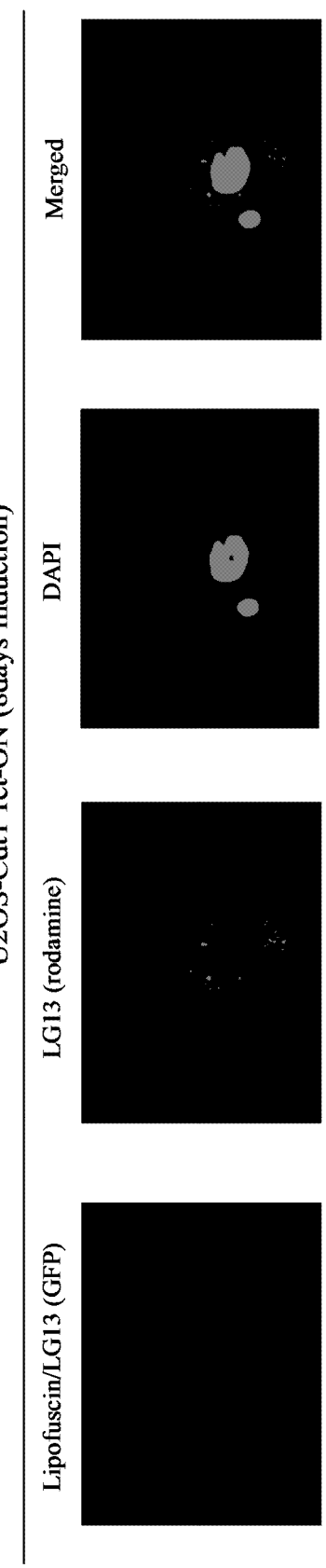
FIG. 9. Indirect immunofluorescence for the detection of senescent cells using the LG13 compound. The anti-biotin antibody was rodamine conjugated. Note that LG13 staining "masks" the autofluorescence ability of lipofuscin, similarly to SBB (Georgakopoulou et al., 2013), providing a control assay [panel: Lipofuscin/LG13 (GFP)].

Representative results from the application of this method are shown in FIG. 9.

Inventive Example 7

In inventive example 7 the derivative LG13 was used to detect lipofuscin rich cells in cell aspirations or cell cultures by flow cytometry analysis.
Flow Cytometry Analysis for Detection of Senescent Cells in Cell Culture
1. Cells harvested from culture are fixed in EtOH 70% at 4° C.
2. Centrifuge at 1200 rpm for 5 min at RT.
3. Wash ×1 in 5 ml PBS at RT.
4. Centrifuge at 1200 rpm for 5 min at RT.
5. Incubate in 0.1% Triton X/PBS for 15 min at RT.
6. Centrifuge at 1200 rpm for 5 min at RT.
7. Wash ×1 EtOH 50% for 5 min at RT
8. Centrifuge at 1200 rpm for 5 min at RT.
9. Wash ×1 EtOH 70% for 5 min at RT.
10. Centrifuge at 1200 rpm for 5 min at RT.
11. Cover cell pellet with compound LG13 and incubate for 8 min at RT.
12. Centrifuge at 1200 rpm for 5 min at RT.
13. Wash with EtOH 50% and centrifuge at 1200 rpm for 5 min at RT, repeat ×3.
14. Wash ×1 in PBS.
15. Centrifuge at 1200 rpm for 5 min at RT.
16. Incubate with the primary anti-biotin antibody diluted 1:400 in PBS ([Hyb-8] ab201341, Abcam) for 60 min at 37° C.
17. Wash ×1 with PBS.
18. Centrifuge at 1200 rpm for 5 min at RT.
19. Incubate with secondary antibody, goat anti-mouse 568 Alexa Fluor conjugated, diluted 1:100 in PBS [Thermo Fisher Scientific (Cat no: A-11004)] for 20-30 min in dark and on ice.
20. Wash ×1 with PBS.
21. Centrifuge at 1200 rpm for 5 min at RT.

Figure 10:
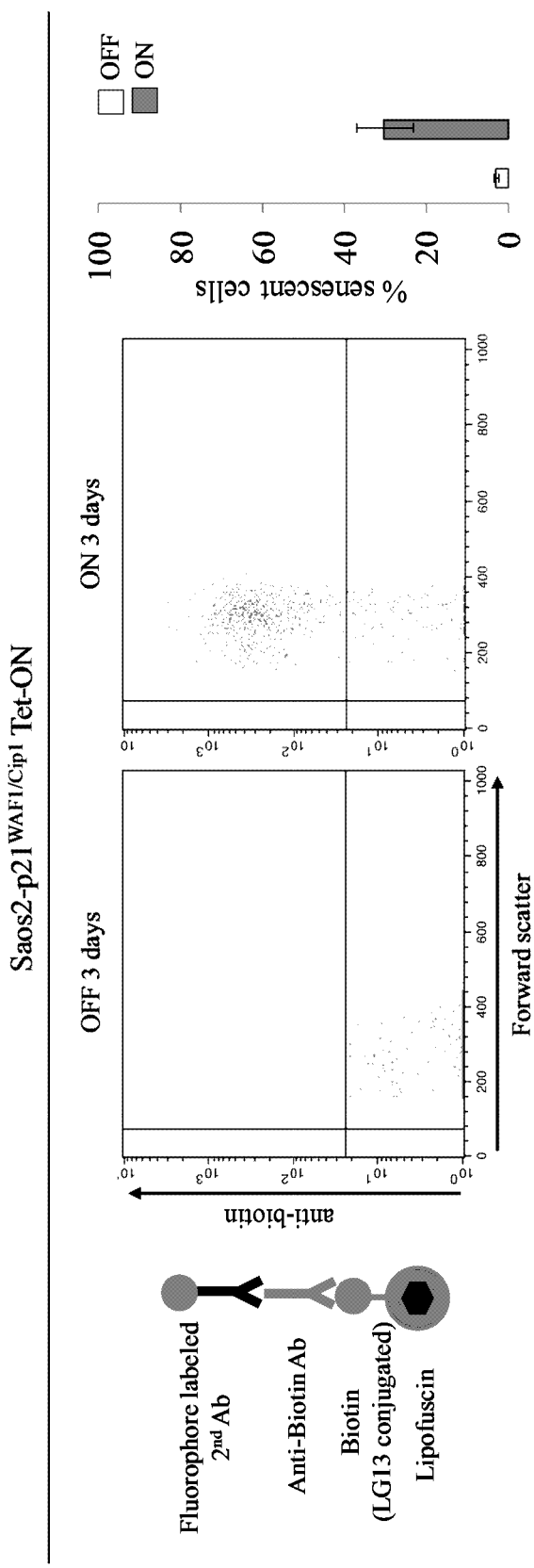
FIG. 10. The LG13 compound detects robustly senescent cells by a simple adaption of the histo-/immuno-chemical assay (HIC) (see FIG. 1$b,c$) for use with flow cytometry analysis in a very straightforward manner that is comparable to a previously published protocol (Debacq-Chainiaux et al., 2009).

Representative results from the application of this method are shown in FIG. 10.

Inventive Example 8

In inventive example 8 the derivative LG13 was used to detect lipofuscin rich cells in tissue sections by double immunohistochemistry staining, following general staining protocols detailed hereinabove.

Figure 11:
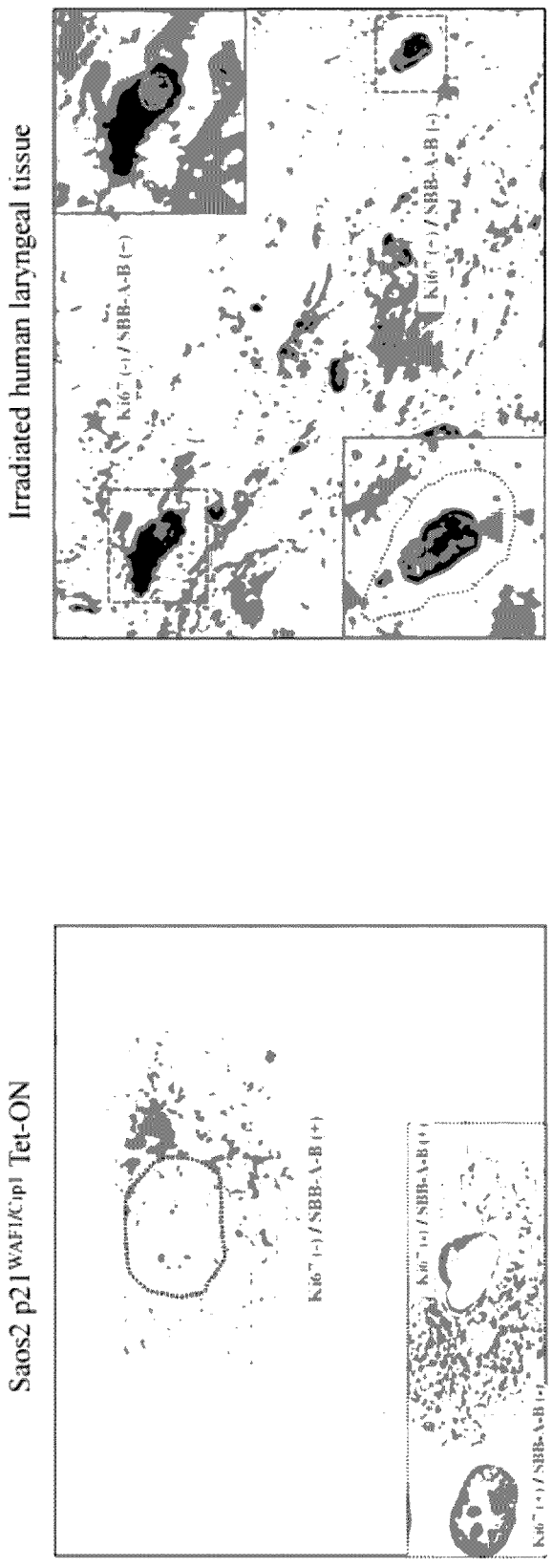
FIG. 11. Strict inverse relationship between Ki67 expression (yellow arrowheads) and LG13 presence (white arrowheads) as assessed by employing double staining in cell culture systems and human clinical samples (red dashed line: cell perimeter; black or white dashed line: nuclear perimeter). The proposed method of detecting senescent cells using the new compounds of this invention has the advantage of allowing concurrent detection of proteins or RNA molecules directly within the observed senescent cells. Magnifications: cells ×630, tissues ×400 and insets ×630 [SBB-A-B: SBB-Analogue-Biotin represents LG13].
Figure 12:
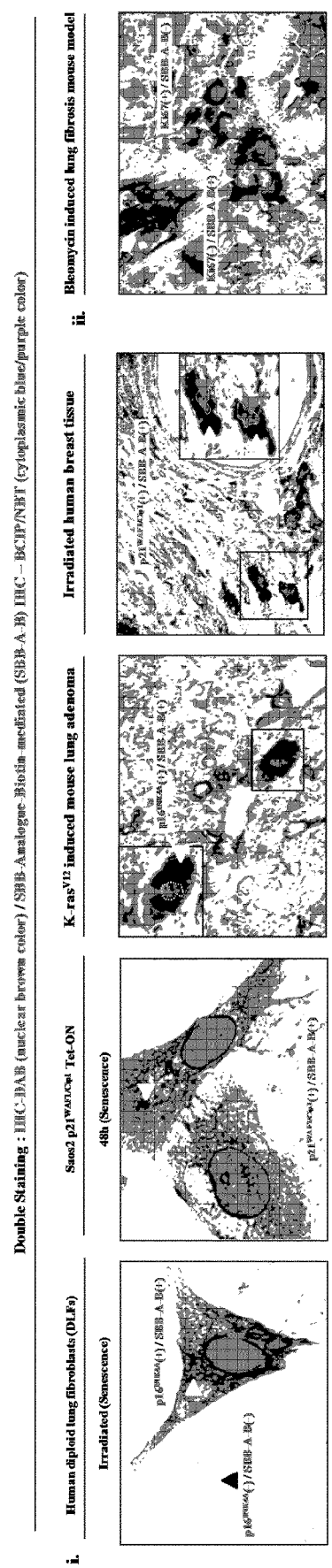
FIG. 12. Further representative images from double-staining experiments in cellular systems (irradiated DLFs and induced Saos2-p21$^{WAF1/Cip1}$ Tet-ON cells), mouse models (K-rasV12-induced lung adenoma), and human clinical samples (irradiated breast samples) (i), showing nuclear p16$^{INK4A}$ or p21$^{WAF1/Cip1}$ expression (DAB IHC-brown color: yellow arrowheads) in senescent cells that are concurrently positive with the LG13 compound, visualized with the BCIP/NBT chromogenic hybrid Histo-IHC reaction (dark blue perinuclear and cytoplasmic color: white arrowheads; red dashed line: cell perimeter; white dashed line: nuclear perimeter; black arrowhead: [p16$^{INK4A}$(−)/SBB-A-B(−)]). (ii) Representative image of double staining in lung sections from a mouse model (bleomycin-induced lung fibrosis), depicting a strict inverse relationship between nuclear Ki67 positivity and LG13 staining [Ki67(+)/SBB-A-B(−): yellow arrowheads; Ki67(−)/SBB-A-B(+): white arrowheads]. Magnifications: cells ×630, tissues ×400 and insets ×630. Counterstain (when applied): hematoxylin for IHC and nuclear fast red for HC (SBB) [SBB-A-B: SBB-Analogue-Biotin represents LG13].

Representative results from the application of this method are shown in FIGS. 11 and 12.

Representative images from double-staining experiments in cellular systems (irradiated Diploid Lung Fibroblasts and induced Saos2-p21$^{WAF1/Cip1}$ Tet-ON), mouse models (K-ras$^{V12}$-induced lung adenoma), and human clinical samples (irradiated breast samples) (FIG. 12$i$), showing nuclear p16$^{INK4A}$ or p21$^{WAF1/Cip1}$ expression (DAB IHC-brown color: yellow arrowheads) in senescent cells that are concurrently positive with the LG13 compound, visualized with the BCIP/NBT chromogenic hybrid Histo-IHC reaction (dark blue perinuclear and cytoplasmic color: white arrowheads; red dashed line: cell perimeter; white dashed line: nuclear perimeter; black arrowhead: [p16$^{INK4A}$(−)/SBB-A-B(−)]). (FIG. 12$ii$) Representative image of double staining in lung sections from a mouse model (bleomycin-induced lung fibrosis) (FIG. 12ii), depicting a strict inverse relationship between nuclear Ki67 positivity and GL13 staining [Ki67(+)/SBB-A-B(−): yellow arrowheads; Ki67(−)/SBB-A-B(+): white arrowheads]. Magnifications: cells ×630, tissues (b,c) ×400 and insets ×630. Counterstain (when applied): hematoxylin for HIC and nuclear fast red for HC (SBB) [where SBB-A-B: SBB-Analogue-Biotin is LG13].

Inventive Example 9

In inventive example 9 the derivatives LG39, LG52, LG56 (Examples 5, 7 and 6 respectively) were used to detect lipofuscin rich cells in tissue sections by immunohistochemistry staining, following general staining protocols detailed hereinabove.

Figure 13:
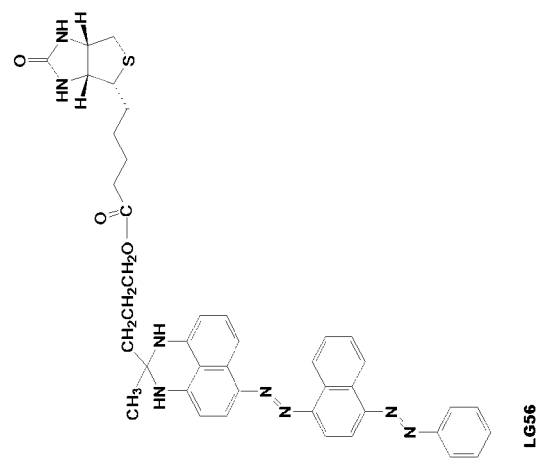
FIG. 13. The compounds LG39, LG52, LG56 (Examples 5, 7 and 6 respectively) detect robustly lipofuscin rich senescent cells in the induced Saos2-p21$^{WAF1/Cip1}$ Tet-ON cellular system (Galanos et al, 2016) by using immunohistochemistry staining.
Figure 13:
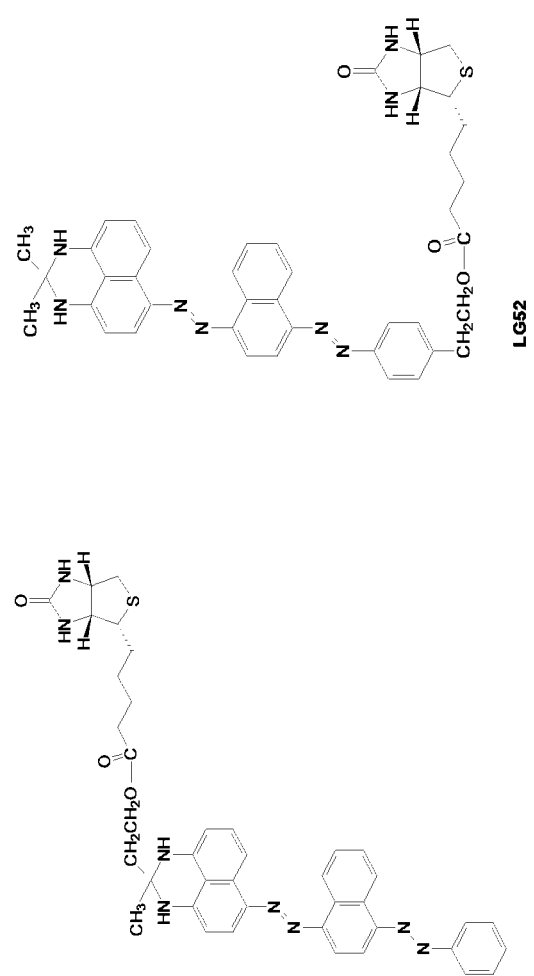

Representative results from the application of this method in the induced Saos2-p21$^{WAF1/Cip1}$ Tet-ON cellular system are shown in FIG. 13.

Further Inventive Examples

Further Staining Experiments

Figure 14:
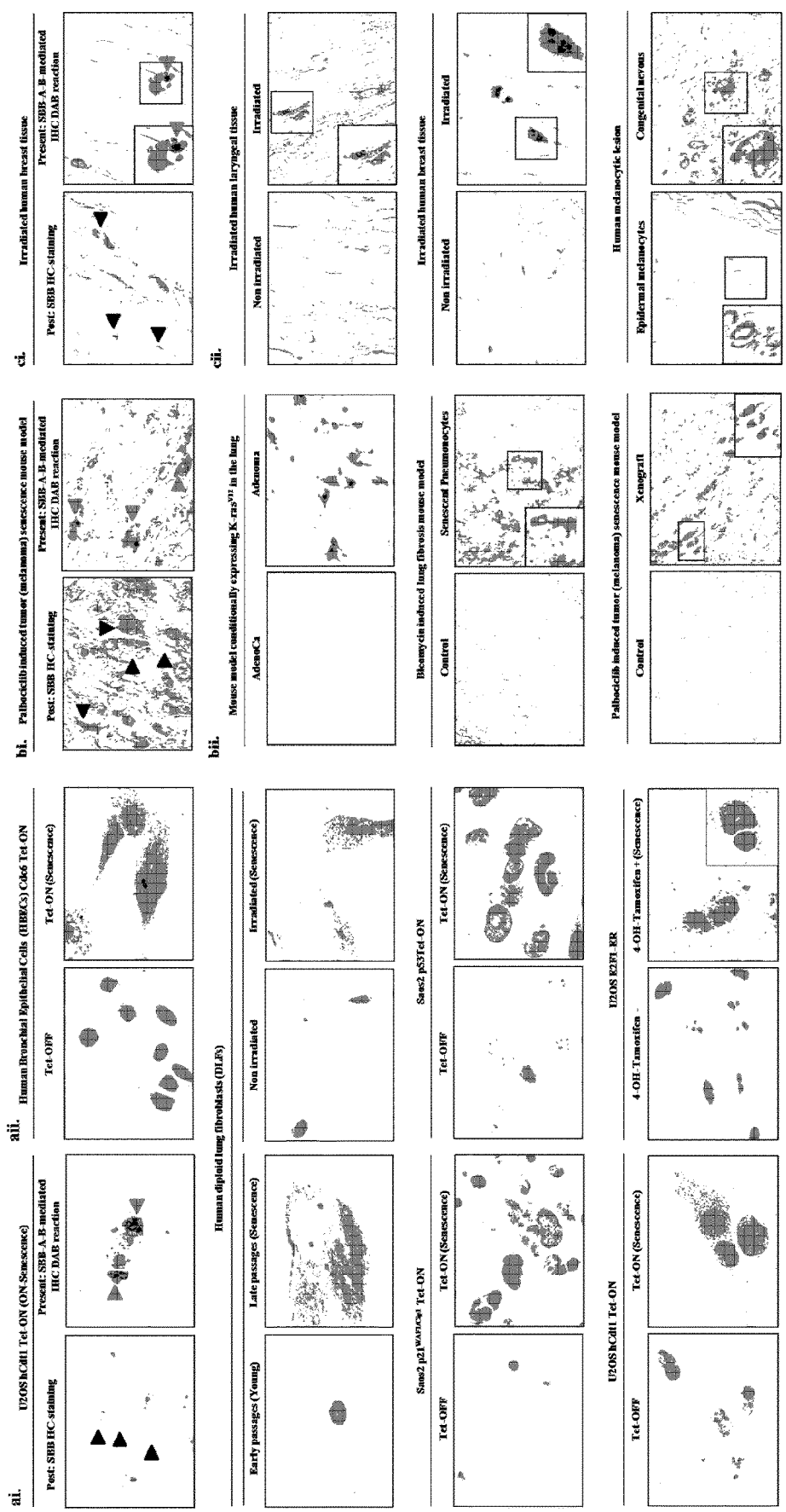
FIG. 14. Further applications showing detection of senescent cells in vitro and in vivo using a new chemical compound, linked with biotin, and employing an enhancing immunohistochemical-enzymatic detection assay. Representative results from comparative analysis after applying the SBB histochemical stain (HC) and the hybrid, LG13-mediated, histo-/immunochemical assay (IHC), also denoted as SBB-Analogue-Biotin (SBB-A-B)-mediated IHC reaction are shown in panels (ai), (bi), and (ci), (green arrowheads depict LG13 (DAB) staining, while black arrowheads show SBB-positive granules in the cytoplasm). Specifically, the superiority of the LG13 IHC staining relative to SBB HC staining is depicted in the U2OS hCdt1 Tet-ON cell line (a representative cellular system) (ai) after oncogene (hCdt1)-induced senescence (OIS), in palbociclib-induced tumor (human melanoma xenograft) senescence mouse model (a representative animal model) (bi), and in irradiated human breast tissue (a representative human clinical sample) (ci). Further examples of sensitive senescence detection with the LG13 compound, using the HIC assay, in additional cellular systems (aii), mouse models (bii), and human clinical samples (cii) are also shown. Negative controls (devoid of senescent cells) are depicted in each setting. Magnifications: cells ×630, tissues ×400 and insets ×630.

Detection of senescent cells in vitro and in vivo using a new chemical compound, linked with biotin, and employing an enhancing immunohistochemical-enzymatic detection assay. Referring to FIG. 14, representative results from comparative analysis after applying the SBB histochemical stain (HC) and the hybrid, GL13-mediated, histo-/immunochemical assay (HIC), also denoted as SBB-Analogue-Biotin (SBB-A-B)-mediated IHC reaction are shown, see panels (ai), (bi), and (ci), (green arrowheads depict GL13 (DAB) staining, while black arrowheads show SBB-positive granules in the cytoplasm). Specifically, the superiority of the GL13 IHC staining relative to SBB HC staining is depicted in the U2OS hCdt1 Tet-ON cell line (a representative cellular system) (ai) after oncogene (hCdt1)-induced senescence (OIS), in palbociclib-induced tumor (human melanoma xenograft) senescence mouse model (a representative animal model) (bi), and in irradiated human breast tissue (a representative human clinical sample) (ci). Further examples of sensitive senescence detection with the GL13 compound, using the HIC assay, in additional cellular systems (aii), mouse models (bii), and human clinical samples (cii) are also shown. Negative controls (devoid of senescent cells) are depicted in each setting.

Quantitative Analysis

Figure 15:
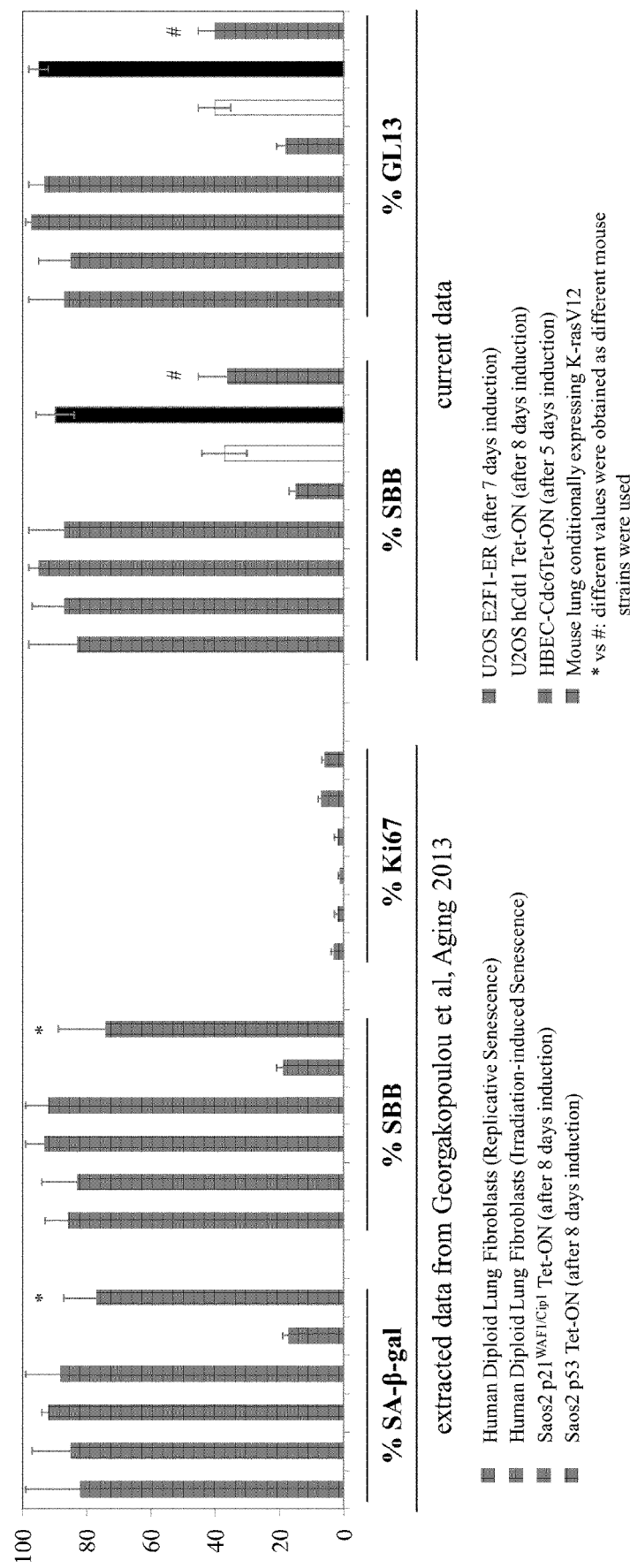
FIG. 15. Quantitative analysis and concordance of specificity between the SA-b-gal, SBB, and LG13 staining, along with inverse relationship with Ki67 positivity in retrospectively (Georgakopoulou et al., 2013) and currently examined biological systems (presented in FIG. 14) with established senescence.

Quantitative analysis and concordance of specificity between the SA-b-gal, SBB, and GL13 staining, along with inverse relationship with Ki67 positivity in retrospectively (Georgakopoulou et al., 2013) and currently examined biological systems with established senescence is shown in FIG. 15.

Inverse Relationship Between GL13 IHC Staining and Proliferation Markers (Ki67 and BrdU Incorporation)

Figure 16:
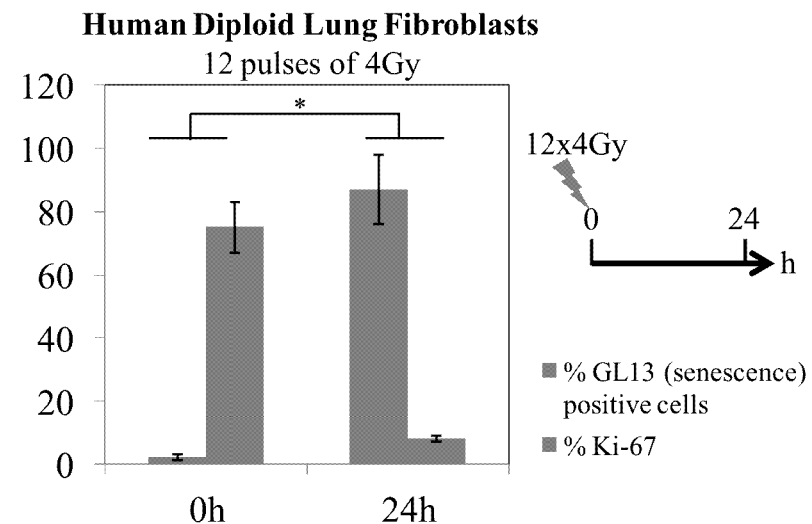
FIG. 16. Inverse relationship between LG13 IHC staining and proliferation markers (Ki67 and BrdU incorporation) is depicted in (a) human diploid lung fibroblasts (DLFs) and (b) human bronchial epithelial cells (HBEC-Cdc6 Tet-ON).
Figure 16:
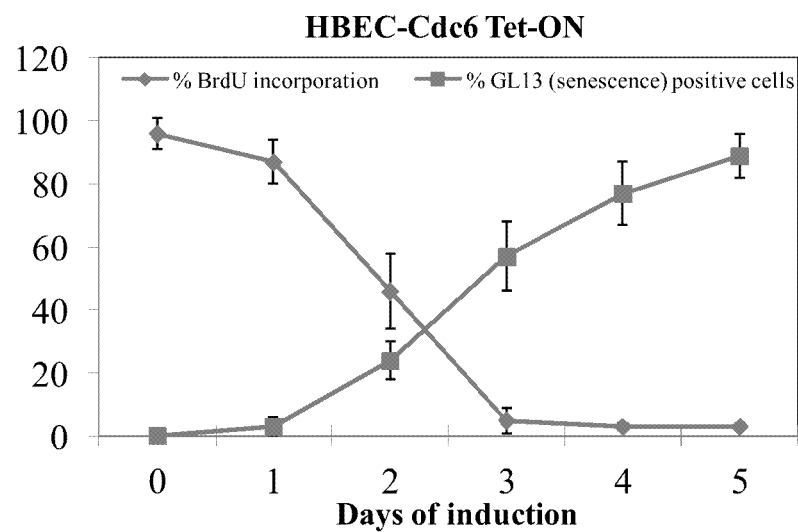

Inverse relationship between GL13 IHC staining and proliferation markers (Ki67 and BrdU incorporation) is depicted in human diploid lung fibroblasts (DLFs) and human bronchial epithelial cells (HBEC-Cdc6 Tet-ON) as is shown in FIG. 16.

False-Positive Studies

Figure 17:
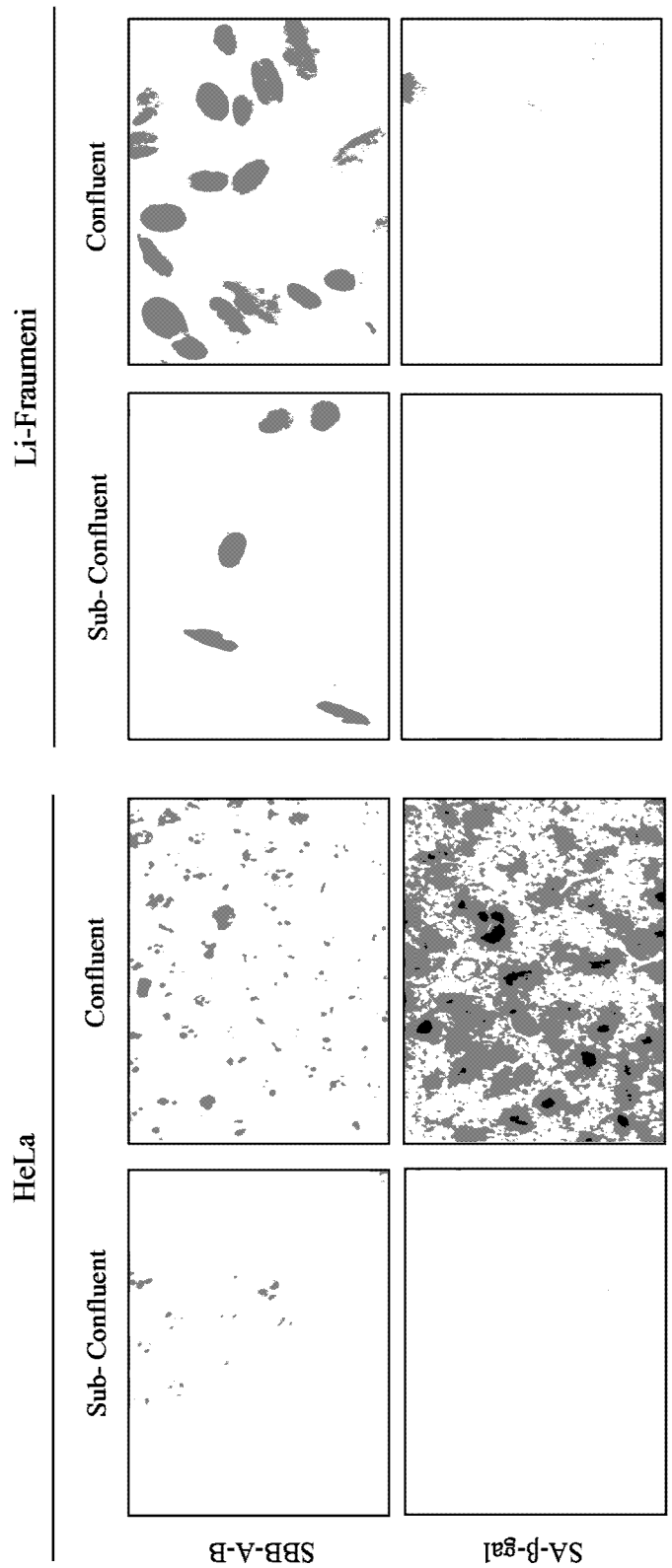
FIG. 17. Negative LG13 staining under cell confluency, in cancer cells (HeLa) and near normal (Li-Fraumeni) fibroblasts (Galanos et al., 2016), demonstrating that this new method is devoid of the false positive side-effects of SA-β-Gal.
Figure 18:
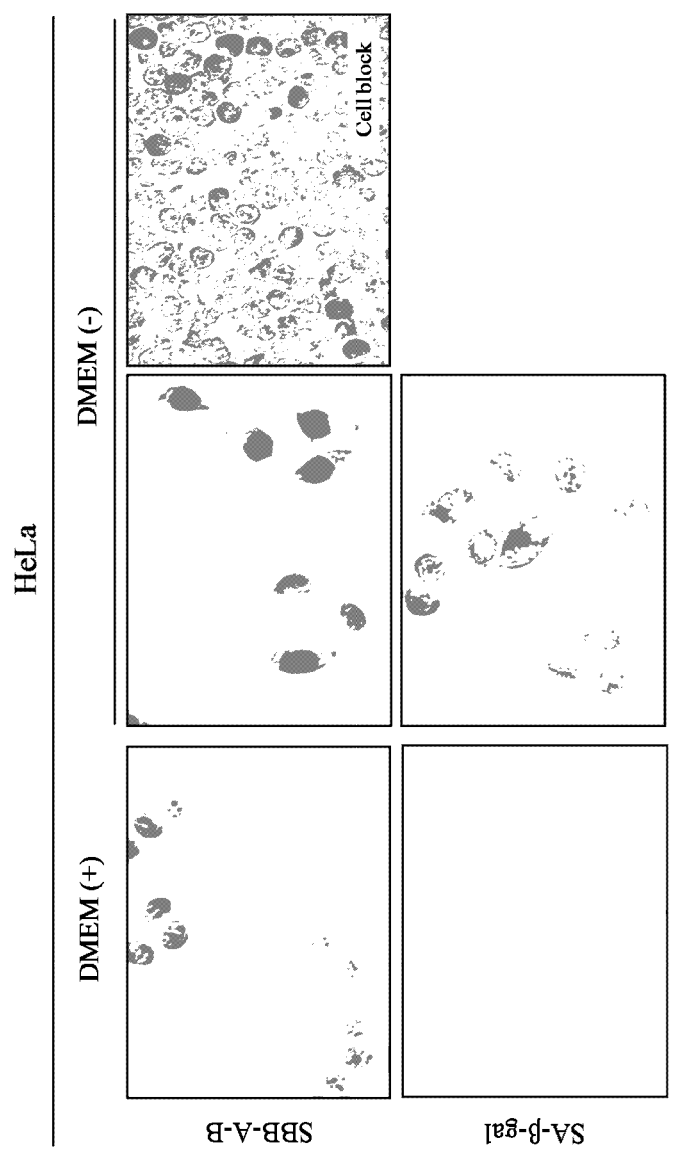
FIG. 18. Negative LG13 staining after serum starvation conditions in comparison to SA-β-gal that gave positive signal. Note: serum starved HeLa cells were also negative for LG13 staining after formalin fixing and paraffin embedding (panel: cell block).

Compound GL13, as SBB staining, was shown to be deprived of the false-positive staining disadvantages of SA-b-gal due to serum starvation and cell confluency (see FIGS. 17 and 18; Georgakopoulou et al., 2013).

REFERENCES

Gorgoulis V G, Halazonetis T D. Curr Opin Cell Biol 2010, 22: 816-827.
Dimri G P, et al. Proc Natl Acad Sci USA 1995. 92: 9363-9367.
Chen Q M. Ann N Y Acad Sci 2000, 908: 111-125.
Rodier F, Campisi J. J. Cell Biol 2011, 192: 547-556.
Bartkova J, et al. Nature. 2006, 444: 633-637.
Halazonetis T D, et al. Science 2008, 319: 1352-1355.
Dirmi G P, Campisi J, Peacocke M. U.S. Pat. No. 5,491,069 A, U.S. Ser. No. 08/198,436, 1996.
Dirmi G P, Campisi J, Peacocke M. U.S. Pat. No. 5,795,728 A, U.S. Ser. No. 08/479,082, 1996.
Liontos M, et al. Cancer Res 2007, 67: 10899-909.
Liontos M, et al. Am J Pathol 2009, 175: 376-391.
Shay J W, Roninson I B. Oncogene 2004, 23: 2919-2933.
Collado M, Serrano M. Nat Rev Cancer 2006, 6: 472-476.
de Jesus B B, Blasco M A. Circ Res 2012, 111: 97-109.
Cairney C J, et al. Drug Discov Today 2012, 17: 269-276.
Collado M, Serrano M. Nat Rev Cancer 2010, 10:51-57.
Debacq-Chainiaux F, et al. Nat Protoc 2009, 4: 1798-1806.
Severino J, et al. Exp Cell Res 2000, 257:162-171.
Binet R, et al. Cancer Res 2009, 69: 9183-9191.
Georgakopoulou E, et al. Aging (Albany N.Y.) 2013, 5: 37.
Jung T, et al. Methods Mol Biol 2010, 594: 173-193.
Jung T, et al. Ann N Y Acad Sci 2007, 1119: 97-111.
Brunk U T, Terman A. Free Radic Biol Med 2002, 33: 611-619.
Hohn A, et al. Free Radic Biol Med 2010, 48: 1100-1108.
Dowson J H, Harris S J. J Microsc 1981, 123: 249-258.
Jung T A H, Grune T. 2010. Advanced Protocols in Oxidative Stress II, Methods in Molecular Biology. D. Armstrong, editor: Humana Press
Charles C. 2002. Theory and Practice of Histological Techniques. G M Bancroft D editor: Churchill Livingstone.
Glees P, Hasan M. Norm Pathol Anat (Stuttg) 1976, 32: 1-68.
Robles L J. Mech Ageing Dev 1978, 7: 53-64.
Diamandis E P, Christopoulos T K. Clin Chem 1991, 37: 625-636
Bolzati C, et al. Nucl Med Biol 2006, 34: 511-522.
Zhang J, Zhang S. Synth Comm 2007, 37: 2615-2624.
Farrand L D et al Merck Patent GmbH WO 2014/111112 A1.
da Costa S T P, et al. ACS Med Chem Lett 2012, 3: 509-514.
Abell A D, et al. Patent WO 2013/040647 A1.
Aoshiba K, et al. Exp Toxicol Pathol. 2013, 65:1053-62.
Aoshiba K, et al. Eur Respir J. 2003, 22: 436-43
Castro P, et alProstate 2003, 55: 30-38.
Collado M, et al. Nature 2005, 436: 642.
Evangelou K, et al. Cell Death Differ. 2013, 20: 1485-97.
Evangelou K, Gorgoulis V G. Methods in Molecular Biology, 2016, vol. 1534, Springer.
Gewirtz D A. J Cell Physiol. 2014, 229: 6-9.
Hellevik T, Martinez-Zubiaurre I. Front Oncol. 2014, 4: 1.
Michaloglou C, et al. Nature 2005, 436: 720-724.
Yoshida A, et al. Cancer Res. 2016, 76: 2990-3002.
Galanos P, et al. Nat Cell Biol. 2016, 18: 777-89.
Liakou E, et al. Aging (Albany N.Y.) 2016, 8: 1650-69.
Petrakis T G, et al. Semin Cancer Biol. 2016, 37-38: 3-15.

The invention claimed is:

1. A compound of general formula (1) or a salt or solvate thereof:

(1)

wherein:
SBB analogues refer to the general structure (2) or (3) shown below:

(2)

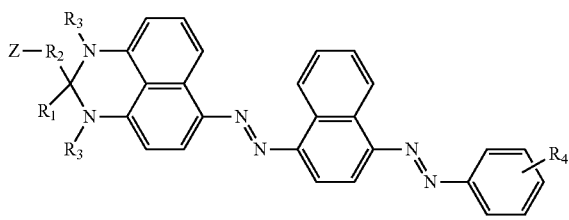

(3)

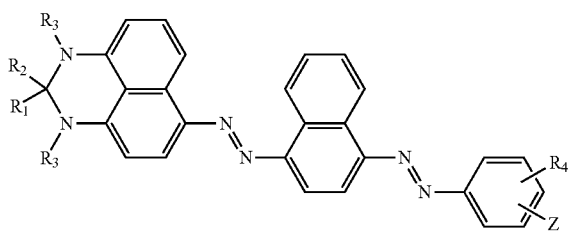

wherein:
$R_1$ and $R_2$ are each independently selected from the group consisting of:
  i) hydrogen; with the proviso that $R_2$ is not hydrogen in general structure (2) and only one of $R_1$ and $R_2$ can be hydrogen in general structure (3);
  ii) an optionally substituted (1-10C)alkyl group;
  iii) an optionally substituted aryl group;
  iv) an optionally substituted (1-10C)alkyl-aryl group;
  v) an optionally substituted aryl-(1-10C)alkyl group; and
  vi) $R_1$ and $R_2$ are linked so as to form part of a spiranic cycloalkane group, selected from selected from the group consisting of cyclopentyl, cyclohexyl, cycloheptyl, cyclooctyl, cyclononyl and adamantanyl;
$R_3$ is hydrogen or (1-10C)alkyl group;
$R_4$ is hydrogen, or one or more of the following substituents:
  i) a halogen selected from F, Cl, Br and I;
  ii) $NO_2$;
  iii) $CF_3$;
  iv) $SCH_3$;
  v) an optionally substituted (1-5C)alkyl group; or
  vi) a (1-10C)alkoxy group which optionally comprises one or more heteroatoms;
Z is either $Z_1$ or Ar—$Z_1$, and $Z_1$ is selected from the group consisting of —O—, —NH—, —O($CH_2$)$_n$$CH_2$O—, —($CH_2$)$_q$O— and —COO—, wherein n is an integer selected from 1 to 9, wherein q is an integer selected from 1 to 4, and wherein Ar is an aryl group optionally substituted with one or more of the following substituents halogen, (1-6C)alkyl, (1-6C)alkenyl or (1-5C)alkoxy;

L is a bond or linker group that links Z to hapten; and
hapten is biotin, digoxigenin, 2,4-dinitrophenol, or fluorescein.

2. A compound according to claim 1, wherein Z is linked to hapten by an ester bond, an amide bond or an ether bond.

3. A compound according to claim 1, wherein the SBB analogues refer to the general structure (2), shown below:

(2)

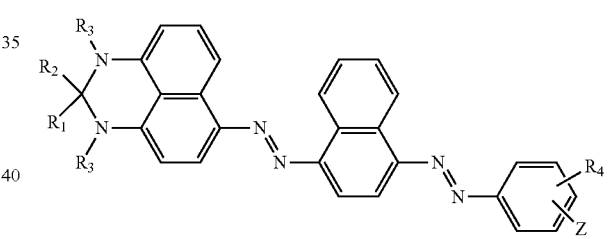

wherein Z and $R_1$ to $R_4$ are as defined in claim 1.

4. A compound according to claim 1, wherein the SBB analogues refer to the general structure (3), shown below:

(3)

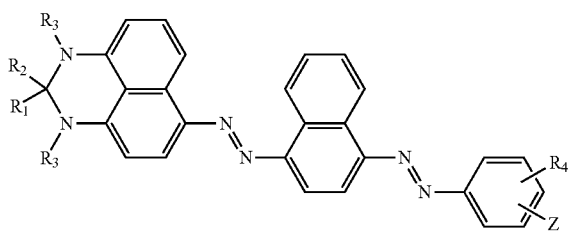

wherein Z and $R_1$ to $R_4$ are as defined in claim 1.

5. A compound according to claim 1, wherein Z is linked to hapten by an ester bond.

6. A compound according to claim 5, wherein the hapten is biotin (i.e. a compound of the formula (4), shown below:

(4)

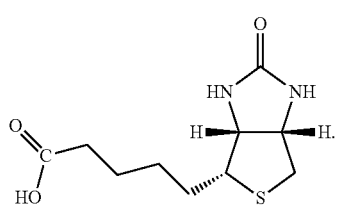

7. A compound according to claim 6, wherein said compound has the general formula (5), shown below:

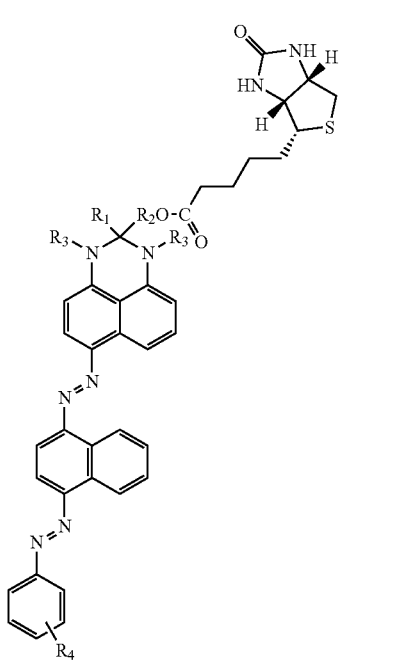

(5)

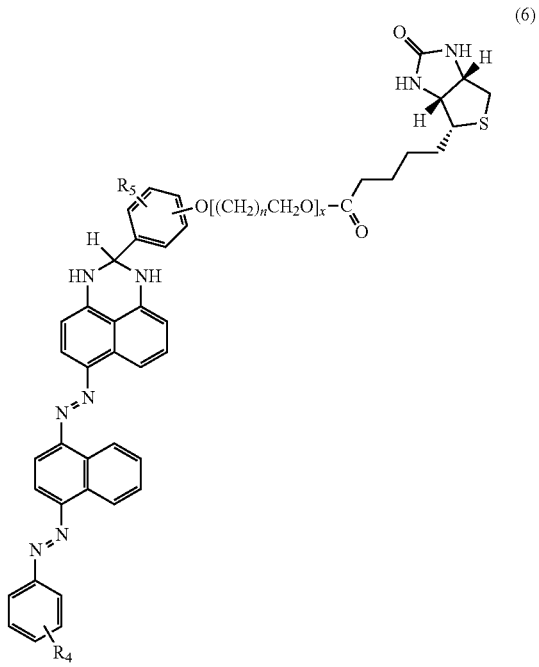

(6)

wherein;

$R_1$ is a (1-10C)alkyl group;

$R_2$ is a (1-8C)alkyl group, an optionally substituted aryl group or an optionally substituted (1-5C)alkyl-aryl group:

$R_3$ is hydrogen or (1-10C)alkyl group;

$R_4$ is hydrogen, or one or more of the following substituents:

i) halogen selected from F, Cl, Br and I, ii) $NO_2$, iii) $CF_3$, iv) $SCH_3$, v) an optionally substituted (1-5C)alkyl group; or vi) a (1-10C)alkoxy group which optionally comprises one or more heteroatoms.

8. A compound according to claim 6, wherein said compound has the general formula (6), shown below:

wherein:

x is an integer selected from 0 or 1;

n is an integer selected from 1 to 9;

$R_4$ is hydrogen, or one or more of the following substituents:

i) halogen selected from F, Cl, Br and I, ii) $NO_2$, iii) $CF_3$, iv) $SCH_3$, v) an optionally substituted (1-5C)alkyl group; or vi) a (1-10C)alkoxy group which optionally comprises one or more heteroatoms;

$R_5$ is hydrogen, or one or more of the following substituents:

i) halogen selected from F, Cl, Br and I;

ii) (1-6C)alkyl group or (1-6C)alkenyl group; or iii) (1-5C)alkoxy group.

9. A compound according to claim 6, wherein said compound has the general formula (7), shown below:

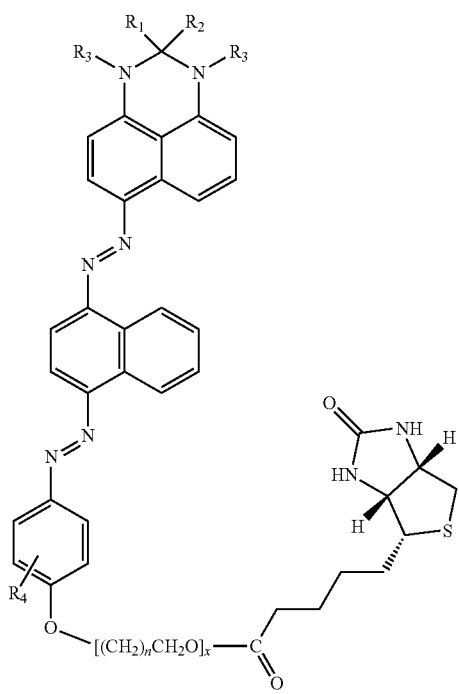

(7)

wherein, x is an integer selected from 0 or 1;

n is an integer selected from 1 to 9;

$R_1$ and $R_2$ are each independently selected from:

i) hydrogen, provided that at least one of $R_1$, $R_2$ is other than hydrogen;

ii) an optionally substituted (1-10C)alkyl group;

iii) an optionally substituted aryl group;

iv) part of a spiranic cycloalkane group, selected from the group consisting of cyclopentyl, cyclohexyl, cycloheptyl, cyclooctyl, cyclononyl and adamantanyl;

v) an optionally substituted (1-10C)alkyl-aryl group; or vi) an optionally substituted aryl-(1-10C)alkyl group;

$R_3$ is hydrogen or a (1-10C)alkyl group;

$R_4$ is hydrogen, or one or more of the following substituents:

i) halogen selected from F, Cl, Br and I, ii) $NO_2$, iii) $CF_3$, iv) $SCH_3$, v) an optionally substituted (1-5C)alkyl group; or vi) a (1-10C)alkoxy group which optionally comprises one or more heteroatoms.

10. A compound according to claim 6, wherein said compound has the general formula (8), shown below:

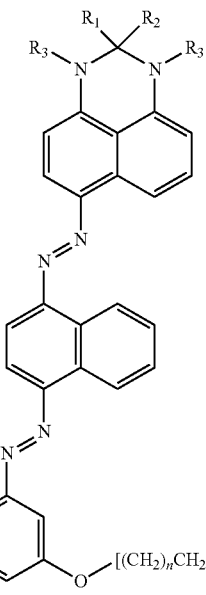
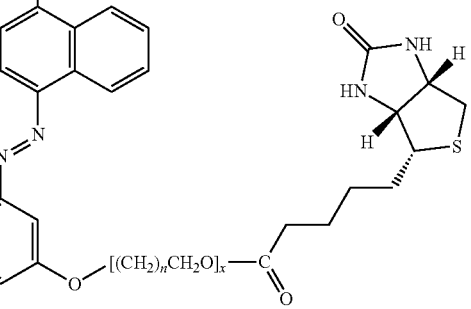

(8)

wherein, x is an integer selected from 0 or 1;

n is an integer selected from 1 to 9;

$R_1$ and $R_2$ are each independently selected from the group consisting of:

i) hydrogen, provided that at least one of $R_1$, $R_2$ is other than hydrogen;

ii) an optionally substituted (1-10C)alkyl group;

iii) an optionally substituted aryl group;

iv) part of a spiranic cycloalkane group, selected from the group consisting of cyclopentyl, cyclohexyl, cycloheptyl, cyclooctyl, cyclononyl or adamantanyl;

v) an optionally substituted (1-10C)alkyl-aryl group; and vi) an optionally substituted aryl-(1-10C)alkyl group;

$R_3$ is hydrogen or a (1-10C)alkyl group;

$R_4$ is hydrogen, or one or more of the following substituents:

i) halogen selected from F, Cl, Br and I, ii) $NO_2$, iii) $CF_3$, iv) $SCH_3$, v) an optionally substituted (1-5C)alkyl group; or vi) a (1-10C)alkoxy group which optionally comprises one or more heteroatoms.

11. A compound according to claim 6, wherein said compound has the general formula (9), shown below:

(9)

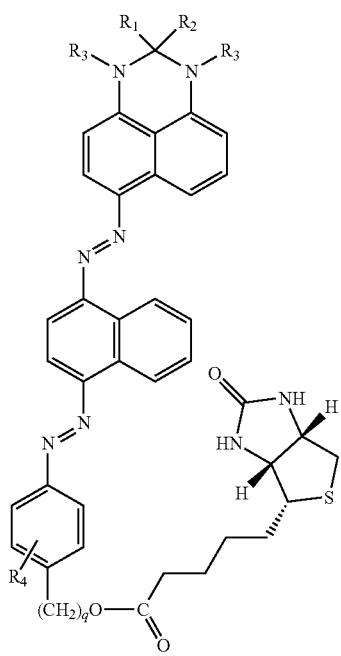

wherein q is an integer selected from 1 to 4;

$R_1$ and $R_2$ are each independently selected from the group consisting of:

i) hydrogen; provided that at least one of $R_1$, $R_2$ is other than hydrogen;

ii) an optionally substituted (1-10C)alkyl group;

iii) an optionally substituted aryl group;

iv) part of a spiranic cycloalkane group, selected from the group consisting of cyclopentyl, cyclohexyl, cycloheptyl, cyclooctyl, cyclononyl and adamantanyl;

v) an optionally substituted (1-10C)alkyl-aryl group; and vi) an optionally substituted acyl-(1-10C)alkyl group;

$R_3$ is hydrogen or a (1-10C)alkyl group;

$R_4$ is hydrogen, or one or more of the following substituents:

i) halogen selected from F, Cl, Br and I, ii) $NO_2$, iii) $CF_3$, iv) $SCH_3$, v) an optionally substituted (1-5C)alkyl group; or vi) a (1-10C)alkoxy group which optionally comprises one or more heteroatoms.

12. A compound according to claim 6, wherein said compound has the general formula (10), shown below:

(10)

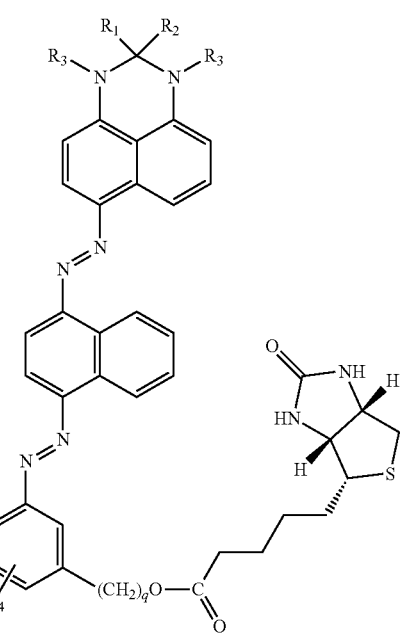

wherein, q is an integer selected from 1 to 4;

$R_1$ and $R_2$ are each independently selected from the group consisting of:

i) hydrogen, provided that at least one of $R_1$, $R_2$ is other than hydrogen;

ii) an optionally substituted (1-10C)alkyl group;

iii) an optionally substituted aryl group;

iv) part of a spiranic cycloalkane group, selected from the group consisting of cyclopentyl, cyclohexyl, cycloheptyl, cyclooctyl, cyclononyl and adamantanyl;

v) an optionally substituted (1-10C)alkyl-aryl group; and vi) an optionally substituted aryl-(1-10C)alkyl group;

$R_3$ is hydrogen or a (1-10C)alkyl group;

$R_4$ is hydrogen, or one or more of the following substituents:

i) halogen selected from F, Cl, Br and I, ii) $NO_2$, iii) $CF_3$, iv) $SCH_3$, v) an optionally substituted (1-5C)alkyl group: or vi) a (1-10C)alkoxy group which optionally comprises one or more heteroatoms.

13. A compound according to claim 6, selected from any one of the following:

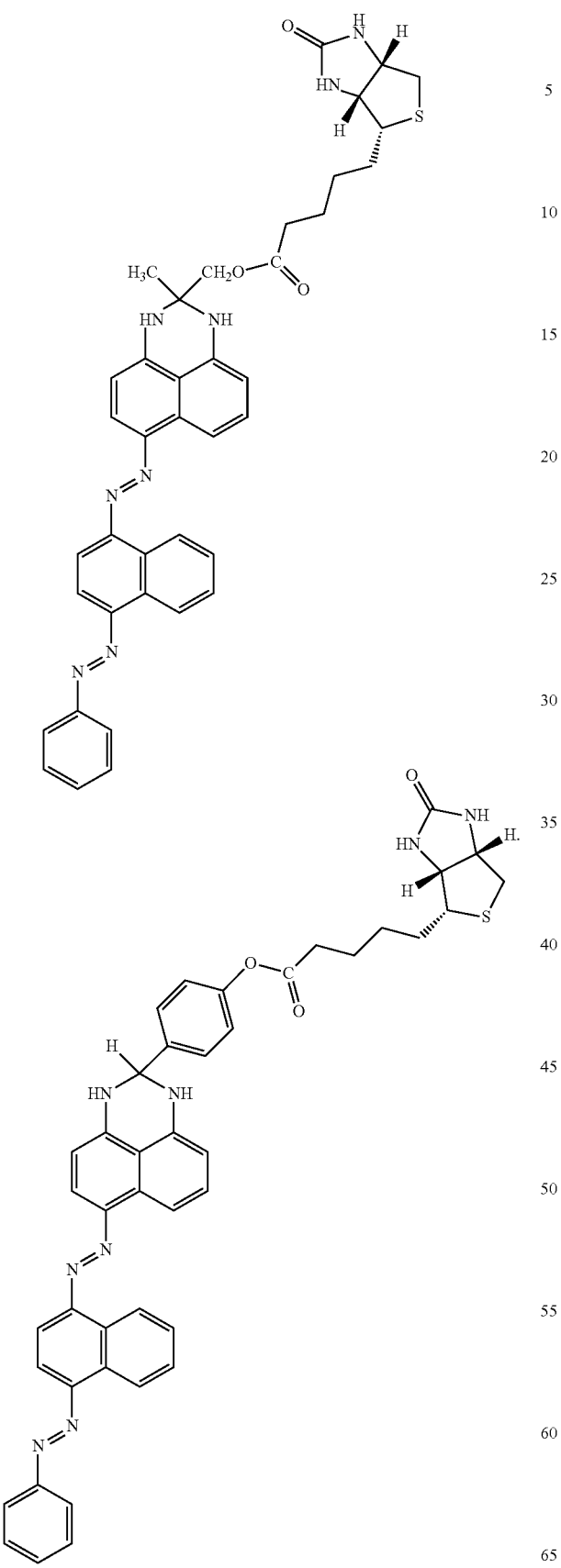

14. A process for the preparation of a compound according to claim 1, comprising either Step 1 or Step 2, as shown below:

Step 1)

reacting an SBB analogue compound of the general structure (2A) or (3A) shown below:

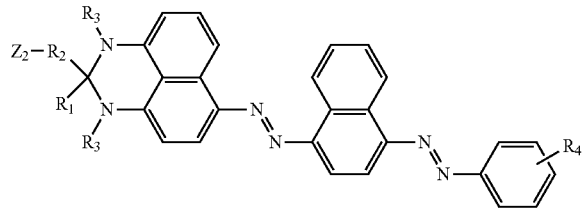

(2A)

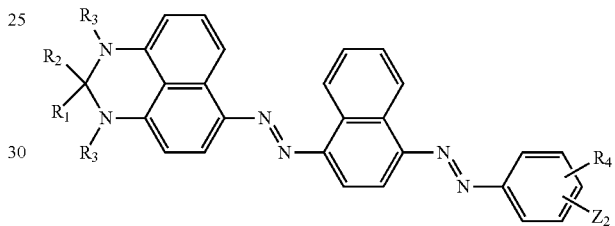

(3A)

wherein:

$R_1$ to $R_4$ are as defined in claim 1; and

Z is either $Z_1$ or Ar—$Z_1$, and $Z_1$ is selected from the group consisting of —O—, —NH—, —O(CH$_2$)$_n$CH$_2$O—, —(CH$_2$)$_q$O— and —COO—, wherein n is an integer selected from 1 to 9, wherein q is an integer selected from 1 to 4, and wherein Ar is an aryl group optionally substituted with one or more of the following substituents halogen, (1-6C)alkyl, (1-6C)alkenyl or (1-5C)alkoxy;

with a hapten selected from the group consisting of biotin, digoxigenin, 2,4-dinitrophenol, and fluorescein; and wherein the reaction is optionally carried out in the presence of a catalyst or coupling agent;

Step 2)

reacting a compound of formula A, shown below:

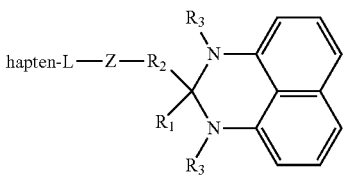

(A)

wherein hapten, L, Z and $R_1$ to $R_3$ are all as defined in claim 1;

with a compound of formula X, shown below:
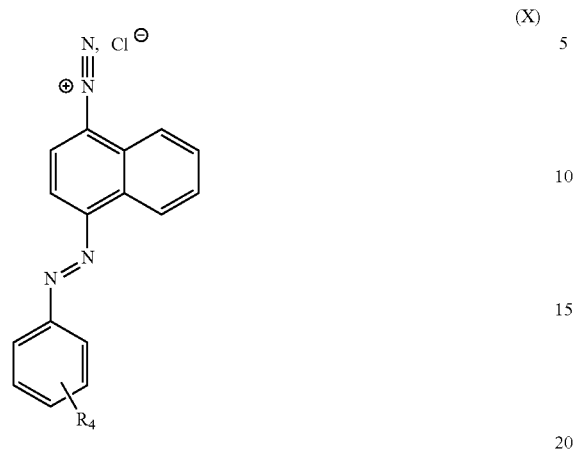
(X)
wherein R₄ is as defined in claim 1.
* * * * *